(12) United States Patent
Sung et al.

(10) Patent No.: US 8,202,508 B1
(45) Date of Patent: *Jun. 19, 2012

(54) PHARMACEUTICAL COMPOSITION OF NANOPARTICLES FOR PROTEIN DRUG DELIVERY

(75) Inventors: Hsing-Wen Sung, Hsinchu (TW); Kiran Sonaje, Hsinchu (TW); Ho-Ngoc Nguyen, Hsinchu (TW); Er-Yuan Chuang, Hsinchu (TW); Hosheng Tu, Newport Beach, CA (US)

(73) Assignees: GP Medical, Inc., Newport Beach, CA (US); National Tsing Hua University, Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/372,492

(22) Filed: Feb. 13, 2012

Related U.S. Application Data

(63) Continuation-in-part of application No. 13/199,736, filed on Sep. 8, 2011, now Pat. No. 8,114,380.

(51) Int. Cl.
*A61K 51/00* (2006.01)
(52) U.S. Cl. .................... 424/1.69; 424/1.73
(58) Field of Classification Search ............... 424/1.69, 424/1.73
See application file for complete search history.

(56) References Cited

U.S. PATENT DOCUMENTS

| 6,649,192 B2 | 11/2003 | Fernandez et al. |
| 6,726,934 B1 | 4/2004 | Prokop |
| 2006/0051423 A1 | 3/2006 | Heppe et al. |

OTHER PUBLICATIONS

Lin Yh et al. "Preparation and characterization of nanoparticles shelled with chitosan for oral insulin delivery" Biomacomolecules 2007;8:146-152.

*Primary Examiner* — Maryam Monshipouri

(57) ABSTRACT

The invention discloses a pharmaceutical composition of bioactive nanoparticles composed of chitosan, poly-glutamic acid, and a bioactive agent for oral delivery. The chitosan-based nanoparticles are characterized with a positive surface charge and enhanced permeability for oral drug delivery.

20 Claims, 18 Drawing Sheets

Figure 2
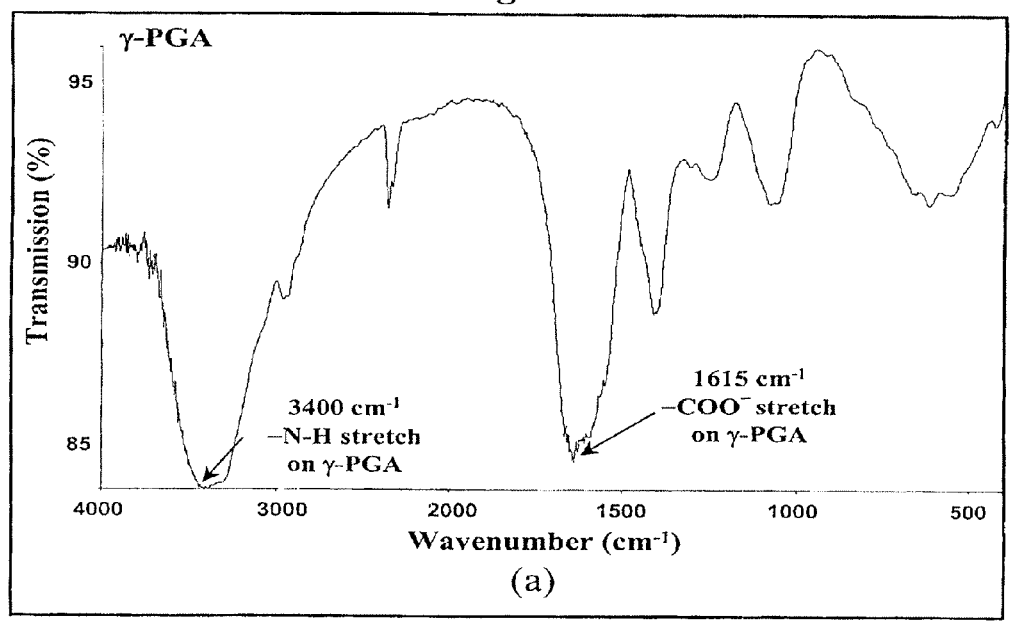
(a)
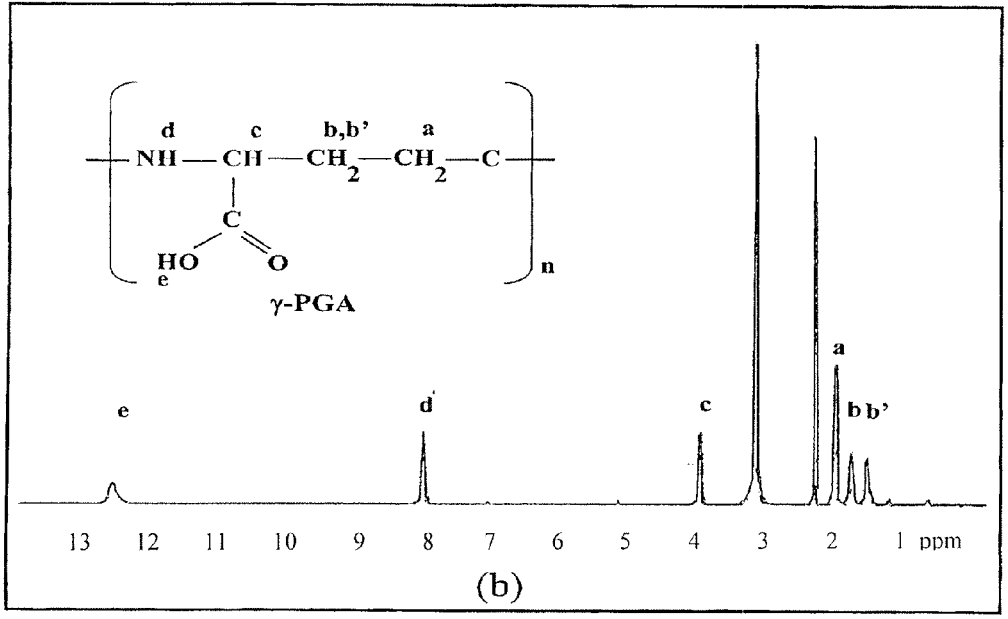
(b)

A. In the gastric cavity    B. Entering small intestine    C. In the intestinal tract

PHARMACEUTICAL COMPOSITION OF NANOPARTICLES FOR PROTEIN DRUG DELIVERY

CROSS-REFERENCE TO RELATED APPLICATIONS

This application is a continuation-in-part application of U.S. patent application Ser. No. 13/199,736, filed Sep. 8, 2011, now U.S. Pat. No. 8,114,380, which is a continuation application of U.S. patent application Ser. No. 13/065,989, filed Apr. 4, 2011, now U.S. Pat. No. 8,048,453, which is a continuation-in-part application of U.S. patent application Ser. No. 12/462,576, filed Aug. 5, 2009, now U.S. Pat. No. 7,919,072, which is a continuation-in-part application of U.S. patent application Ser. No. 12/286,504, filed Sep. 30, 2008, now U.S. Pat. No. 7,604,795, which is a continuation-in-part application of U.S. patent application Ser. No. 12/151,230, filed May 5, 2008, now U.S. Pat. No. 7,541,046, which is a continuation-in-part application of U.S. patent application Ser. No. 11/398,145, filed Apr. 5, 2006, now U.S. Pat. No. 7,381,716, which is a continuation-in-part application of U.S. patent application Ser. No. 11/284,734, filed Nov. 21, 2005, now U.S. Pat. No. 7,282,194, which is a continuation-in-part application of U.S. patent application Ser. No. 11/029,082, filed Jan. 4, 2005, now U.S. Pat. No. 7,265,090, the entire contents of which are incorporated herein by reference.

FIELD OF THE INVENTION

The present invention is related to general uses of nanoparticles that have a composition of chitosan and negatively charged substrate with at least one bioactive agent and their enhanced permeability for oral or parenteral drug delivery.

BACKGROUND OF THE INVENTION

Production of pharmaceutically bioactive peptides and proteins in large quantities has become feasible (Biomacromolecules 2004; 5:1917-1925). The oral route is considered the most convenient way of administering drugs for patients or an animal subject. Nevertheless, the intestinal epithelium is a major barrier to the absorption of hydrophilic drugs such as peptides and proteins (J. Control. Release 1996; 39:131-138). This is because hydrophilic drugs cannot easily diffuse across the cells through the lipid-bilayer cell membranes. Attentions have been given to improving paracellular transport of hydrophilic drugs (J. Control. Release 1998; 51:35-46). However, the transport of hydrophilic molecules via the paracellular pathway is, however, severely restricted by the presence of tight junctions that are located at the luminal aspect of adjacent epithelial cells (Annu. Rev. Nutr. 1995; 15:35-55). These tight junctions form a barrier that limits the paracellular diffusion of hydrophilic molecules. The structure and function of tight junctions is described, inter alia, in Ann. Rev. Physiol. 1998; 60:121-160 and in Ballard T S et al., Annu. Rev. Nutr. 1995; 15:35-55. Tight junctions do not form a rigid barrier but play an important role in the diffusion through the intestinal epithelium from lumen to bloodstream and vice versa.

Movement of solutes between cells, through the tight junctions that bind cells together into a layer such as the epithelial cells of the gastrointestinal tract, is termed paracellular transport. Paracellular transport is passive. Paracellular transport is dependent on electrochemical gradients generated by transcellular transport and solvent drag through tight junctions. Tight junctions form an intercellular barrier that separates the apical and basolateral fluid compartments of a cell layer. Movement of a solute through a tight junction from apical to basolateral compartments depends on the permeability of the tight junction for that solute.

Polymeric nanoparticles have been widely investigated as carriers for drug delivery (Biomaterials 2002; 23:3193-3201). Much attention has been given to the nanoparticles made of synthetic biodegradable polymers such as poly-ε-caprolactone and polylactide due to their biocompatibility (J. Drug Delivery 2000; 7:215-232; Eur. J. Pharm. Biopharm. 1995; 41:19-25). However, these nanoparticles are not ideal carriers for hydrophilic drugs because of their hydrophobic property. Some aspects of the invention relate to a novel nanoparticle system, composed of hydrophilic chitosan and poly(glutamic acid) hydrogels; the nanoparticles are prepared by a simple ionic-gelation method. This technique is promising as the nanoparticles are prepared under mild conditions without using harmful solvents. It is known that organic solvents may cause degradation of peptide or protein drugs that are unstable and sensitive to their environments (J. Control. Release 2001; 73:279-291).

Following the oral drug delivery route, protein drugs are readily degraded by the low pH of gastric medium in the stomach. The absorption of protein drugs following oral administration is challenging due to their high molecular weight, hydrophilicity, and susceptibility to enzymatic inactivation. Protein drugs at the intestinal epithelium cannot partition into the hydrophobic membrane, leaving only the epithelial barrier via the paracellular pathway. However, the tight junction forms a barrier that limits the paracellular diffusion of hydrophilic molecules.

Chitosan (CS), a cationic polysaccharide, is generally derived from chitin by alkaline deacetylation (J. Control. Release 2004; 96:285-300). It was reported from literature that CS is non-toxic and soft-tissue compatible (Biomacromolecules 2004; 5:1917-1925; Biomacromolecules 2004; 5:828-833). Additionally, it is known that CS has a special property of adhering to the mucosal surface and transiently opening the tight junctions between epithelial cells (Pharm. Res. 1994; 11:1358-1361). Most commercially available CSs have a quite large molecular weight (MW) and need to be dissolved in an acetic acid solution at a pH value of approximately 4.0 or lower, which is somewhat impractical. However, there are potential applications of CS in which a low MW would be essential. Given a low MW, the polycationic characteristic of CS can be used together with a good solubility at a pH value close to physiological ranges (Eur. J. Pharm. Biopharm. 2004; 57:101-105). Loading of peptide or protein drugs at physiological pH ranges would preserve their bioactivity. On this basis, a low-MW CS, obtained by depolymerizing a commercially available CS using cellulase, is disclosed herein to prepare nanoparticles of the present invention.

Thanou et al. reported chitosan and its derivatives as intestinal absorption enhancers (Adv Drug Deliv Rev 2001; 50:S91-S101). Chitosan, when protonated at an acidic pH, is able to increase the paracellular permeability of peptide drugs across mucosal epithelia. Co-administration of chitosan or trimethyl chitosan chloride with peptide drugs were found to substantially increase the bioavailability of the peptide in animals compared with administrations without the chitosan component.

The γ-PGA, an anionic peptide, is a natural compound produced as capsular substance or as slime by members of the genus *Bacillus* (Crit. Rev. Biotechnol. 2001; 21:219-232). γ-PGA is unique in that it is composed of naturally occurring L-glutamic acid linked together through amide bonds. It is reported from literature that this naturally occurring γ-PGA is a water-soluble, biodegradable, and non-toxic polymer. A polyamino carboxylic acid (complexone), such as diethylene triamine pentaacetic acid, has showed enzyme resistant property. It is clinical beneficial to incorporate a PGA-complexone conjugate as a negative substrate and chitosan as a positive substrate in a drug delivery nanoparticle formulation for better absorption performance with reduced enzymatic effect.

SUMMARY OF THE INVENTION

It is one object of the present invention to provide a novel, unique nanoparticle system and methods of preparation for protein/peptide drug or bioactive agent delivery using a simple and mild ionic-gelation method upon addition of a poly-γ-glutamic acid (γ-PGA) solution (or other negatively charged component, such as PGA-complexion conjugate) into regular molecular weight chitosan (CS) solution. In one embodiment, the chitosan employed are N-trimethyl chitosan (TMC), low MW-chitosan, EDTA-chitosan, pegylated chitosan (PEG-chitosan), mono-N-carboxymethyl chitosan (MCC), chitosan derivatives, and combinations thereof that is positively charged. In one embodiment, the molecular weight of a low-MW CS of the present invention is about 80 kDa or less, preferably at about 40-50 kDa, adapted for adequate solubility at a pH that maintains the bioactivity of protein and peptide drugs. It is stipulated that a chitosan particle with about 30-50 kDa molecular weight is kidney inert. The particle size and the zeta potential value of the prepared nanoparticles are controlled by their constituted compositions. The results obtained by the TEM (transmission electron microscopy) and AFM (atomic force microscopy) examinations showed that the morphology of the prepared nanoparticles is generally spherical or spheroidal in shape.

Some aspects of the invention relate to a method of enhancing epithelial permeation (for example, intestinal or blood brain paracellular transport) configured for delivering at least one bioactive agent, comprising administering nanoparticles composed of γ-PGA and chitosan, in an animal subject. Administering the nanoparticles may be via oral administration, intranasal absorption, subcutaneous injection or injection into a blood vessel. In one embodiment, the chitosan dominates on the surface of the nanoparticles as shell substrate and the negatively charged γ-PGA or other suitable component, with chitosan present, as core substrate. In another embodiment, a substantial surface of the nanoparticles is characterized with a positive charge. In a further embodiment, the nanoparticles of the present invention comprise at least one positively charged shell substrate and at least one negatively charged core substrate. In one embodiment, all of the negatively charged core substrate conjugates with a portion of the positively charged shell substrate in the core portion so to maintain a substantially zero-charged (neutral) core. In one embodiment, at least one bioactive agent or protein drug is conjugated with the negatively charged core substrate or the substantially zero-charged (neutral) core.

In a further embodiment, the nanoparticles have a mean particle size between about 50 and 400 nanometers, preferably between about 100 and 300 nanometers, and most preferably between about 100 and 200 nanometers.

In some embodiments, the nanoparticles are loaded with a therapeutically effective amount of at least one bioactive agent, wherein the bioactive agent is selected from the group consisting of proteins, peptides, nucleosides, nucleotides, antiviral agents, antineoplastic agents, antibiotics, oxygen-enriching agent, oxygen-containing agent, anti-epileptic drug, and anti-inflammatory drugs. The anti-epileptic drug may include Neurontin (gabapentin, a gamma-aminobutyric acid analog), Lamictal (lamotrigine, shown to act at voltage-sensitive sodium channels, stabilizing neural membranes and inhibiting the release of excitatory neural transmitters), Febatol (felbamate, shown to have weak inhibitory effects on GABA receptor binding sites), Topamax (topiramate, has a novel chemical structure derived from D-fructose that blocks voltage-sensitive sodium channels, enhances the activity of GABA, an inhibitory neurotransmitter, and blocks the action of glutamate, an excitatory neurotransmitter), and/or Cerebyx (fosphenyloin, a phenyloin precursor that is rapidly converted after parenteral administration).

Further, the bioactive agent may be selected from the group consisting of calcitonin, cyclosporin, insulin, oxytocin, tyrosine, enkephalin, tyrotropin releasing hormone, follicle stimulating hormone, luteinizing hormone, vasopressin and vasopressin analogs, catalase, superoxide dismutase, interleukin-11, interferon, colony stimulating factor, tumor necrosis factor, tumor necrosis factor inhibitor, and melanocyte-stimulating hormone. Interleukin eleven (IL-11) is a thrombopoietic growth factor that directly stimulates the proliferation of hematopoietic stem cells and megakaryocyte progenitor cells and induces megakaryocyte maturation resulting in increased platelet production (Oprelvekin®). In one preferred embodiment, the bioactive agent is an Alzheimer antagonist.

Some aspects of the invention relate to an oral dose of nanoparticles that effectively enhance epithelial permeation or paracellular transport comprising γ-PGA or α-PGA (or other PGA derivatives, such as PGA-complexone conjugate that is negatively charged) and low molecular weight chitosan, wherein the chitosan dominates on a surface of the nanoparticles. Some aspects of the invention relate to an oral dose of nanoparticles that effectively enhance epithelial permeation (e.g., intestinal or blood brain paracellular transport) comprising a negative component, such as γ-PGA, α-PGA, heparin, or heparan sulfate, in the core, and low molecular weight chitosan dominating on the surface of the nanoparticles with positive surface charges. The core substrate may be selected from the group consisting of heparin, heparin analogs, low molecular weight heparin, glycosaminoglycans, and alginate, whereas the bioactive agent is selected from the group consisting of chondroitin sulfate, hyaluronic acid, growth factor and protein with a pharmaceutically effective amount.

In a further embodiment, the nanoparticles comprise at least one bioactive agent, such as insulin, insulin analog, Alzheimer's disease antagonist, Parkison's disease antagonist, or other protein/peptide. The bioactive agent for treating Alzheimer's disease may include memantine hydrochloride (Axura® by Merz Pharmaceuticals), donepezil hydrochloride (Aricept® by Eisai Co. Ltd.), rivastigmine tartrate (Exelon® by Novartis), galantamine hydrochloride (Reminyl® by Johnson & Johnson), or tacrine hydrochloride (Cognex® by Parke Davis). Examples of insulin or insulin analog products include, but not limited to, Humulin® (by Eli Lilly), Humalog® (by Eli Lilly) and Lantus® (by Aventis).

Some aspects of the invention provide a dose of nanoparticles that enhance epithelial permeation, intestinal permeation, or blood brain paracellular transport. Each nanoparticle comprises three components; the first component of at least one bioactive agent, a second component of low molecular weight chitosan that is positively charged and a third component that is negatively charged, wherein the second component dominates on a surface of the nanoparticle. In one embodiment, the third component is γ-PGA, α-PGA, derivatives (such as PGA-complexone conjugate and the like), salts of PGA, or combinations thereof, heparin or alginate. In another embodiment, the first component comprises insulin at a concentration range of 0.075 to 0.091 mg/ml, the second component at a concentration range of 0.67 to 0.83 mg/ml, and the third component comprises γ-PGA at a concentration range of 0.150 to 0.184 mg/ml. The at least one bioactive agent may comprise an antagonist for Alzheimer's disease or for treatment of Alzheimer's disease selected from the group consisting of memantine hydrochloride, donepezil hydrochloride, rivastigmine tartrate, galantamine hydrochloride, and tacrine hydrochloride. In a further embodiment, the at least one bioactive agent is insulin or insulin analog. In still another embodiment, the at least one bioactive agent is selected from the group consisting of proteins, peptides, nucleosides, nucleotides, antiviral agents, antineoplastic agents, antibiotics, oxygen-enriching agent, oxygen-containing agent, calcitonin, vancomycin, and anti-inflammatory drugs.

Some aspects of the invention provide a dose of nanoparticles that enhance permeation, wherein the nanoparticles are further encapsulated in a capsule or hard-cap capsule. In one embodiment, the nanoparticles are freeze-dried. In one embodiment, the interior surface of the capsule is treated to be lipophilic or hydrophobic so to keep the enclosed ingredients or nanoparticles intact or passive to the interior surface. In another embodiment, the interior surface or the exterior surface of the capsules is enteric-coated or treated with an enteric coating polymer.

Some aspects of the invention provide a method of enhancing epithelial permeation comprising administering a dose of nanoparticles, wherein each nanoparticle comprises a first component of at least one bioactive agent, a second component of low molecular weight chitosan, and a third component that is negatively charged, wherein the second component dominates on a surface of the nanoparticle. In one embodiment, the step of administering the dose of nanoparticles is via oral administration for enhancing epithelial permeation or intestinal paracellular transport. In another embodiment, the step of administering the dose of nanoparticles is via intravenous administration or injection to a blood vessel for enhancing blood brain paracellular transport or reducing the blood-brain barrier (BBB). In another embodiment, the step of administering the nanoparticles is via subcutaneous injection, intramuscular injection, or intranasal spraying.

In one embodiment, the orally administered insulin-containing nanoparticles comprise an effective dosage amount of the insulin to treat the diabetes between about 5 units to 95 units insulin, preferably between about 15 units to 45 units, per kilogram body weight of the animal subject. In a further embodiment, the insulin-containing nanoparticle comprises a trace amount of zinc or calcium, or is treated with enteric coating.

In one embodiment, the bioactive agent-containing nanoparticles further comprise at least one permeation enhancer, wherein the permeation enhancer may be selected from the group consisting of $Ca^{2+}$ chelators, bile salts, anionic surfactants, medium-chain fatty acids, phosphate esters, and the like. In another embodiment, the nanoparticles and the permeation enhancer are co-encapsulated in a capsule or are encapsulated separately in two sets of capsules for co-administration.

Some aspects of the invention provide a method of treating Alzheimer's diseases of an animal subject comprising intravenously administering bioactive nanoparticles with an effective dosage to treat the Alzheimer's diseases, wherein the bioactive nanoparticles comprises a positively charged shell substrate, a negatively charged or substantially neutral-charged core substrate, and at least one bioactive agent for treating Alzheimer's disease, wherein at least one bioactive agent is selected from the group consisting of memantine hydrochloride, donepezil hydrochloride, rivastigmine tartrate, galantamine hydrochloride, and tacrine hydrochloride.

In one embodiment, the effective treatment of the Alzheimer's diseases comprises administering at least one bioactive agent for treating Alzheimer's diseases at about 10 mg to 40 mg per day over a period of one month to one year or longer. In another embodiment, at least a portion of the shell substrate is crosslinked, preferably at a degree of crosslinking less than about 50%, or most preferably between about 1% and 20%.

One aspect of the invention provides a pharmaceutical composition of nanoparticles, wherein the nanoparticles may be freeze-dried to form solid dried nanoparticles. The dried nanoparticles may be loaded in a capsule (such as a two-part hard gelatin capsule) or a tablet, which may be further enterically coated, for oral administration in an animal subject. The freeze-dried nanoparticles can be rehydrated in a solution or by contacting body fluid as to revert to wet nanoparticles having positive surface charge with substantially the properties of the pre-lyophilized nanoparticles. In one embodiment, nanoparticles may be mixed with trehalose or with hexan-1, 2,3,4,5,6-hexyl in a freeze-drying process. In one embodiment, the interior surface of the capsule is treated to be lipophilic or hydrophobic. In another embodiment, the exterior surface of the capsule is enteric-coated or treated with an enteric coated polymer.

Some aspects of the invention provide a pharmaceutical composition of nanoparticles that enhance epithelial permeation or paracellular transport, each nanoparticle comprising a shell component and a core component, wherein at least a portion of the shell component comprises chitosan and wherein the core component is comprised of $MgSO_4$, sodium tripolyphosphate, at least one bioactive agent, and a negatively charged compound, wherein a substantial portion of the negatively charged compound is electrostatically bound to the chitosan.

Some aspects of the invention provide an orally deliverable capsule to an animal subject comprising: (a) an empty capsule; and (b) bioactive nanoparticles loaded within the empty capsule, wherein the nanoparticles comprise a shell substrate of chitosan, a negatively charged or substantially neutral-charged core substrate, and (c) at least one bioactive agent. In one embodiment, the empty capsule comprises a two-part hard gelatin capsule. In another embodiment, the capsule is treated with an enteric coating polymer. In one embodiment, the interior surface of the capsule may be treated with hydrophobic or enteric coating.

One object of the present invention is to provide a method of manufacturing the orally deliverable capsule, the method comprising the steps of: (a) providing an empty capsule; (b) providing bioactive nanoparticles, wherein the nanoparticles comprise a shell substrate of chitosan, a negatively charged or substantially zero-charged core substrate, and at least one bioactive agent; (c) freeze-drying the nanoparticles; and (d) filling the freeze-dried bioactive nanoparticles into the empty capsule, thereby producing an orally deliverable capsule. In one embodiment, the bioactive nanoparticles further comprise zinc, magnesium sulfate and TPP.

Some aspects of the invention provide a pharmaceutical composition of nanoparticles for oral administration in an animal subject, the nanoparticles comprising a shell portion that is dominated by positively charged chitosan, a core portion that contains negatively charged substrate, wherein the negatively charged substrate is at least partially neutralized with a portion of the positively charged chitosan in the core portion, and at least one bioactive agent loaded within the nanoparticles. In one embodiment, the bioactive agent is a non-insulin exenatide, a non-insulin pramlintide, GLP-1, GLP-1 analog, GLP-2, GLP-2 analog, insulin, insulin analog, or combinations thereof. In one embodiment, the nanoparticles are formed via a simple and mild ionic-gelation method. Glucagon-like peptide-2 (GLP-2) is a recently identified potent intestinotrophic factor. The effect of GLP-2 treatment on intestinal epithelial barrier function in mice shows that the glucagon-like peptide-2 enhances intestinal epithelial barrier function of both transcellular and paracellular pathways in the mouse. Nevertheless, glucagon-like peptide-2 reduces intestinal permeability but does not modify the onset of Type 1 diabetes in the nonobese diabetic mouse.

In one embodiment, a surface of the nanoparticles of the pharmaceutical composition of the present invention is characterized with a positive surface charge, wherein the nanoparticles have a surface charge from about +15 mV to about +50 mV. In another embodiment, the nanoparticles have a mean particle size between about 50 and 400 nanometers. In still another embodiment, at least a portion of the shell portion of the nanoparticles is crosslinked. In a further embodiment, the nanoparticles are in a form of freeze-dried powder. In one embodiment, the nanoparticles of the pharmaceutical composition of the present invention further comprise iron, zinc, calcium, magnesium sulfate and TPP.

Some aspects of the invention provide a method of delivering a bioactive agent to blood circulation in an animal subject, comprising: (a) providing nanoparticles according to the pharmaceutical composition of the present invention, wherein the nanoparticles are formed via a simple and mild ionic-gelation method; (b) administering the nanoparticles orally toward an intestine of the animal subject; (c) urging the nanoparticles to be absorbed onto a surface of an epithelial membrane of the intestine; (d) permeating bioactive agent to pass through an epithelial barrier of the intestine; and (e) releasing the bioactive agent into the blood circulation. In one embodiment, the bioactive agent is selected from the group consisting of exenatide, pramlintide, insulin, insulin analog, and combinations thereof.

Some aspects of the invention provide a method of delivering a bioactive agent to an animal subject orally, the method comprising formulating nanoparticles containing bioactive agent according to the principles of the present disclosure, wherein the nanoparticles are suspended in liquid. In one embodiment, the liquid with nanoparticles containing bioactive agent is served as a sport drink or energy drink. In one embodiment, the bioactive agent is an oxygen-enriching agent or oxygen-containing agent (such as hemoglobin). In another embodiment, the bioactive agent is an energy-enhancing agent, such as $CoQ_{10}$. Coenzyme $Q_{10}$ (also known as ubiquinone, ubidecarenone, coenzyme Q, and abbreviated at times to $CoQ_{10}$, CoQ, Q10, or Q) is a benzoquinone, where Q refers to the quinone chemical group, and 10 refers to the isoprenyl chemical subunits. This oil-soluble vitamin-like substance is present in most eukaryotic cells, primarily in the mitochondria. It is a component of the electron transport chain and participates in aerobic cellular respiration, generating energy in the form of ATP. Ninety-five percent of the human body's energy is generated this way. Therefore, those organs with the highest energy requirements—such as the heart and the liver—have the highest $CoQ_{10}$ concentrations or requirement.

Some aspects of the invention provide a method of reducing inflammatory response caused by tumor necrosis factor in an animal subject, the method comprising orally administering nanoparticles composed of a TNF inhibitor, chitosan, and a core substrate of poly(glutamic acid) or heparin. In one embodiment, the TNF inhibitor is a monoclonal antibody. In another embodiment, the TNF inhibitor is infliximab or adalimumab. In one embodiment, the TNF inhibitor is a circulating receptor fusion protein. In another embodiment, the TNF inhibitor is etanercept.

In one embodiment, the chitosan of the nanoparticles has a molecular weight about 80 kDa or less. In another embodiment, the chitosan is N-trimethyl chitosan or chitosan derivatives, such as EDTA-chitosan. In still another embodiment, the poly(glutamic acid) of the nanoparticles is γ-PGA, α-PGA, PGA-complexone conjugate, derivatives of PGA, salts of PGA, or combinations thereof. In one embodiment, the nanoparticles have a mean particle size between about 50 and 400 nanometers.

Some aspects of the invention relate to a method of treating infections caused by microorganisms in an animal subject, the method comprising administering nanoparticles composed of an antibiotic, chitosan, and a core portion of negatively charged substrate, wherein a surface of the nanoparticles is dominated by the chitosan.

In one embodiment, the antibiotic is selected from the group consisting of vancomycin, glycylcycline antibiotics (such as Tigecycline), lincosamide antibiotics (such as Lincomycin), beta-lactam antibiotic (such as Penicillin, Ampicillin, and Piperacillin), bacteriophages, antitumor antibiotics, and aminoglycoside antibiotics.

Some aspects of the invention provide a method of treating diabetes in a subject, comprising administering bioactive nanoparticles to the subject, wherein the nanoparticles comprise a shell portion that is dominated by positively charged chitosan, a core portion that contains negatively charged substrate, wherein the negatively charged substrate is at least partially neutralized with a portion of the positively charged chitosan and at least one non-insulin anti-diabetic drug. In one embodiment, the nanoparticles are encapsulated in capsules. In another embodiment, the capsules further comprise a second non-insulin anti-diabetic drug of the at least one non-insulin anti-diabetic drug. In one embodiment, the non-insulin anti-diabetic drug is metformin, an insulin secretagogue, a GLP-1 analog, a DPP-4 inhibitor, or selected from the group consisting of alpha-glucosidase inhibitors, amylin analog, sodium-glucose co-transporter type 2 (SGLT2) inhibitors, benfluorex, and tolrestat. In another embodiment, the bioactive nanoparticles further comprise insulin or insulin analog. There are several reports suggesting that GLP-1 or GLP-1 analog has an appetite-suppressing action.

Some aspects of the invention provide administering bioactive nanoparticles to a subject with enhanced enzymatic resistance to the bioactive agent inside the bioactive nanoparticles, wherein the nanoparticles comprise a shell portion that is dominated by positively charged chitosan, a core portion that contains negatively charged substrate, wherein the negatively charged substrate is at least partially neutralized with a portion of the positively charged chitosan and at least one enzyme-resistant agent. In one embodiment, the enzyme-resistant agent is complexone, such as diethylene triamine pentaacetic acid (DTPA) or ethylene diamine tetraacetic acid (EDTA), which may conjugate with the chitosan substrate or the PGA substrate in the nanoparticle formulation.

Some aspects of the invention provide a pharmaceutical composition of nanoparticles, the nanoparticles comprising a shell portion that is dominated by positively charged chitosan, a core portion that comprises one negatively charged substrate, wherein the substrate is PGA-complexone conjugate, wherein the negatively charged substrate is at least partially neutralized with a portion of the positively charged chitosan in the core portion, and at least one bioactive agent loaded within the nanoparticles. In one embodiment, the pharmaceutical composition of nanoparticles further comprises a pharmaceutically acceptable carrier, diluent, or excipient.

In one embodiment, the nanoparticles are encapsulated in capsules, wherein the capsules further comprise at least a solubilizer, bubbling agent, emulsifier, pharmacopoeial excipients or at least one permeation enhancer. In another embodiment, the nanoparticles are freeze-dried, thereby the nanoparticles being in a powder form.

Some aspects of the present invention provide a method of treating an inflammatory bowel disease of an animal subject, the method comprising administering bioactive nanoparticles to the animal subject orally, wherein the bioactive nanoparticles consist of at least one anti-inflammatory agent, positively charged chitosan, optionally a zero-charge substance and a negatively charged substrate, wherein a surface of the nanoparticles is dominated by the positively charged chitosan. In one embodiment, the negatively charged substrate is PGA that is selected from the group consisting of a PGA-complexone conjugate, γ-PGA, α-PGA, derivatives of PGA, salts of PGA, or combinations thereof. In another embodiment, the PGA-complexone conjugate is PGA-DTPA that is chelated to gadolinium.

In one embodiment, the inflammatory bowel disease is a Crohn's disease (autoimmune origin) or ulcerative colitis. In another embodiment, the anti-inflammatory agent is selected from the group consisting of mesalazine, prednisone, a TNF inhibitor, azathioprine (Imuran), methotrexate, 6-mercaptopurine, nystatin, antifungal agent, itraconazole, and fluconazole.

Some aspects of the invention provide a pharmaceutical composition of nanoparticles, the nanoparticles consisting of positively charged chitosan, optionally a zero-charge substance or bioactive agent, and a negatively charged substrate having gadolinium (Gd) chelated to the negatively charged substrate, wherein a surface of the nanoparticles is dominated by the positively charged chitosan. In one embodiment, the chitosan is N-trimethyl chitosan, EDTA-chitosan, low molecular weight chitosan, PEG-chitosan, mono-N-carboxymethyl chitosan, chitosan derivatives, or combinations thereof. In a preferred a ligand is attached a free —NH$_3$ group of the N-trimethyl chitosan. In another embodiment, the ligand includes a substrate, inhibitor, activator, or neurotransmitter, for example galactosamine.

In one embodiment, the negatively charged substrate of the nanoparticles is a PGA-complexone conjugate, γ-PGA, α-PGA, derivatives of PGA, salts of PGA, or combinations thereof. In a further embodiment, the PGA-complexone conjugate is PGA-DTPA.

In one embodiment, the nanoparticles of the pharmaceutical composition are formulated into a tablet, capsule, or pill configuration, wherein the tablet, capsule, or pill is optionally enterically coated (i.e., treated with an enteric coating polymer). In one embodiment, the capsule further comprises a pharmaceutically acceptable carrier, diluent, excipient, absorption enhancer, at least a solubilizer, bubbling agent, or emulsifier. In a further embodiment, the nanoparticles are freeze-dried, thereby the nanoparticles being in a powder form.

In one embodiment, the nanoparticles are used in (or characterized by) enhancing imaging contrast quality or property during an imaging procedure. In another embodiment, the nanoparticles are used in (or characterized by) cancer treatment therapy. The nanoparticles may be administered to an animal subject via an oral or parenteral route. The bioactive agent of the nanoparticles is selected from the group consisting of an anti-cancer drug, nystatin, antifungal agent, itraconazole, fluconazole, mesalazine, prednisone, a TNF inhibitor, azathioprine (Imuran), methotrexate, the 6-mercaptopurine. In one embodiment, the zero-charge substance of the nanoparticles is a permeation enhancer.

BRIEF DESCRIPTION OF THE DRAWINGS

Additional objects and features of the present invention will become more apparent and the disclosure itself will be best understood from the following Detailed Description of the Exemplary Embodiments, when read with reference to the accompanying drawings.

FIG. 2 shows (a) FT-IR and (b) $^1$H-NMR spectra of the purified γ-PGA obtained from microbial fermentation.

DETAILED DESCRIPTION OF THE EXEMPLARY EMBODIMENTS

Figure 1:
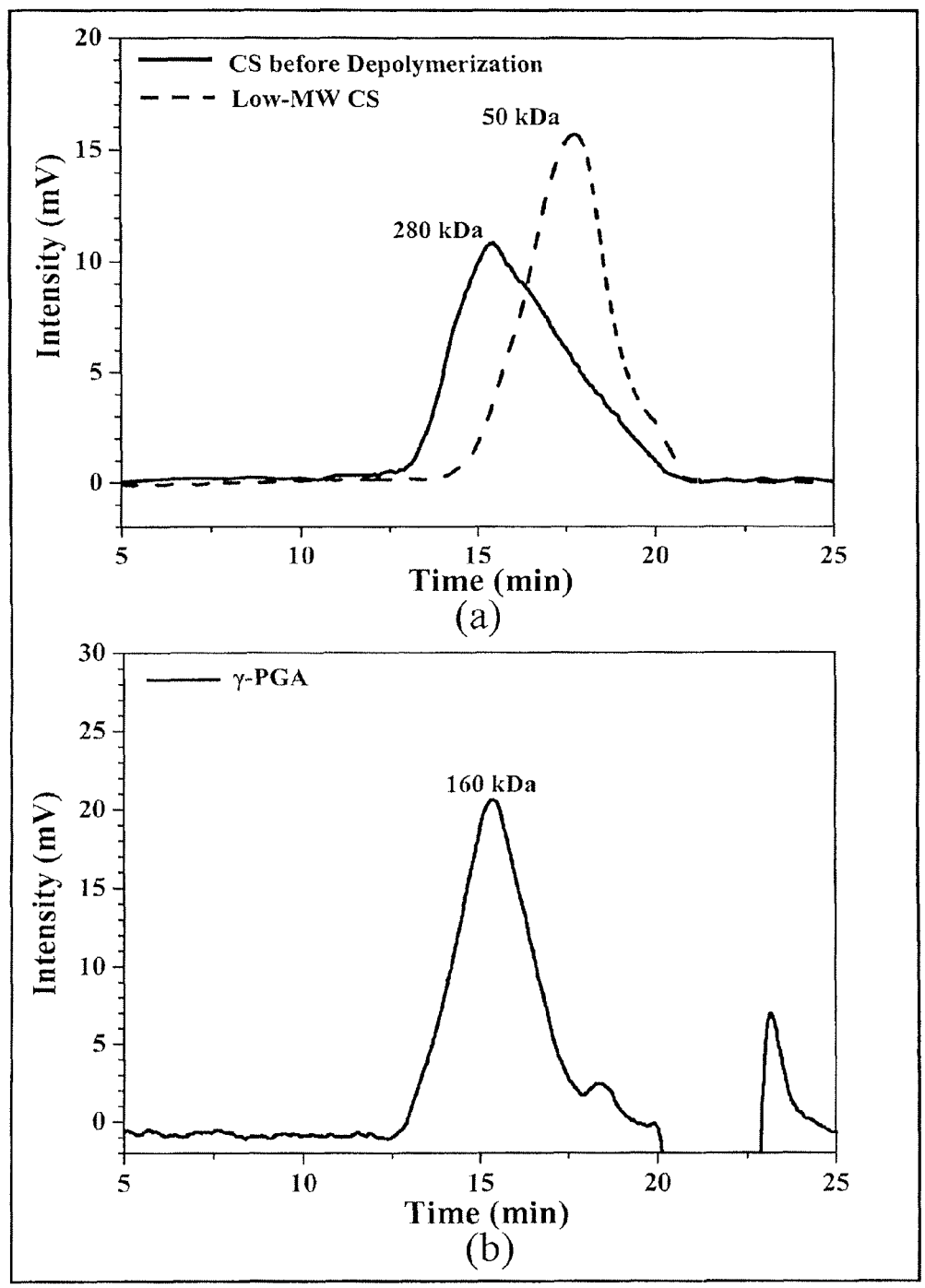
FIG. 1 shows GPC chromatograms of (a) standard-MW CS before depolymerization and the low-MW CS after depolymerization; (b) the purified γ-PGA obtained from microbial fermentation.

The preferred embodiments of the present invention described below relate particularly to the preparation of nanoparticles composed of chitosan/poly-glutamic acid/insulin and their permeability to enhance the intestinal or blood brain paracellular permeation by opening the tight junctions between epithelial cells. While the description sets forth various embodiment specific details, it should be understood that the description is illustrative only and should not be construed in any way as limiting the invention. Furthermore, various applications of the invention, and modifications thereto, which may occur to those who are skilled in the art, are also encompassed by the general concepts described below.

"Bioactive agent" herein is meant to include any agent that may affect the recipient (an animal subject) after being administered physically, physiologically, mentally, biochemically, biologically, or other bodily functions in a positive or negative manners. The 'bioactive agent' may include, but not limited to, drugs, protein, peptides, siRNA, enzymes, supplemental nutrients, vitamins, other active agents.

γ-PGA is a naturally occurring anionic homo-polyamide that is made of L-glutamic acid units connected by amide linkages between α-amino and γ-carboxylic acid groups (Crit. Rev. Biotechnol. 2001; 21:219-232). It is an exocellular polymer of certain *Bacillus* species that is produced within cells via the TCA cycle and is freely excreted into the fermentation broth. Its exact biological role is not fully known, although it is likely that γ-PGA is linked to increasing the survival of producing strains when exposed to environmental stresses. Because of its water-solubility, biodegradability, edibility, and non-toxicity toward humans and the environment, several applications of γ-PGA in food, cosmetics, medicine, and water treatment have been investigated in the past few years.

Example No. 1

Materials and Methods of Nanoparticles Preparation

CS (MW ~$2.8\times10^5$) with a degree of deacetylation of approximately 85% was acquired from Challenge Bioproducts Co. (Taichung, Taiwan). Acetic acid, cellulase (1.92 units/mg), fluorescein isothiocyanate (FITC), phosphate buffered saline (PBS), periodic acid, sodium acetate, formaldehyde, bismuth subnitrate, and Hanks' balanced salt solution (HBSS) were purchased from Sigma Chemical Co. (St. Louis, Mo.). Ethanol absolute anhydrous and potassium sodium tartrate were obtained from Merck (Darmstadt, Germany). Non-essential amino acid (NEAA) solution, fetal bovine serum (FBS), gentamicin and trypsin-EDTA were acquired from Gibco (Grand Island, N.Y.). Eagle's minimal essential medium (MEM) was purchased from Bio West (Nuaille, France). All other chemicals and reagents used were of analytical grade.

Example No. 2

Depolymerization of CS by Enzymatic Hydrolysis

Regular CS was treated with enzyme (cellulase) to produce low-MW CS according to a method described by Qin et al. with some modifications (Food Chem. 2004; 84:107-115). A solution of CS (20 g/l) was prepared by dissolving CS in 2% acetic acid. Care was taken to ensure the total solubility of CS. Then, the CS solution was introduced into a vessel and adjusted to the desired pH 5.0 with 2N aqueous NaOH. Subsequently, cellulase (0.1 g) was added into the CS solution (100 ml) and continuously stirred at 37° C. for 12 hours. Afterward, the depolymerized CS was precipitated with aqueous NaOH at pH 7.0-7.2 and the precipitated CS was washed three times with deionized water. The resulting low-MW CS was lyophilized in a freeze dryer (Eyela Co. Ltd, Tokyo, Japan).

The average molecular weight of the depolymerized CS was determined by a gel permeation chromatography (GPC) system equipped with a series of PL aquagel-OH columns (one Guard 8 μm, 50×7.5 mm and two MIXED 8 μm, 300×7.5 mm, PL Laboratories, UK) and a refractive index (RI) detector (R12000-F, SFD, Torrance, Calif.). Polysaccharide standards (molecular weights range from 180 to 788,000, Polymer Laboratories, UK) were used to construct a calibration curve. The mobile phase contained 0.01M $NaH_2PO_4$ and 0.5M $NaNO_3$ and was brought to a pH of 2.0. The flow rate of the mobile phase was 1.0 ml/min, and the columns and the R1 detector cell were maintained at 30° C.

Factors limiting applications of most commercially available CSs are their high molecular weight and corresponding high viscosity and poor solubility at physiological pH ranges. Low-MW CS overcomes these limitations and hence finds much wider applications in diversified fields. It was suggested that low-MW CS be used as a parenteral drug carrier due to its lower antigen effect (Eur. J. Pharm. Biopharm. 2004; 57:101-105). Low-MW CS was used as a non-viral gene delivery system and showed promising results (Int. J. Pharm. 1999; 178:231-243). Other studies based on animal testing showed the possibilities of low-MW CS for treatment of type 2 diabetes and gastric ulcer (Biol. Pharm. Bull. 2002; 25:188-192). Several hydrolytic enzymes such as lysozyme, pectinase, cellulase, bromelain, hemicellulase, lipase, papain and the like can be used to depolymerize CS (Biochim. Biophys. Acta 1996; 1291:5-15; Biochem. Eng. J. 2001; 7:85-88; Carbohydr. Res. 1992; 237:325-332).

FIG. 1a shows GPC chromatograms of both standard-MW (also known as regular-MW) and low-MW CS. It is known that cellulase catalyzes the cleavage of the glycosidic linkage in CS (Food Chem. 2004; 84:107-115). The low-MW CS used in the study was obtained by precipitating the depolymerized CS solution with aqueous NaOH at pH 7.0-7.2. This low-MW CS had a MW of about 50 kDa (FIG. 1a). In a preferred embodiment, the low molecular weight chitosan has a molecular weight of less than about 40 kDa, but above 10 kDa. Other forms of chitosan may also be applicable, including chitin, chitosan oligosaccharides, and derivatives thereof.

It was observed that the obtained low-MW CS can be readily dissolved in an aqueous solution at pH 6.0, while that before depolymerization needs to be dissolved in an acetic acid solution with a pH value about 4.0. Additionally, it was found that with the low-MW CS, the prepared nanoparticles had a significantly smaller size with a narrower distribution than their counterparts prepared with the high-MW (also known as standard-MW) CS (before depolymerization), due to its lower viscosity. As an example, upon adding a 0.10% γ-PGA aqueous solution into a 0.20% high-MW CS solution (viscosity 5.73±0.08 cp, measured by a viscometer), the mean particle size of the prepared nanoparticles was 878.3±28.4 nm with a polydispersity index of 1.0, whereas adding a 0.10% γ-PGA aqueous solution into the low-MW CS solution (viscosity 1.29±0.02 cp) formed nanoparticles with a mean particle size of 218.1±4.1 nm with a polydispersity index of 0.3 (n=5).

The purified γ-PGA used in forming nanoparticles of the present invention was analyzed by GPC, $^1$H-NMR, and FT-IR. As analyzed by GPC (FIG. 1b), the purified γ-PGA had a MW of about 160 kDa. In the FT-IR spectrum (FIG. 2a), a characteristic peak at 1615 cm$^{-1}$ for the associated carboxylic acid salt (—COO$^-$ antisymmetric stretch) on γ-PGA was observed. The characteristic absorption due to C=O in secondary amides (amide I band) was overlapped by the characteristic peak of —COO$^-$. Additionally, the characteristic peak observed at 3400 cm$^{-1}$ was the N—H stretch of γ-PGA. In the $^1$H-NMR spectrum (FIG. 2b), six chief signals were observed at 1.73 and 1.94 ppm (β-CH$_2$), 2.19 ppm (γ-CH$_2$), 4.14 ppm (α-CH), 8.15 ppm (amide), and 12.58 ppm (COOH). These results indicated that the observed FT-IR and $^1$H-NMR spectra correspond well to those expected for γ-PGA. Additionally, the fermented product after purification showed no detected macromolecular impurities by the $^1$H-NMR analysis, suggesting that the obtained white power of γ-PGA is highly pure.

Example No. 3

Preparation of the CS-γ-PGA Nanoparticles

Nanoparticles were obtained upon addition of γ-PGA aqueous solution (pH 7.4, 2 ml), using a pipette (0.5-5 ml, PLASTIBRAND®, BrandTech Scientific Inc., Germany), into a low-MW CS aqueous solution (pH 6.0, 10 ml) at varying concentrations (0.01%, 0.05%, 0.10%, 0.15%, or 0.20% by w/v) under magnetic stirring at room temperature. Nanoparticles were collected by ultracentrifugation at 38,000 rpm for 1 hour. Supernatants were discarded and nanoparticles were resuspended in deionized water for further studies. The nanoparticles thus obtained via the simple and mild ionic-gelation method described herein show typical characteristics in a spheroidal configuration with a particle size of between about 50 to 400 nm, a positive surface charge and a narrow polydispersity index. FT-IR was used to analyze peak variations of amino groups of low-MW CS and carboxylic acid salts of γ-PGA in the CS-γ-PGA nanoparticles.

Figure 3:
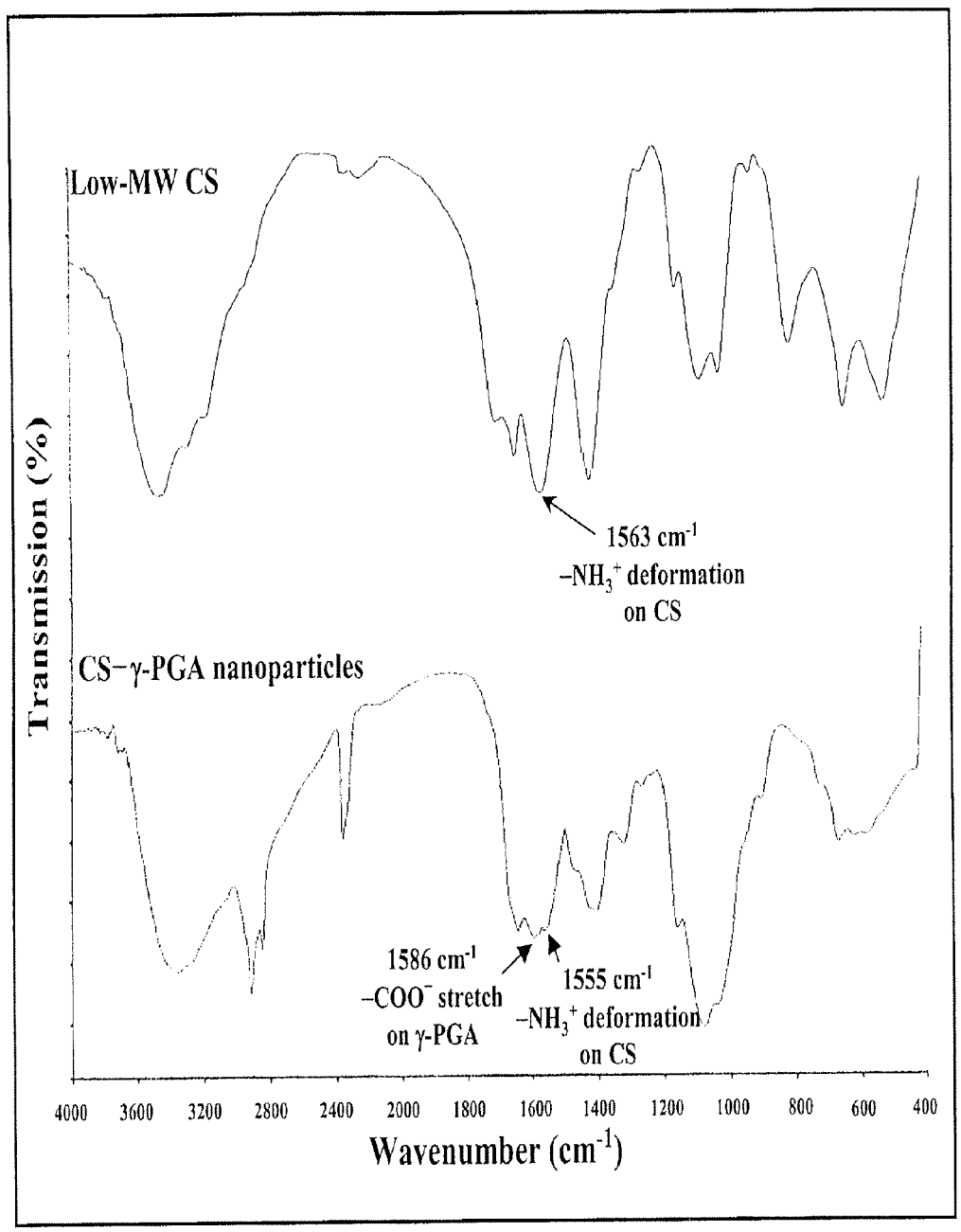
FIG. 3 shows FT-IR spectra of the low-MW CS and the prepared CS-γ-PGA nanoparticles.

As stated, nanoparticles were obtained instantaneously upon the addition of a γ-PGA aqueous solution (pH 7.4) into a low-MW CS aqueous solution (pH 6.0) under magnetic stirring at room temperature. FIG. 3 shows the FT-IR spectra of the low-MW CS and the CS-γ-PGA nanoparticles. As shown in the spectrum of CS, the characteristic peak observed at 1563 cm$^{-1}$ was the protonated amino group (—NH$_3^+$ deformation) on CS. In the spectrum of CS-γ-PGA complex, the characteristic peak at 1615 cm$^{-1}$ for —COO$^-$ on γ-PGA disappeared and a new peak at 1586 cm$^{-1}$ appeared, while the characteristic peak of —NH$_3^+$ deformation on CS at 1563 cm$^{-1}$ shifted to 1555 cm$^{-1}$. These observations are attributed to the electrostatic interaction between the negatively charged carboxylic acid salts (—COO$^-$) on γ-PGA and the positively charged amino groups (—NH$_3^+$) on CS (Int. J. Pharm. 2003; 250:215-226). The electrostatic interaction between the two polyelectrolytes (γ-PGA and CS) instantaneously induced the formation of long hydrophobic segments (or at least segments with a high density of neutral ion-pairs), and thus resulted in highly neutralized complexes that segregated into colloidal nanoparticles (Langmuir. 2004; 20:7766-7778).

Figure 10:
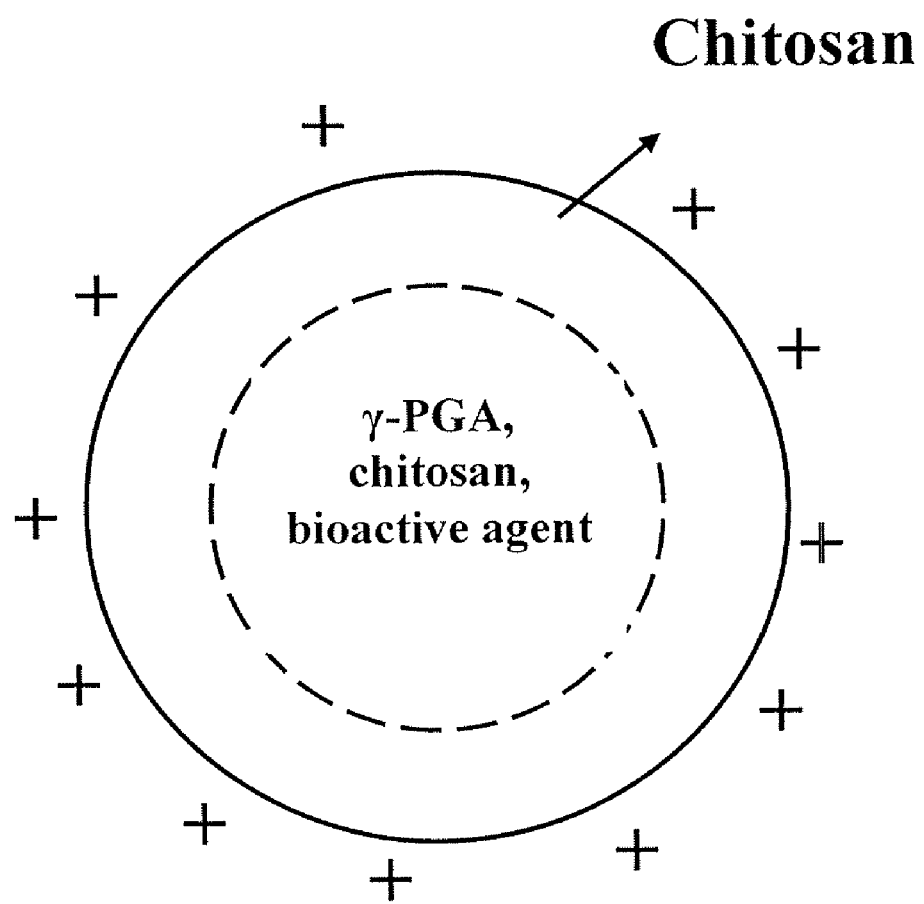
FIG. 10 shows a CS-γ-PGA nanoparticle with chitosan having positive surface charge.

The particle sizes and the zeta potential values of the CS-γ-PGA nanoparticles, prepared at varying concentrations of the γ-PGA and CS, were determined and the results are shown in Tables 1a and 1b. FIG. 10 shows a CS-γ-PGA nanoparticle with chitosan having positive surface charge. It was found that the particle size and the zeta potential value of the prepared nanoparticles were mainly determined by the relative amount of the local concentration of the γ-PGA in the added solution to the surrounding concentration of CS in the sink solution. At a fixed concentration of CS, an increase in the γ-PGA concentration allowed γ-PGA molecules to interact with more CS molecules, and thus formed a larger size of nanoparticles (Table 1a, p<0.05). When the amount of CS molecules exceeded that of local γ-PGA molecules, some of the excess CS molecules were entangled onto the surfaces of CS-γ-PGA nanoparticles.

Figure 4:
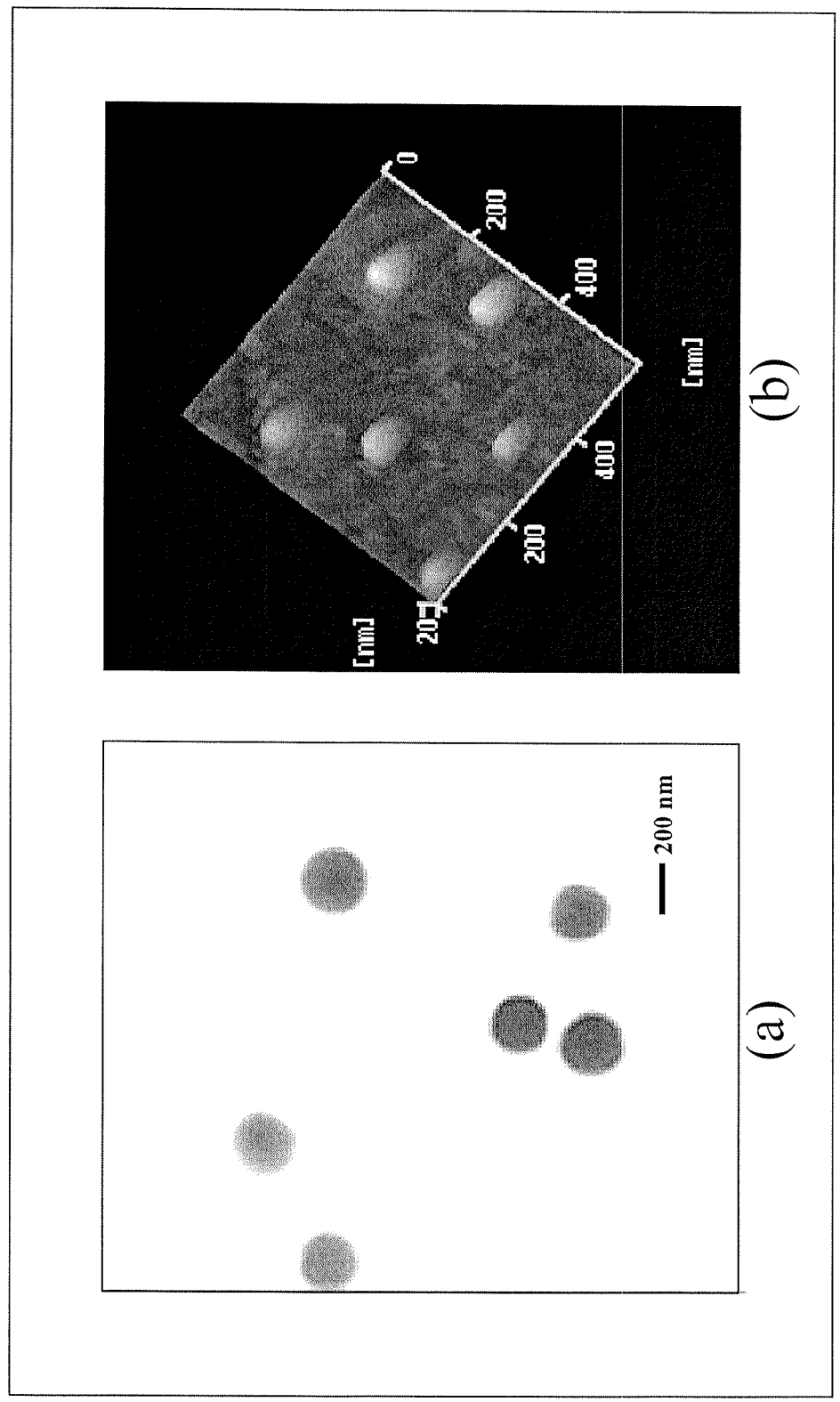
FIG. 4 shows (a) a TEM micrograph of the prepared CS-γ-PGA nanoparticles (0.10% γ-PGA:0.20% CS) and (b) an AFM micrograph of the prepared CS-γ-PGA nanoparticles (0.01% γ-PGA:0.01% CS).

Thus, the resulting nanoparticles may display a structure of a neutral polyelectrolyte-complex core surrounded by a positively charged CS shell (Table 1b) ensuring a colloidal stabilization (Langmuir. 2004; 20:7766-7778). In contrast, as the amount of local γ-PGA molecules sufficiently exceeded that of surrounding CS molecules, the formed nanoparticles had γ-PGA exposed on the surfaces and thus had a negative charge of zeta potential. Therefore, the particle size and the zeta potential value of the prepared CS-γ-PGA nanoparticles can be controlled by their constituted compositions. The results obtained by the TEM and AFM examinations showed that the morphology of the prepared nanoparticles was spherical in shape with a smooth surface (FIGS. 4a and 4b). Some aspects of the invention relate to nanoparticles having a mean particle size between about 50 and 400 nanometers, preferably between about 100 and 300 nanometers, and most preferably between about 100 and 200 nanometers.

The morphology of the nanoparticles is spherical in shape with a smooth surface at any pH between 2.5 and 6.6. In one embodiment, the stability of the nanoparticles of the present invention at a low pH around 2.5 enables the nanoparticles to be intact when exposed to the acidic medium in the stomach.

Figure 5:
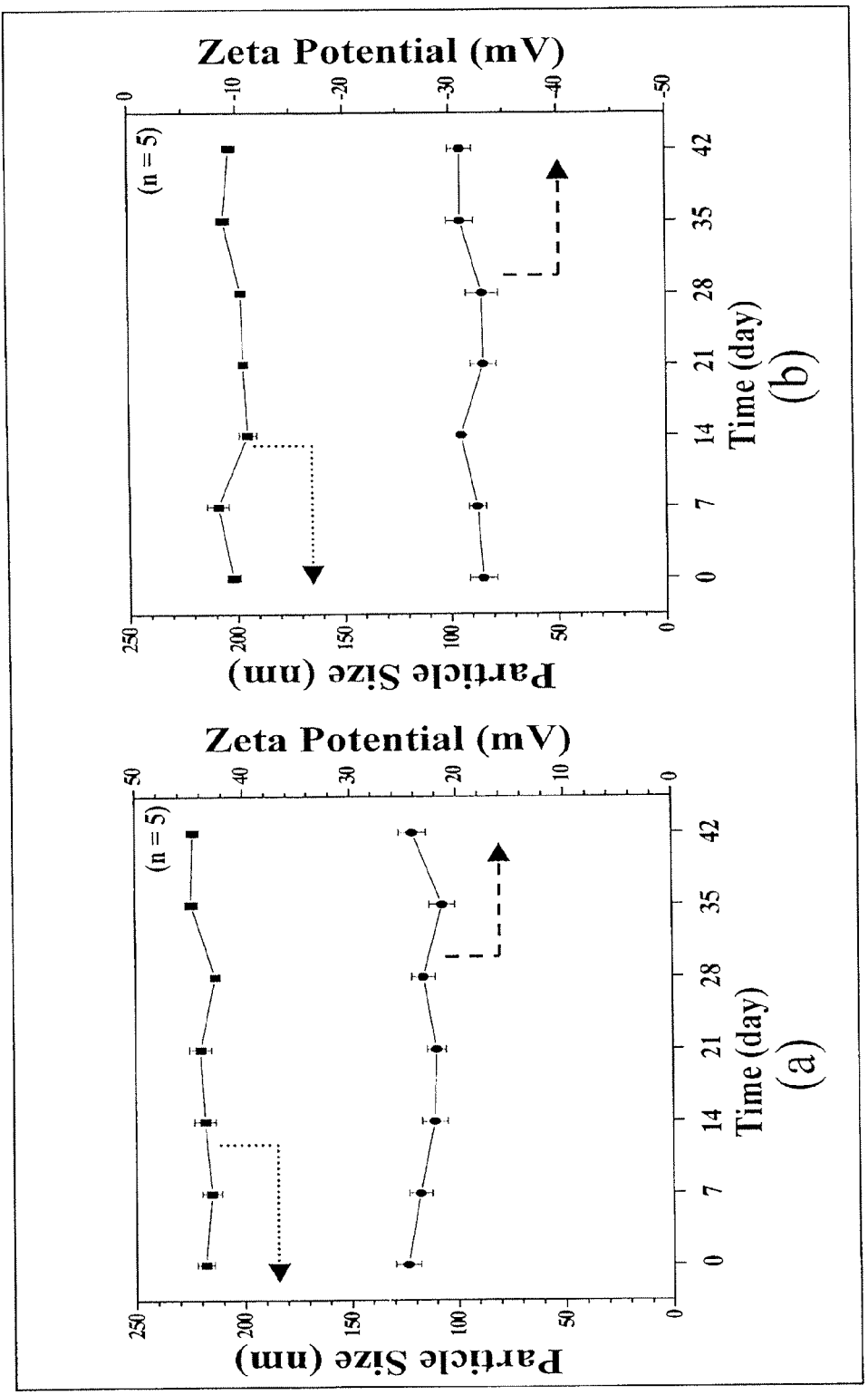
FIG. 5 shows changes in particle size and zeta potential of (a) the CS-γ-PGA nanoparticles (0.10% γ-PGA:0.20% CS) and (b) the CS-γ-PGA nanoparticles (0.10% γ-PGA:0.01% CS) during storage for up to 6 weeks.

Two representative groups of the prepared nanoparticles were selected for the stability study: one with a positive surface charge (0.10% γ-PGA:0.20% CS) and the other with a negative surface charge (0.10% γ-PGA:0.01% CS). FIG. 5 shows changes in particle size (■, mean diameter) and zeta potential (●) of (a) the CS-γ-PGA nanoparticles (0.10% γ-PGA:0.20% CS) and (b) the CS-γ-PGA nanoparticles (0.10% γ-PGA:0.01% CS) during storage up to 6 weeks. It was found that neither aggregation nor precipitation of nanoparticles was observed during storage up to 6 weeks, as a result of the electrostatic repulsion between the positively charged CS-γ-PGA nanoparticles (for the former group) and the negatively charged CS-γ-PGA nanoparticles (for the latter group).

Additionally, changes in particle size and zeta potential of the nanoparticles were minimal for both studied groups (FIGS. 5a and 5b). These results demonstrated that the prepared nanoparticles suspended in deionized water were stable during storage.

TABLE 1a

Effects of concentrations of γ-PGA and CS on the particle sizes of the prepared CS-γ-PGA nanoparticles
Mean Particle Size (nm, n = 5)

| γ-PGA | CS | | | | |
|---|---|---|---|---|---|
| | 0.01%[a] | 0.05% | 0.10% | 0.15% | 0.20% |
| 0.01%[b] | 79.0 ± 3.0 | 103.1 ± 4.6 | 96.7 ± 1.9 | 103.6 ± 1.9 | 140.5 ± 2.0 |
| 0.05% | 157.4 ± 1.7 | 120.8 ± 3.9 | 144.5 ± 2.4 | 106.2 ± 3.8 | 165.4 ± 1.7 |
| 0.10% | 202.2 ± 3.1 | 232.6 ± 1.2 | 161.0 ± 1.8 | 143.7 ± 2.7 | 218.1 ± 4.1 |

TABLE 1a-continued

Effects of concentrations of γ-PGA and CS on the particle sizes
of the prepared CS-γ-PGA nanoparticles
Mean Particle Size (nm, n = 5)

| | CS | | | | |
|---|---|---|---|---|---|
| γ-PGA | 0.01%[a] | 0.05% | 0.10% | 0.15% | 0.20% |
| 0.15% | 277.7 ± 3.2 | 264.9 ± 2.1 | 188.6 ± 2.9 | 178.0 ± 2.2 | 301.1 ± 6.4 |
| 0.20% | 284.1 ± 2.1 | 402.2 ± 4.0 | ▲ | 225.5 ± 3.1 | 365.5 ± 5.1 |

[a] concentration of CS (by w/v)
[b] concentration of γ-PGA (by w/v)
▲ precipitation of aggregates was observed TABLE 1b Effects of concentrations of γ-PGA and CS on the zeta potential values
of the prepared CS-γ-PGA nanoparticles.
Zeta Potential (mV, n = 5)

| | CS | | | | |
|---|---|---|---|---|---|
| γ-PGA | 0.01%[a] | 0.05% | 0.10% | 0.15% | 0.20% |
| 0.01%[b] | 15.4 ± 0.3 | 22.8 ± 0.5 | 19.8 ± 1.5 | 16.5 ± 1.4 | 17.2 ± 1.6 |
| 0.05% | −32.7 ± 0.7 | 23.7 ± 1.7 | 27.6 ± 0.7 | 20.3 ± 0.8 | 19.2 ± 0.6 |
| 0.10% | −33.1 ± 1.3 | 21.1 ± 1.6 | 20.3 ± 1.1 | 23.6 ± 0.9 | 24.7 ± 1.2 |
| 0.15% | −33.2 ± 2.1 | −21.9 ± 2.0 | 19.2 ± 0.4 | 16.9 ± 1.7 | 19.8 ± 0.3 |
| 0.20% | −34.5 ± 0.5 | −34.6 ± 0.3 | ▲ | 14.6 ± 0.7 | 16.3 ± 0.7 |

[a] concentration of CS (by w/v)
[b] concentration of γ-PGA (by w/v)
▲ precipitation of aggregates was observed In a further study, NPs were self-assembled instantaneously upon addition of an aqueous γ-PGA into an aqueous TMC (N-trimethyl chitosan) having a TMC/γ-PGA weight ratio of 6:1 under magnetic stirring at room temperature. Other chitosan derivative, such as mono-N-carboxymethyl chitosan (MCC), has also been useful in self-assembled nanoparticle formation. The chemical formulas of chitosan, N-trimethyl chitosan, and MCC are shown below:

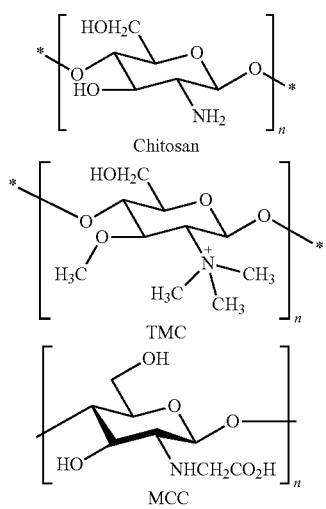

The amount of positively charged TMC significantly exceeded that of negatively charged γ-PGA; some of excessive TMC molecules were entangled onto the surfaces of NPs, thus displaying a positive surface charge (Table 2). The degree of quaternization on TMC had little effects on the mean particle size and zeta potential of NPs.

TABLE 2

Mean particle sizes, zeta potential values and polydispersity
indices of nanoparticles (NPs) self-assembled by TMC polymers
with different degrees of quaternization and γ-PGA
(n = 5 batches). TMC: N-trimethyl chitosan;
CS: chitosan; γ-PGA: poly(γ-glutamic acid).

| | Mean Particle Size (nm) | Zeta Potential (mV) | Polydispersity Index |
|---|---|---|---|
| CS/γ-PGA NPs | 104.1 ± 1.2 | 36.2 ± 2.5 | 0.11 ± 0.02 |
| TMC25/γ-PGA NPs | 101.3 ± 3.1 | 30.9 ± 2.1 | 0.13 ± 0.04 |
| TMC40/γ-PGA NPs | 106.3 ± 2.3 | 32.3 ± 2.1 | 0.15 ± 0.14 |
| TMC55/γ-PGA NPs | 114.6 ± 2.3 | 30.6 ± 3.8 | 0.12 ± 0.03 |

Example No. 4

Caco-2 Cell Cultures and TEER Measurements

Caco-2 cells were seeded on the tissue-culture-treated polycarbonate filters (diameter 24.5 mm, growth area 4.7 cm$^2$) in Costar Transwell 6 wells/plates (Corning Costar Corp., NY) at a seeding density of $3\times10^5$ cells/insert. MEM (pH 7.4) supplemented with 20% FBS, 1% NEAA, and 40 μg/ml antibiotic-gentamicin was used as the culture medium, and added to both the donor and acceptor compartments. The medium was replaced every 48 hours for the first 6 days and every 24 hours thereafter. The cultures were kept in an atmosphere of 95% air and 5% $CO_2$ at 37° C. and were used for the paracellular transport experiments 18-21 days after seeding (TEER values in the range of 600-800 Ωcm$^2$).

The intercellular tight junction is one of the major barriers to the paracellular transport of macromolecules (J. Control. Release 1996; 39:131-138; J. Control. Release 1998; 51:35-46). Trans-epithelial ion transport is contemplated to be a good indication of the tightness of the junctions between cells and therefore evaluated by measuring TEER of Caco-2 cell monolayers in the study. It was reported that the measurement of TEER can be used to predict the paracellular transport of hydrophilic molecules (Eur. J. Pharm. Biopharm. 2004; 58:225-235). When the tight junctions open, the TEER value will be reduced due to the water and ion passage through the paracellular route. Caco-2 cell monolayers have been widely used as an in vitro model to evaluate the intestinal paracellular permeability of macromolecules.

Figure 6:
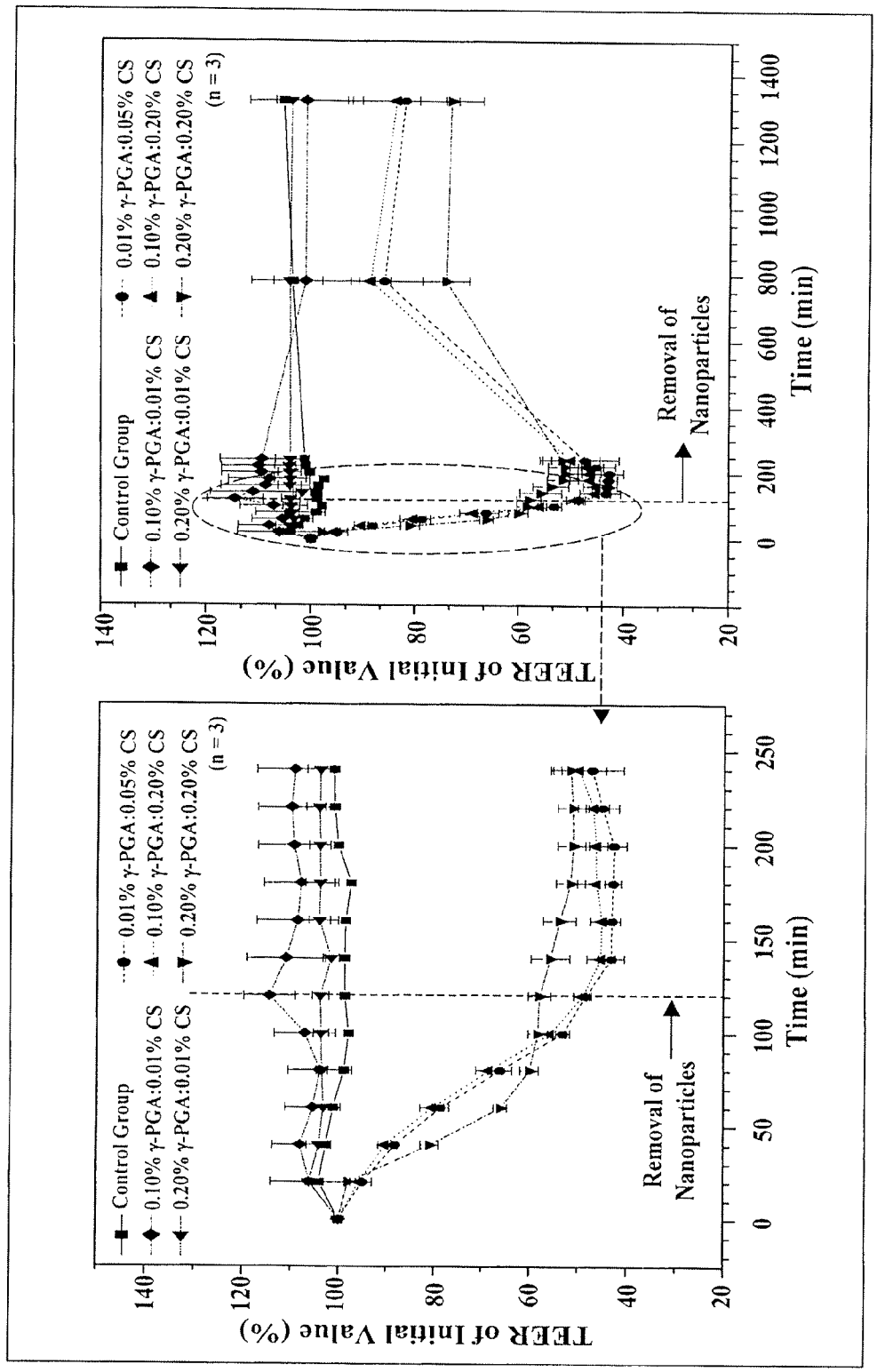
FIG. 6 shows effects of the prepared CS-γ-PGA nanoparticles on the TEER values of Caco-2 cell monolayers.

Effects of the prepared CS-γ-PGA nanoparticles on the TEER values of Caco-2 cell monolayers are shown in FIG. 6. As shown, the prepared nanoparticles with a positive surface charge (CS dominated on the surface, 0.01% γ-PGA:0.05% CS, 0.10% γ-PGA:0.2% CS, and 0.20% γ-PGA:0.20% CS) were able to reduce the values of TEER of Caco-2 cell monolayers significantly (p<0.05). After a 2-hour incubation with these nanoparticles, the TEER values of Caco-2 cell monolayers were reduced to about 50% of their initial values as compared to the control group (without addition of nanoparticles in the transport media). This indicated that the nanoparticles with CS dominated on the surfaces could effectively open or loosen the tight junctions between Caco-2 cells, resulting in a decrease in the TEER values. It was reported that interaction of the positively charged amino groups of CS with the negatively charged sites on cell surfaces and tight junctions induces a redistribution of F-actin and the tight junction's protein ZO-1, which accompanies the increased paracellular permeability (Drug Deliv. Rev. 2001; 50:S91-S101). It is suggested that an interaction between chitosan and the tight junction protein ZO-1, leads to its translocation to the cytoskeleton.

After removal of the incubated nanoparticles, a gradual increase in TEER values was noticed. This phenomenon indicated that the intercellular tight junctions of Caco-2 cell monolayers started to recover gradually; however, the TEER values did not recover to their initial values (FIG. 6). Kotzé et al. reported that complete removal of a CS-derived polymer, without damaging the cultured cells, was difficult due to the highly adhesive feature of CS (Pharm. Res. 1997; 14:1197-1202). This might be the reason why the TEER values did not recover to their initial values. In contrast, the TEER values of Caco-2 cell monolayers incubated with the nanoparticles with a negative surface charge (γ-PGA dominated on the surface, 0.10% γ-PGA:0.01% CS and 0.20% γ-PGA:0.01% CS, FIG. 6) showed no significant differences as compared to the control group (p>0.05). This indicated that γ-PGA does not have any effects on the opening of the intercellular tight junctions.

Figure 8:
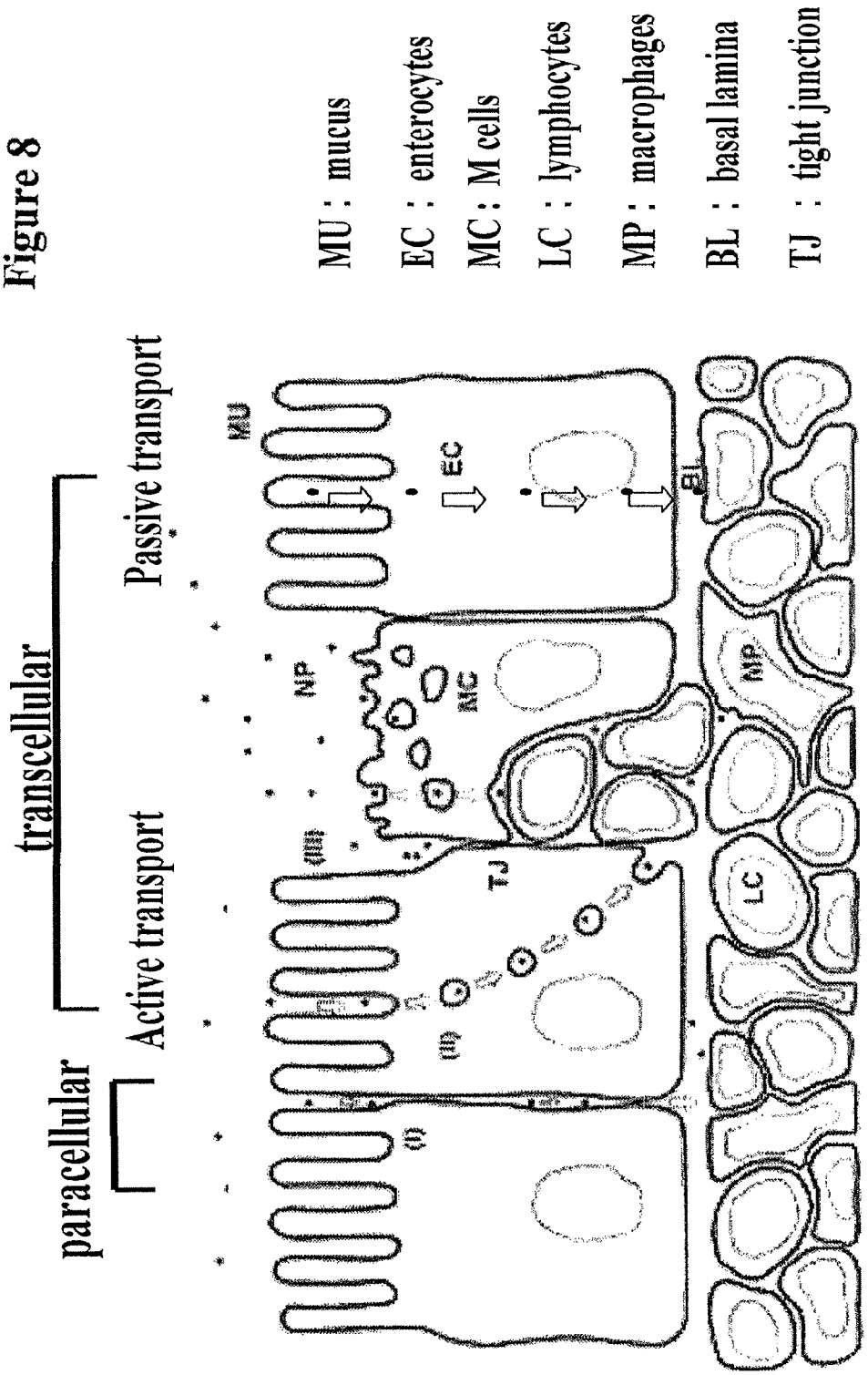
FIG. 8 shows an illustrative protein transport mechanism through a cell layer, including transcellular transport and paracelluler transport.
Figure 9:
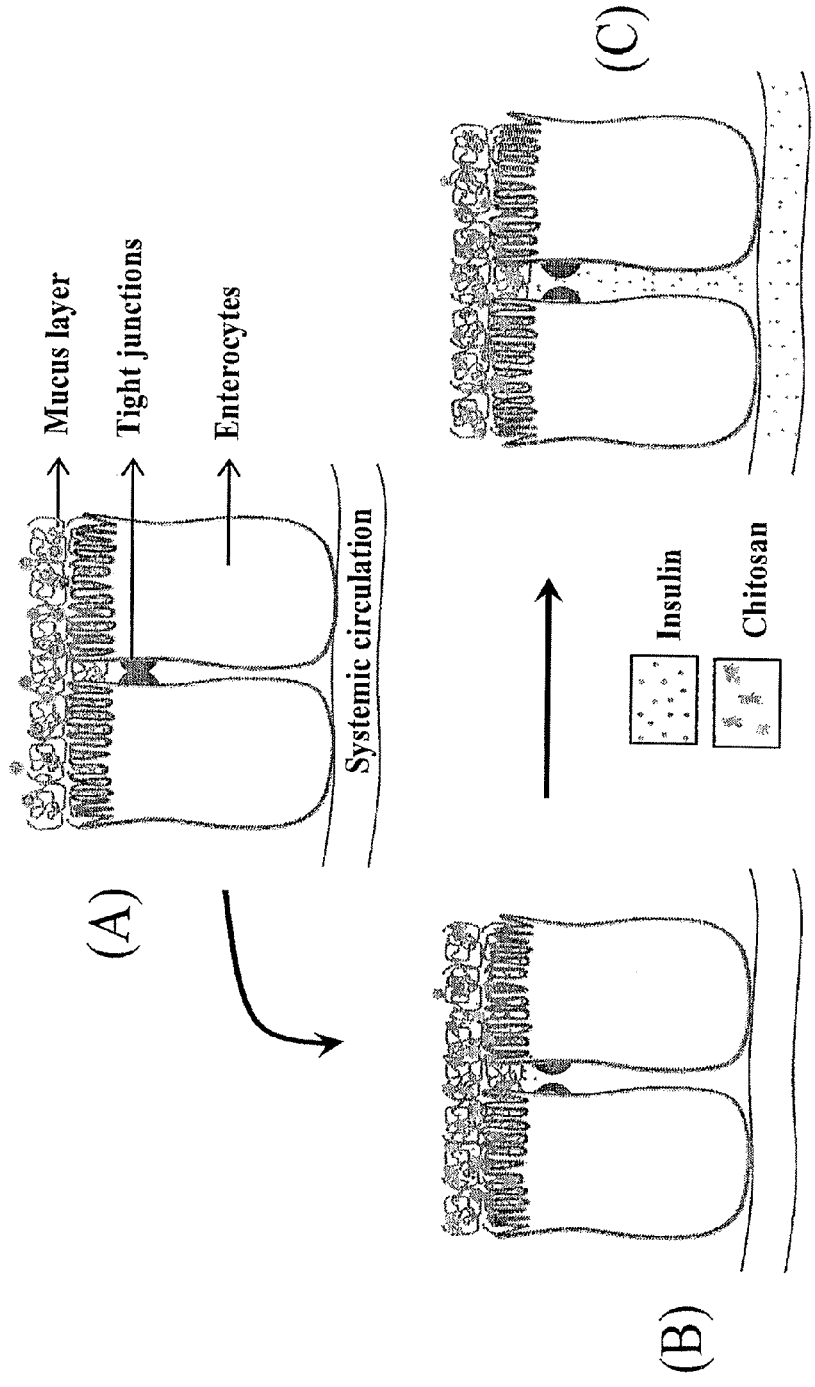
FIG. 9 A-C show a schematic illustration of a paracellular transport mechanism.

FIG. 8 shows an illustrative protein transport mechanism through a cellular layer, including transcellular transport and paracelluler transport. FIG. 9 shows a schematic illustration of a paracellular transport mechanism. The transcellular protein or peptide transport may be either an active transport or a passive transport mode whereas the paracellular transport is basically a passive mode. Ward et al. reported and reviewed current knowledge regarding the physiological regulation of tight junctions and paracellular permeability (PSTT 2000; 3:346-358). Chitosan as nanoparticle vehicles for oral delivery of protein drugs avoids the enzymatic inactivation in the gastrointestinal conduit. The chitosan component of the present nanoparticles has a special feature of adhering to the mucosal surface and transiently opening the tight junctions between epithelial cells; that is, loosening the tightness of the tight junctions.

FIG. 9(A) shows that after feeding nanoparticles (NPs) orally, NPs adhere and infiltrate into the mucus layer of the epithelial cells. FIG. 9(B) illustrates that the infiltrated NPs transiently and reversibly loosen tight junctions (TJs) while becoming unstable and disintegrated to release insulin or another entrapped agent. FIG. 9(c) shows that the released insulin or agent permeates through the paracellular pathway into the blood stream. Chitosan (CS), a nontoxic, soft-tissue compatible, cationic polysaccharide has special features of adhering to the mucosal surface; CS is able to transiently and reversibly widen/loosen TJs between epithelial cells. The TJ width in the small intestine has been demonstrated to be less than 1 nm. It is also known that TJs 'opened' by absorption enhancers are less than 20 nm wide (Nanotechnology 2007; 18:1-11). The term "opened" herein means that any substance less than 20 nm in the close-proximity might have the chance to pass through. TJs are the principal barrier to passive movement of fluid, electrolytes, macromolecules and cells through the paracellular pathway.

It was suggested that the electrostatic interaction between the positively charged CS and the negatively charged sites of ZO-1 proteins on cell surfaces at TJ induces a redistribution of cellular F-actin as well as ZO-1's translocation to the cytoskeleton, resulting in an increase in permeability. As evidenced in FIG. 9, after adhering and infiltrating into the mucus layer of the duodenum, the orally administered nanoparticles may degrade due to the presence of distinct digestive enzymes in the intestinal fluids. Additionally, the pH environment may become neutral while the nanoparticles were infiltrating into the mucosa layer and approaching the intestinal epithelial cells. This further leads to the collapse of nanoparticles due to the change in the exposed pH environment. The dissociated CS from the degraded/collapsed nanoparticles was then able to interact and modulate the function of ZO-1 proteins between epithelial cells (Nanotechnology 2007; 18:1-11). ZO-1 proteins are thought to be a linkage molecule between occludin and F-actin cytoskeleton as well as play important roles in the rearrangement of cell-cell contacts at TJs.

Example No. 5 fCS-γ-PGA Nanoparticle Preparation and CLSM Visualization

Fluorescence (FITC)-labeled CS-γ-PGA (fCS-γ-PGA) nanoparticles were prepared for the confocal laser scanning microscopy (CLSM) study. The nanoparticles of the present invention display a structure of a neutral polyelectrolyte-complex core surrounded by a positively charged chitosan shell. Synthesis of the FITC-labeled low-MW CS (fCS) was based on the reaction between the isothiocyanate group of FITC and the primary amino groups of CS as reported in the literature (Pharm. Res. 2003; 20:1812-1819). Briefly, 100 mg of FITC in 150 ml of dehydrated methanol were added to 100 ml of 1% low-MW CS in 0.1M acetic acid. After 3 hours of reaction in the dark at ambient conditions, fCS was precipitated by raising the pH to about 8-9 with 0.5M NaOH. To remove the unconjugated FITC, the precipitate was subjected to repeated cycles of washing and centrifugation (40,000×g for 10 min) until no fluorescence was detected in the supernatant. The fCS dissolved in 80 ml of 0.1M acetic acid, then dialyzed for 3 days in the dark against 5 liters of distilled water, with the water replaced on a daily basis. The resulting fCS was lyophilized in a freeze dryer. The fCS-γ-PGA nanoparticles were prepared as per the procedure described in Example No. 3.

Afterward, the transport medium containing fCS-γ-PGA nanoparticles (0.2 mg/ml) was introduced into the donor compartment of Caco-2 cells, which were pre-cultured on the transwell for 18-21 days. The experimental temperature was maintained at 37° C. by a temperature control system (DH-35 Culture Dish Heater, Warner Instruments Inc., Hamden, Conn.). After incubation at specific time intervals, test samples were aspirated. The cells were then washed twice with pre-warmed PBS solution before they were fixed in 3.7% paraformaldehyde (Pharm. Res. 2003; 20:1812-1819). Cells were examined under an inversed CLSM (TCS SL, Leica, Germany). The fluorescence images were observed using an argon laser (excitation at 488 nm, emission collected at a range of 510-540 nm).

Figure 7:
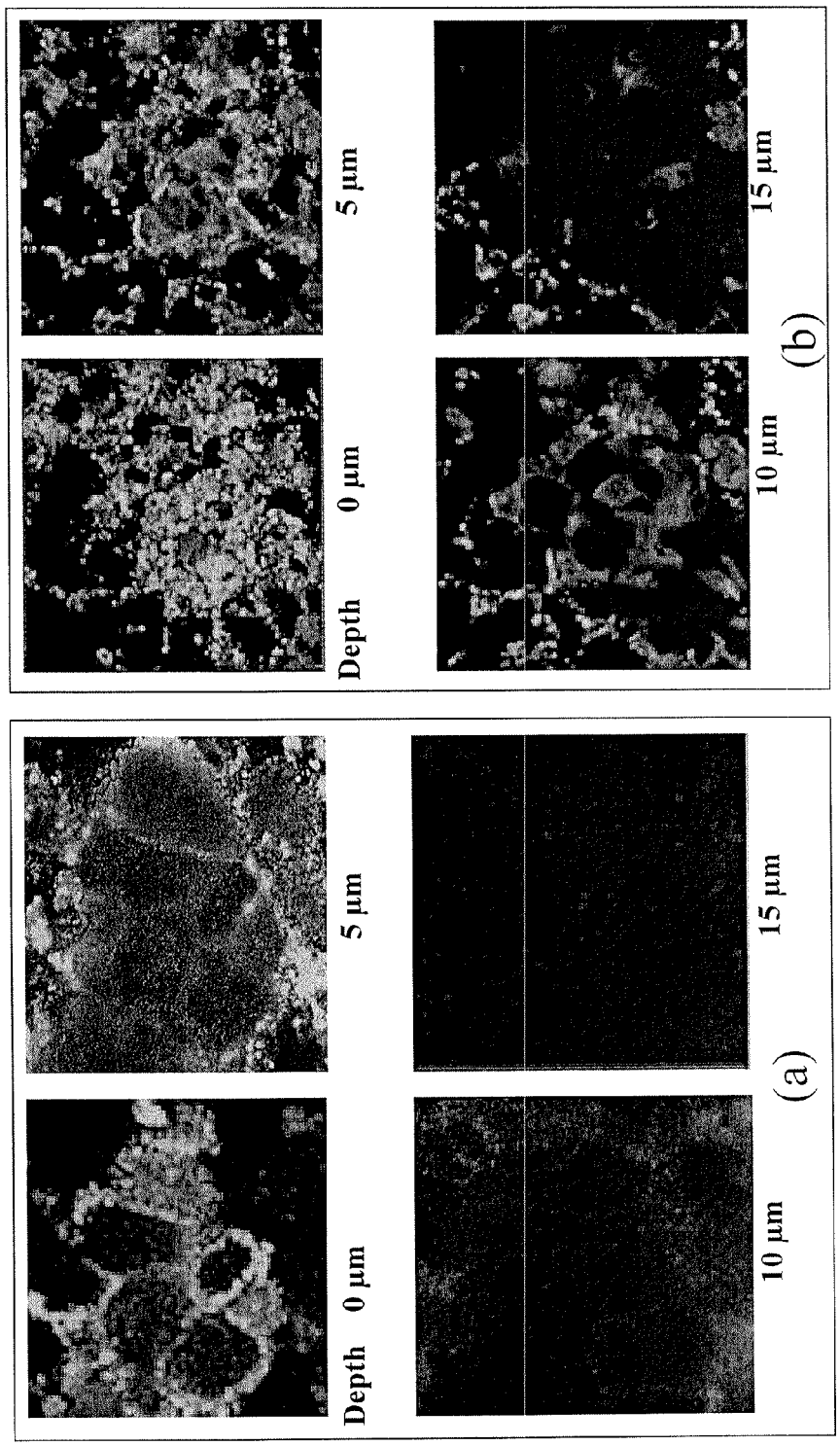
FIG. 7 shows fluorescence images (taken by an inversed confocal laser scanning microscope) of 4 optical sections of a Caco-2 cell monolayer that had been incubated with the fCS-γ-PGA nanoparticles with a positive surface charge (0.10% γ-PGA:0.20% CS) for (a) 20 min and (b) 60 min.

A CLSM was used to visualize the transport of the fluorescence-labeled CS-γ-PGA (fCS-γ-PGA) nanoparticles across the Caco-2 cell monolayers. This non-invasive method allows for optical sectioning and imaging of the transport pathways across the Caco-2 cell monolayers, without disrupting their structures (J. Control. Release 1996; 39:131-138). FIGS. 7a and 7b show the fluorescence images of 4 optical sections of a Caco-2 cell monolayer that had been incubated with the fCS-γ-PGA nanoparticles having a positive surface charge (0.10% γ-PGA:0.20% CS, zeta potential: about 21 mV) for 20 and 60 min, respectively. As shown, after 20 min of incubation with the nanoparticles, intense fluorescence signals at intercellular spaces were observed at depths of 0 and 5 μm from the apical (upper) surface of the cell monolayer. The intensity of fluorescence became weaker at levels deeper than 10 μm from the apical surface of the cell monolayer and was almost absent at depths 15 μm (FIG. 7a).

After 60 minutes of incubation with the nanoparticles, the intensity of the fluorescence observed at intercellular spaces was stronger and appeared at a deeper level than those observed at 20 min after incubation. These observations correlated with our TEER results, confirming that the nanoparticles with a positive surface charge (CS dominated on the surface) were able to open the tight junctions between Caco-2 cells and allow transport of the nanoparticles by passive diffusion via the paracellular pathways.

Example No. 6

In Vivo Study with Fluorescence-labeled Nanoparticles

Fluorescence (FITC)-labeled CS-γ-PGA (fCS-γ-PGA) nanoparticles were prepared for the confocal laser scanning microscopy (CLSM) study. After feeding rats with fCS-γ-PGA nanoparticles, the rats were sacrificed at a pre-determined time and the intestine isolated for CLSM examination. The fluorescence images of the nanoparticles that showed penetration through the mouse intestine at appropriate time and at various depths from the inner surface toward the exterior surface of the intestine, including duodenum, jejunum, and ileum were clearly observed by CLSM.

Example No. 7

Insulin Loading Capacity in Nanoparticles

Fluorescence (FITC)-labeled γ-PGA was added into the chitosan solution to prepare fluorescence (FITC)-labeled, insulin-loaded CS-γ-PGA nanoparticles for in vivo animal study with confocal laser scanning microscopy (CLSM) assessment and bioactivity analysis. The insulin-loaded CS-γPGA nanoparticles are prepared by using the ionic-gelation method upon addition of insulin mixed with γ-PGA solution into CS solution, followed by magnetic stirring in a container.

Model insulin used in the experiment and disclosed herein is obtained from bovine pancreas (Sigma-Aldrich, St. Louis, Mo.), having a molecular formula of $C_{254}H_{377}N_{65}O_{75}S6$ with a molecular weight of about 5733.5 and an activity of ≧27 USP units/mg. The insulin contains a two-chain polypeptide hormone produced by the β-cells of pancreatic islets. The α and β chains are joined by two interchain disulfide bonds. Insulin regulates the cellular uptake, utilization, and storage of glucose, amino acids, and fatty acids as well as inhibits the breakdown of glycogen, protein, and fat. The insulin from Sigma-Aldrich contains about 0.5% zinc. Separately, insulin can be obtained from other sources, such as a human insulin solution that is chemically defined, recombinant from *Saccharomyces cerevisiae*. Some aspects of the invention relate to nanoparticles with insulin in the core, wherein the insulin may contain intermediate-acting, regular insulin, rapid-acting insulin, sustained-acting insulin that provides slower onset and longer duration of activity than regular insulin, or combinations thereof.

Examples of insulin or insulin analog products include, but not limited to, Humulin® (by Eli Lilly), Humalog® (by Eli Lilly) and Lantus® (by Aventis), and Novolog® Mix70/30 (by Novo Nordisk). Humalog (insulin lispro, rDNA origin) is a human insulin analog that is a rapid-acting, parenteral blood glucose-lowering agent. Chemically, it is Lys(B28), Pro(B29) human insulin analog, created when the amino acids at positions 28 and 29 on the insulin B-chain are reversed. Humalog is synthesized with a special non-pathogenic laboratory strain of *Escherichia coli* bacteria that has been genetically altered by the addition of the gene for insulin lispro. Humalog has the empirical formula $C_{257}H_{383}N_{65}O_{77}S_6$ and a molecular weight of 5808, identical to that of human insulin. The vials and cartridges contain a sterile solution of Humalog for use as an injection. Humalog injection consists of zinc-insulin lispro crystals dissolved in a clear aqueous fluid. Each milliliter of Humalog injection contains insulin lispro 100 Units, 16 mg glycerin, 1.88 mg dibasic sodium phosphate, 3.15 mg m-cresol, zinc oxide content adjusted to provide 0.0197 mg zinc ion, trace amounts of phenol, and water for injection. Insulin lispro has a pH of 7.0-7.8. Hydrochloric acid 10% and/or sodium hydroxide 10% may be added to adjust pH.

Humulin is used by more than 4 million people with diabetes around the world every day. Despite its name, this insulin does not come from human beings. It is identical in chemical structure to human insulin and is manufactured in a factory using a chemical process called recombinant DNA technology. Humulin L is an amorphous and crystalline suspension of human insulin with a slower onset and a longer duration of activity (up to 24 hours) than regular insulin. Humulin U is a crystalline suspension of human insulin with zinc providing a slower onset and a longer and less intense duration of activity (up to 28 hours) compared to regular insulin or the intermediate-acting insulins (NPH and Lente).

LANTUS® (insulin glargine [rDNA origin] injection) is a sterile solution of insulin glargine for use as an injection. Insulin glargine is a recombinant human insulin analog that is a long-acting (up to 24-hour duration of action), parenteral blood-glucose-lowering agent. LANTUS is produced by recombinant DNA technology utilizing a non-pathogenic laboratory strain of *Escherichia coli* (K12) as the production organism. Insulin glargine differs from human insulin in that the amino acid asparagine at position A21 is replaced by glycine and two arginines are added to the C-terminus of the B-chain. Chemically, it is $21^A$-Gly-$30^B$a-L-Arg-$30^B$b-L-Arg-human insulin and has the empirical formula $C_{267}H_{404}N_{72}O_{78}S_6$ with a molecular weight of 6063.

LANTUS consists of insulin glargine dissolved in a clear aqueous fluid. Each milliliter of LANTUS (insulin glargine injection) contains 100 IU (3.6378 mg) insulin glargine. Inactive ingredients for the 10 mL vial are 30 mcg zinc, 2.7 mg m-cresol, 20 mg glycerol 85%, 20 mcg polysorbate 20, and water for injection. Inactive ingredients for the 3 mL cartridge are 30 mcg zinc, 2.7 mg m-cresol, 20 mg glycerol 85%, and water for injection. In 2006, there were 11.4 million prescriptions of Lantus in the U.S. for basal insulin maintenance.

Novolog® Mix70/30 (70% insulin aspart protamine suspension and 30% insulin aspart injection [rDNA origin]) is a human insulin analog suspension. Novolog® Mix70/30 is a blood glucose-lowering agent with a rapid onset and an intermediate duration of action. Insulin aspart is homologous with regular human insulin with the exception of a single substitution of the amino acid praline by aspartic acid in position B28, and is produced by recombinant DNA technology utilizing *Saccharomyces cerevisiae* as the production organism. Insulin aspart (Novolog) has the empirical formula C256H381N65O79S6 and a molecular weight of 5826. Novolog® Mix70/30 is a uniform, white sterile suspension that contains zinc 19.6 μg/ml and other components.

The nanoparticles with two insulin concentrations are prepared at a chitosan to γ-PGA ratio of 0.75 mg/ml to 0.167 mg/ml. Their particle size and zeta potential are shown in Table 3 below.

TABLE 3

| Insulin Conc. (mg/ml) (n = 5) | Mean Particle Size (nm) | Polydispersity Index (PI) | Zeta Potential (mV) |
|---|---|---|---|
| 0* | 145.6 ± 1.9 | 0.14 ± 0.01 | +32.11 ± 1.61 |
| 0.042 | 185.1 ± 5.6 | 0.31 ± 0.05 | +29.91 ± 1.02 |
| 0.083 | 198.4 ± 6.2 | 0.30 ± 0.09 | +27.83 ± 1.22 |

(*) control reference without insulin

Figure 11:
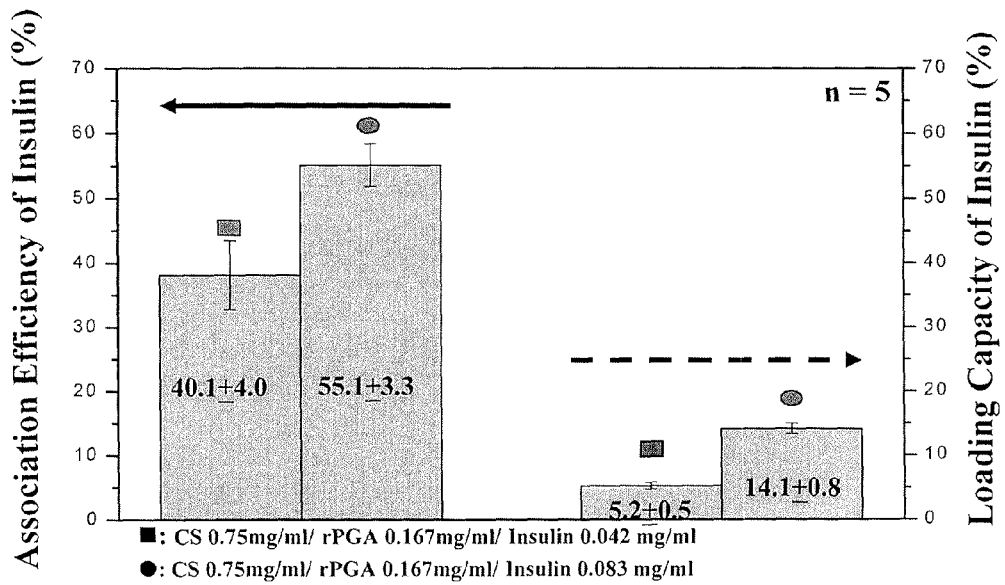
FIG. 11 shows loading capacity and association efficiency of insulin in nanoparticles of chitosan and γ-PGA.
Figure 12:
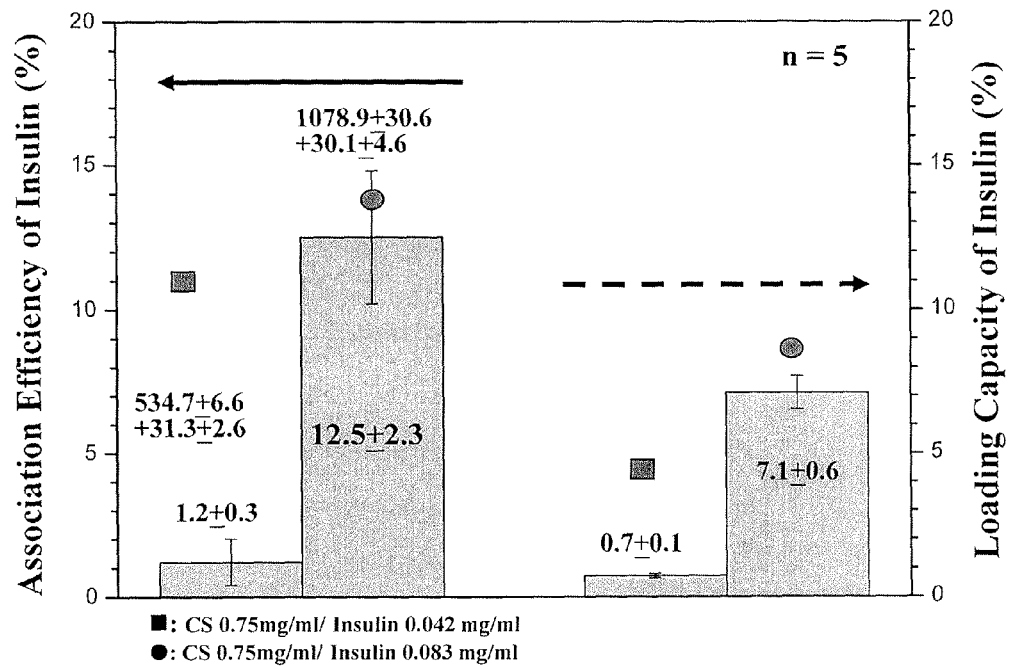
FIG. 12 shows loading capacity and association efficiency of insulin in nanoparticles of chitosan as reference.

Further, their association efficiency of insulin and loading capacity of insulin are analyzed, calculated and shown in FIGS. 11 and 12, according to the following formula:

$$\text{Insulin Association Efficiency } (LE\%) = \frac{(\text{Total amount of insulin} - \text{Insulin in supernatant})}{\text{Total amount of insulin}} \times 100\%$$

$$\text{Loading Capacity } (LC) = \frac{(\text{Total amount of insulin} - \text{Insulin in supernatant})}{\text{Weight of recovered particles}} \times 100\%$$

FIG. 11 shows loading capacity and association efficiency of insulin in nanoparticles of chitosan and γ-PGA, whereas FIG. 12 shows loading capacity and association efficiency of insulin in nanoparticles of chitosan alone (in absence of γ-PGA) as reference. The data clearly demonstrates that both the insulin loading capacity and insulin association efficiency are statistically higher for the nanoparticles with γ-PGA in the core. The LE (40~55%) and LC (5.0~14.0%) of insulin for CS-γPGA nanoparticles were obtained by using the ionic-gelation method upon addition of insulin mixed with γ-PGA solution into CS solution, followed by magnetic stirring for nanoparticle separation.

In certain follow-up experiments, nanoparticles having a pharmaceutical composition have been successfully prepared with a negatively charged component comprised of γ-PGA, α-PGA, PGA derivatives, salts of PGA, heparin or heparin analog, glycosaminoglycans, or alginate. The PGA derivatives of the present invention may include, but are not limited to, poly-γ-glutamic acid, poly-α-glutamic acid, poly-L-glutamic acid (manufactured by Sigma-Aldrich, St. Louis, Mo.), poly-D-glutamic acid, poly-L-α-glutamic acid, poly-γ-D-glutamic acid, poly-γ-DL-glutamic acid, and PEG or PHEG derivatives of polyglutamic acid, salts of the above-cited PGAs, and the like. Some aspects of the invention relate to nanoparticles comprising a shell component and a core component, wherein at least a portion of the shell component comprises chitosan and wherein the core component is comprised of a negatively charged compound that is conjugated to chitosan, and a bioactive agent. Some aspects of the invention relate to an oral dose of nanoparticles that effectively enhance epithelial permeation (such as intestinal or blood brain paracellular transport) comprising a negative component (such as γ-PGA, α-PGA, PGA derivatives, heparin, or alginate) in the core and low molecular weight chitosan, wherein the chitosan dominates on a surface of the nanoparticles with positive charges.

Some aspects of the invention relate to a dose of nanoparticles that effectively enhance epithelial permeation, intestinal transport or blood brain paracellular transport comprising a polyanionic component (such as γ-PGA, α-PGA, PGA derivatives, heparin, heparin analogs, low molecular weight heparin, glycosaminoglycans, or alginate) in the core and low molecular weight chitosan in the shell, wherein the chitosan dominates on the surface of the nanoparticles with positive surface charges. In practice, the Alzheimer's drug is encapsulated in the chitosan shell nanoparticle as described herein, wherein the nanoparticle is partially crosslinked (optionally) to enhance its biodurability. Then, the nanoparticles are intravenously injected, whereby the nanoparticles pass to the brain in blood circulation. The chitosan shell of the nanoparticles adheres to the surface adjacent the tight junction in the brain. Thereafter, the chitosan nanoparticle opens the tight junction, wherein the Alzheimer's drug is released for therapeutic treatment after passing the tight junction. In one embodiment, the nanoparticles are in a spherical shape having a mean particle size of about 50 to 250 nanometers, preferably 150 nanometers to 250 nanometers.

Dalteparin is a low molecular weight heparin. It is marketed as Fragmin® by Pfizer Inc. Like other low molecular weight heparins, dalteparin is used for prophylaxis or treatment of deep vein thrombosis and pulmonary embolism. The CLOT study, published in 2003, showed that in patients with malignancy and acute venous thromboembolism, dalteparin was more effective than Coumadin in reducing the risk of recurrent embolic events. Dalteparin is the only low molecular weight heparin shown to be safe in critically ill people with renal failure. Heparins are cleared by the kidneys, but studies have shown that dalteparin does not accumulate even if kidney function is reduced.

In one example, intravenous administration of the nanoparticles comprising chitosan shell substrate, polyanionic core substrate and at least one bioactive agent for treating Alzheimer's disease in an animal subject is typically performed with 10 mg to 40 mg of active agent per day over a period of one month to one year. The bioactive agent is selected from the group consisting of donepezile, rivastigmine, galantamine, and/or those trade-named products, such as memantine hydrochloride (Axura® by Merz Pharmaceuticals), donepezil hydrochloride (Aricept® by Eisai Co. Ltd.), rivastigmine tartrate (Exelon® by Novartis), galantamine hydrochloride (Reminyl® by Johnson & Johnson), and tacrine hydrochloride (Cognex® by Parke Davis).

Some aspects of the invention relate to a nanoparticle with a core substrate comprising polyglutamic acids such as water soluble salt of polyglutamic acids (for example, ammonium salt) or metal salts of polyglutamic acid (for example, lithium salt, sodium salt, potassium salt, magnesium salt, and the like). In one embodiment, the polyglutamic acid may be selected from the group consisting of poly-α-glutamic acid, poly-L-α-glutamic acid, poly-γ-glutamic acid, poly-D-glutamic acid, poly-γ-D-glutamic acid, poly-γ-DL-glutamic acid, poly-L-glutamic acid (manufactured by Sigma-Aldrich, St. Louis, Mo.), and PEG or PHEG derivatives of polyglutamic acid. Alginate is generally non-biodegradable; however, it is stipulated that an alginate particle with about 30-50 kDa molecular weight is kidney inert. Heparin with negatively charged side-groups has a general chemical structure as shown below:

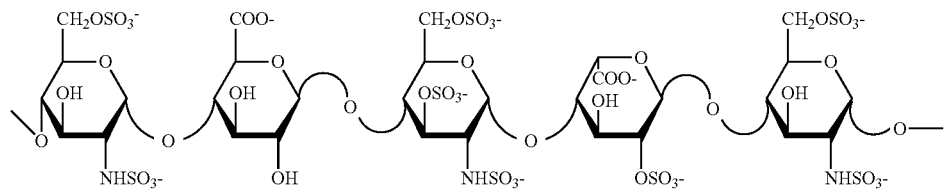

Some aspects of the invention relate to the negatively charged glycosaminoglycans (GAGs) as the core substrate of the present nanoparticles. GAGs may be complexed with a low-molecular-weight chitosan to form drug-carrier nanoparticles. GAGs may also conjugate with the protein drugs as disclosed herein to enhance the bonding efficiency of the core substrate in the nanoparticles. Particularly, the negatively charged core substrate (such as GAGs, heparin, PGA, alginate, and the like) of the nanoparticles of the present invention may conjugate with chondroitin sulfate, hyaluronic acid, PDGF-BB, BSA, EGF, MK, VEGF, KGF, bFGF, aFGF, MK, PTN, etc.

Anti-Diabetic Drugs

The anti-diabetic drugs are broadly categorized herein as insulin/insulin analogs and non-insulin anti-diabetic drugs. The non-insulin anti-diabetic drugs may include, but not limited to, insulin sensitizers, such as biguanides (for example, metformin, buformin, phenformin, and the like), thiazolidinedione (TZDs; for example, pioglitazone, rivoglitazone, rosiglitazone, troglitazone, and the like), and dual PPAR agonists (for example aleglitazar, muraglitazar, tesaglitazar, and the like; PPAR is abbreviation for peroxisome proliferator-activated receptor). The non-insulin anti-diabetic drugs may also include, but not limited to, secretagogues, such as sulfonylureas (for example, carbutamide, chloropamide, gliclazide, tolbutamide, tolazamide, glipizide, glibenclamide, gliquidone, glyclopyramide, glimepiride, and the like), meglitinides (for example, nateglinide, repaglinide, mitiglinide, and the like), GLP-1 analogs (for example, exenatide, liraglutide, albiglutide, taspoglutide, and the like), and DPP-4 inhibitors (for example, alogliptin, linagliptin, saxagliptin, sitagliptin, vildagliptin, and the like; DPP-4 is abbreviation for inhibitor of dipeptidyl peptidase 4). Further, the non-insulin anti-diabetic drugs may include, but not limited to, alpha-glucosidase inhibitors (for example, acarbose, miglitol, voglibose, and the like), amylin analog (for example, pramlintide and the like), SGLT2 inhibitor (for example, dapagliflozin, remogliflozin, sergliflozin, and the like), benfluorex, and tolrestat. Here, The sodium-glucose co-transporter type 2 (SGLT2) is a 672 amino acid high-capacity low-affinity transporter expressed in the S1 segment of the proximal tubule which is believed to mediate the majority of renal glucose reabsorption.

Glucagon, a hormone secreted by the pancreas, raises blood glucose levels. Its effect is opposite that of insulin, which lowers blood glucose levels. The pancreas releases glucagon when blood sugar (glucose) levels fall too low. Glucagon causes the liver to convert stored glycogen into glucose, which is released into the bloodstream. Glucagon also stimulates the release of insulin, so glucose can be taken up and used by insulin-dependent tissues. Thus, glucagon and insulin are part of a feedback system that keeps blood glucose levels at a stable level. Glucagon belongs to a family of several other related hormones. In one embodiment, the first bioactive agent (for example, glucagon) of the present invention is compatible with the second bioactive agent (for example, insulin), wherein glucagon stimulates the release of insulin, so glucose can be taken up and used by insulin-dependent tissues, when both are co-administered to an animal subject. Thus, glucagon and insulin are part of a feedback system that keeps blood glucose levels at a stable level.

Clinical data have shown enhanced anti-diabetic efficiency (or glycemic control) in an animal subject by co-administering two different anti-diabetic drugs; for example, exenatide has been approved to be co-administered along with metformin, or a combination of metformin and a sulfonyurea, or thiazolidinediones (such as pioglitazone or rosiglitazone). In cholesterol management clinical trials, it was reported that the combination of bezafibrate and diffunisol produced better clinical data than bezafibrate alone. Bezafibrate (marketed as Bezalip and various other brand names) is a fibrate drug used for the treatment of hyperlipidaemia. It helps to lower LDL cholesterol and triglyceride in the blood, and increase HDL.

Some aspects of the invention relate to a therapeutic method of treating a subject by co-administering at least two nanoparticle compositions, the first nanoparticle composition of the present invention comprising a first bioactive agent, wherein the second nanoparticle composition of the present invention comprises a second bioactive agent that is different from the first bioactive agent. In one example, the first bioactive agent is exenatide in the first nanoparticles and the second bioactive agent is metformin in the second nanoparticles. In one embodiment, the delivery route of administering the first nanoparticle composition is different from the delivery route of administering the second of the at least two nanoparticle compositions. In one embodiment, both types of first and second nanoparticles are loaded in the same capsules. In another embodiment, the first nanoparticles and the second nanoparticles are loaded in separate different capsules. In a further embodiment, the first bioactive agent is compatible with the second bioactive agent and optionally, the first bioactive agent enhances the therapeutic effects of the second bioactive agent when they are co-administered to the subject.

Some aspects of the invention relate to a system of pharmaceutical composition comprising two distinct types of bioactive nanoparticles, wherein the first type of bioactive nanoparticles comprises a shell portion that is dominated by positively charged chitosan, a core portion that contains negatively charged substrate, wherein the negatively charged substrate is at least partially neutralized with a portion of the positively charged chitosan and at least a first bioactive agent, and wherein the second type of bioactive nanoparticles comprises a shell portion that is dominated by positively charged chitosan, a core portion that contains negatively charged substrate, wherein the negatively charged substrate is at least partially neutralized with a portion of the positively charged chitosan and at least a second bioactive agent. In one embodiment, both types of the first and second nanoparticles are loaded in the same capsules for administering to a subject. In another embodiment, the first type of nanoparticles and the second type of nanoparticles are loaded in separate different capsules in the system for co-administering to a subject.

Calceti et al. reported an in vivo evaluation of an oral insulin-PEG delivery system (Eur J Pharma Sci 2004; 22:315-323). Insulin-PEG was formulated into mucoadhesive tablets constituted by the thiolated polymer poly(acrylic acid)-cysteine. The therapeutic agent was released from these tablets within 5 hours in a sustained manner. In vivo, by oral administration to diabetic mice, the glucose levels were found to decrease significantly over the time. Further, Krauland et al. reported another oral insulin delivery study of thiolated chitosan-insulin tablets on non-diabetic rats (J. Control. Release 2004, 95:547-555). The delivery tablets utilized 2-Iminothiolane covalently linked to chitosan to form chitosan-TBA (chitosan-4-thiobutylamidine) conjugate. After oral administration of chitosan-TBA-insulin tablets to non-diabetic conscious rats, the blood glucose level decreased significantly for 24 hours; supporting the expected sustained insulin release of the presently disclosed nanoparticles herein through intestinal absorption. In a further report by Morcol et al. (Int. J. Pharm. 2004; 277:91-97), an oral delivery system comprising calcium phosphate-PEG-insulin-casein particles displays a prolonged hypoglycemic effect after oral administration to diabetic rats.

Pan et al. disclosed that chitosan nanoparticles improving the intestinal absorption of insulin in vivo (Int J Pharma 2002; 249:139-147) with insulin-chitosan nanoparticles at a particle size of 250-400 nm, a polydispersity index smaller than 0.1, positively charged and stable. After administering the insulin-chitosan nanoparticles, it was found that the hypoglycemic effect was prolonged with enhanced pharmacological bioavailability. Their data confirmed our observation as shown in FIGS. 11 and 12; however, the insulin loading capacity and insulin association efficiency of the present invention are substantially higher for the chitosan-insulin nanoparticles with γ-PGA in the core as the core substrate.

Example No. 8

Nanoparticle Stability

Figure 13:
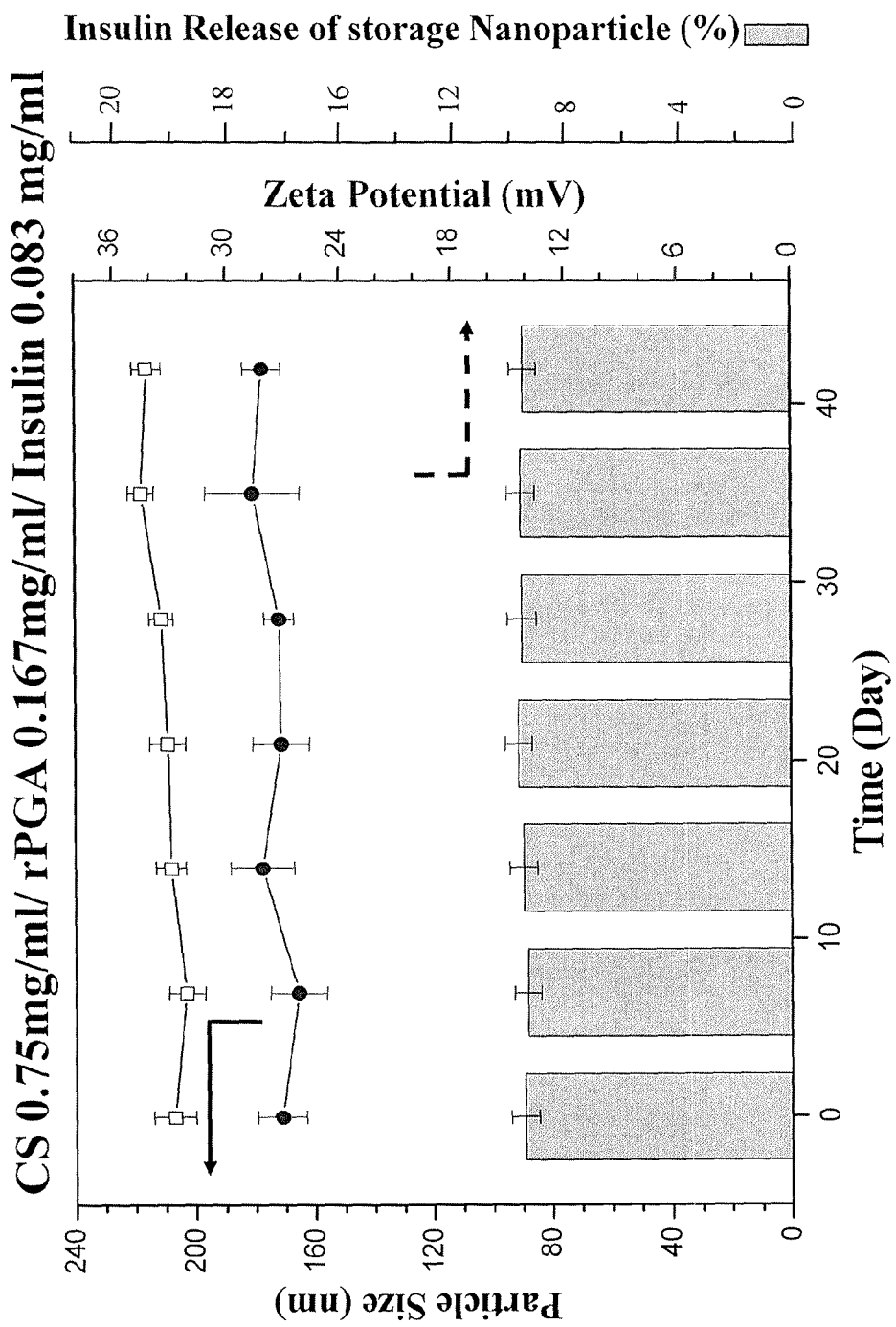
FIG. 13 shows the stability of insulin-loaded nanoparticles.

FIG. 13 shows the stability of insulin-loaded nanoparticles of the present invention with an exemplary composition of CS 0.75 mg/ml, γ-PGA 0.167 mg/ml, and insulin 0.083 mg/ml. The prepared insulin-loaded nanoparticles suspended in deionized water are stable during storage up to 40 days. First (in FIG. 13), the insulin content in the nanoparticle storage solution maintains at about a constant level of 9.5%. The nanoparticle stability is further evidenced by the substantially constant particle size at about 200 nm and substantially constant zeta potential of about +28 mV over the period of about 40 days. It is contemplated that the insulin-containing nanoparticles of the present invention would further maintain their biostability when formulated in a soft gelcap or capsule configuration that further isolates the nanoparticles from environmental effects, such as sunlight, heat, air conditions, and the like. Some aspects of the invention provide a gelcap pill or capsule containing a dosage of insulin nanoparticles effective amount of the insulin to treat or manage the diabetic animal subjects, wherein the stability of the insulin-containing nanoparticles is at least 40 days, preferably more than 6 months, and most preferably more than a couple of years.

By "effective amount of the insulin", it is meant that a sufficient amount of insulin will be present in the dose to provide for a desired therapeutic, prophylatic, or other biological effect when the compositions are administered to a host in single dosage forms. The capsule of the present invention may preferably comprise two-part telescoping gelatin capsules. Basically, the capsules are made in two parts by dipping metal rods in molten gelatin solution. The capsules are supplied as closed units to the pharmaceutical manufacturer. Before use, the two halve's are separated, the capsule is filled with powder (either by placing a compressed slug of powder into one half of the capsule, or by filling one half of the capsule with loose powder) and the other half of the capsule is pressed on. The advantage of inserting a slug of compressed powder is that there is a superior control of weight variation. The capsules may be enterically coated before filling the powder or after securing both parts of the filled capsule together. In one embodiment, the capsules further comprise a permeation enhancer, wherein the permeation enhancer is selected from the group consisting of $Ca^{2+}$ chelators, bile salts, anionic surfactants, medium-chain fatty acids, phosphate esters, chitosan, and chitosan derivatives.

In another embodiment, the capsule may contain solubilizer, bubbling agent, emulsifier, or other pharmacopoeial excipients, such as Generally Recognized as Safe (GRAS). GRAS is a United States of America Food and Drug Administration (FDA) designation that a chemical or substance added to food is considered safe by experts, and therefore exempted from the usual Federal Food, Drug, and Cosmetic Act (FFDCA) food additive tolerance requirements. The bubbling agent is the agent that emits carbon dioxide gas when contacting liquid with a purpose to burst the capsule or promote intimate contact of the capsule content with the surrounding material outside of the capsule. For example, reaction of sodium bicarbonate and an acid to give a salt and carbonic acid, which readily decomposes to carbon dioxide and water. The bubbling agent may include sodium bicarbonate/citric acid mixture, Ac-Di-Sol, and the like. The chemical Ac-Di-Sol has the IUPAC name of acetic acid, 2,3,4,5,6-pentahydroxyhexanal, sodium and a chemical formula of $C_8H_{16}NaO_8$. An emulsifier is a substance that stabilizes an emulsion by increasing its kinetic stability. One class of emulsifiers is known as surface active substances, or surfactants. Detergents are another class of surfactant emulsifier, and will physically interact with both oil and water, thus stabilizing the interface between oil or water droplets in suspension. The most popular emulsions are non-ionic because they have low toxicity. Cationic emulsions may also be used herein because their antimicrobial properties.

Thus, for convenient and effective oral administration, pharmaceutically effective amounts of the nanoparticles of this invention can be tabletted with one or more excipient, encased in capsules such as gel capsules, or suspended in a liquid solution and the like. The nanoparticles can be suspended in a deionized solution or a similar solution for parenteral administration. The nanoparticles may be formed into a packed mass for ingestion by conventional techniques. For instance, the nanoparticles may be encapsulated as a "hard-filled capsule" or a "soft-elastic capsule" using known encapsulating procedures and materials. The encapsulating material should be highly soluble in gastric fluid so that the particles would be rapidly dispersed in the stomach after the capsule is ingested. Each unit dose, whether capsule or tablet, will preferably contain nanoparticles of a suitable size and quantity that provides pharmaceutically effective amounts of the nanoparticles. The applicable shapes and sizes of capsules may include round, oval, oblong, tube or suppository shape with sizes from 0.75 mm to 80 mm or larger. The volume of the capsules can be from 0.05 cc to more than 5 cc. In one embodiment, the interior of capsules is treated to be hydrophobic or lipophilic.

Example No. 9

In Vitro Insulin Release Study

Figure 14:
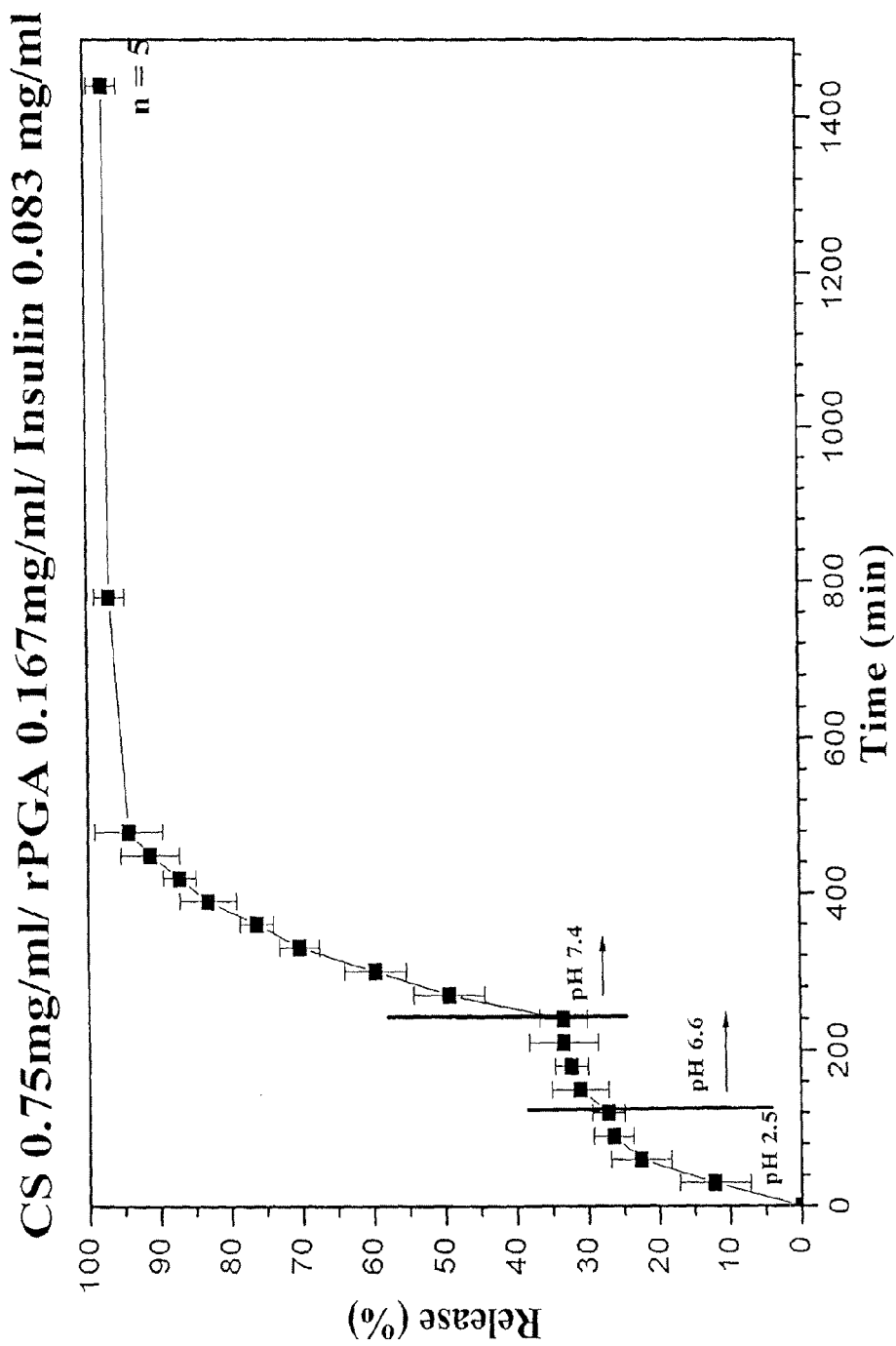
FIG. 14 shows a representative in vitro study with insulin drug release profile in a pH-adjusted solution.

FIG. 14 show a representative protein drug (for example, insulin) release profile in a pH-adjusted solution for pH-sensitivity study with an exemplary composition of CS 0.75 mg/ml, γ-PGA 0.167 mg/ml, and insulin 0.083 mg/ml in nanoparticles. In one embodiment, the exemplary composition may include each component at a concentration range of ±10% as follows: CS 0.75 mg/ml (a concentration range of 0.67 to 0.83 mg/ml), γ-PGA 0.167 mg/ml (a concentration range of 0.150 to 0.184 mg/ml), and insulin 0.083 mg/ml (a concentration range of 0.075 to 0.091 mg/ml). First, solution of the insulin-loaded nanoparticles was adjusted to pH 2.5 to simulate the gastric environment in a DISTEK-2230A container at 37° C. and 100 rpm. Samples (n=5) were taken at a pre-determined particular time interval and the particle-free solution was obtained by centrifuging at 22,000 rpm for 30 minutes to analyze the free or released insulin in solution by HPLC. Until the free insulin content in the sample solution approaches about constant of 26% (shown in FIG. 14), the pH was adjusted to 6.6 to simulate the entrance portion of the intestine. The net released insulin during this particular time interval is about (from 26% to 33%) 7%. In other words, the nanoparticles are quite stable (evidenced by minimal measurable insulin in solution) for both the pH 2.5 and pH 6.6 regions.

To simulate the exit portion of the intestine, the insulin-containing nanoparticle solution was adjusted to pH 7.4. The remaining insulin (about 67%) was released from the nanoparticles at this time. As discussed above, the insulin in nanoparticles would be more effective to penetrate the intestine wall in paracellular transport mode than the free insulin because of the present invention of the nanoparticles with chitosan at the outer surface (preferential mucosal adhesion on the intestinal wall) and positive charge (enhancing paracellular tight junction transport).

Since chitosan-shelled nanoparticles exhibit positive surface charge and preferential mucoadhesive properties (both are required for enhancing paracellular permeation), some aspects of the invention relate to a method of coating a nanoparticle (for example, a nanoparticle with little or no chitosan) with chitosan solution, resulting in a chitosan-shelled nanoparticle with positive surface charge.

Example No. 10

In Vivo Study with Insulin-Loaded Fluorescence-Labeled Nanoparticles

In the in vivo study, rats were injected with streptozotocin (STZ 75 mg/kg intraperitoneal) in 0.01M citrate buffer (pH 4.3) to induce diabetes. The blood from the rat's tail was analyzed with a commercially available glucometer for blood glucose. The blood glucose level on Wistar male rats at no fasting (n=5) was measured at 107.2±8.1 mg/dL for normal rats while the blood glucose level was at 469.7±34.2 mg/dL for diabetic rats. In the animal study, diabetic rats were fasting for 12 hours and subjected to four different conditions: (a) oral deionized water (DI) administration; (b) oral insulin administration at 30 U/kg; (c) oral insulin-loaded nanoparticles administration at 30 U/kg; and (d) subcutaneous (SC) insulin injection at 5 U/kg as positive control. The blood glucose concentration from rat's tail was measured over the time in the study.

Figure 15:
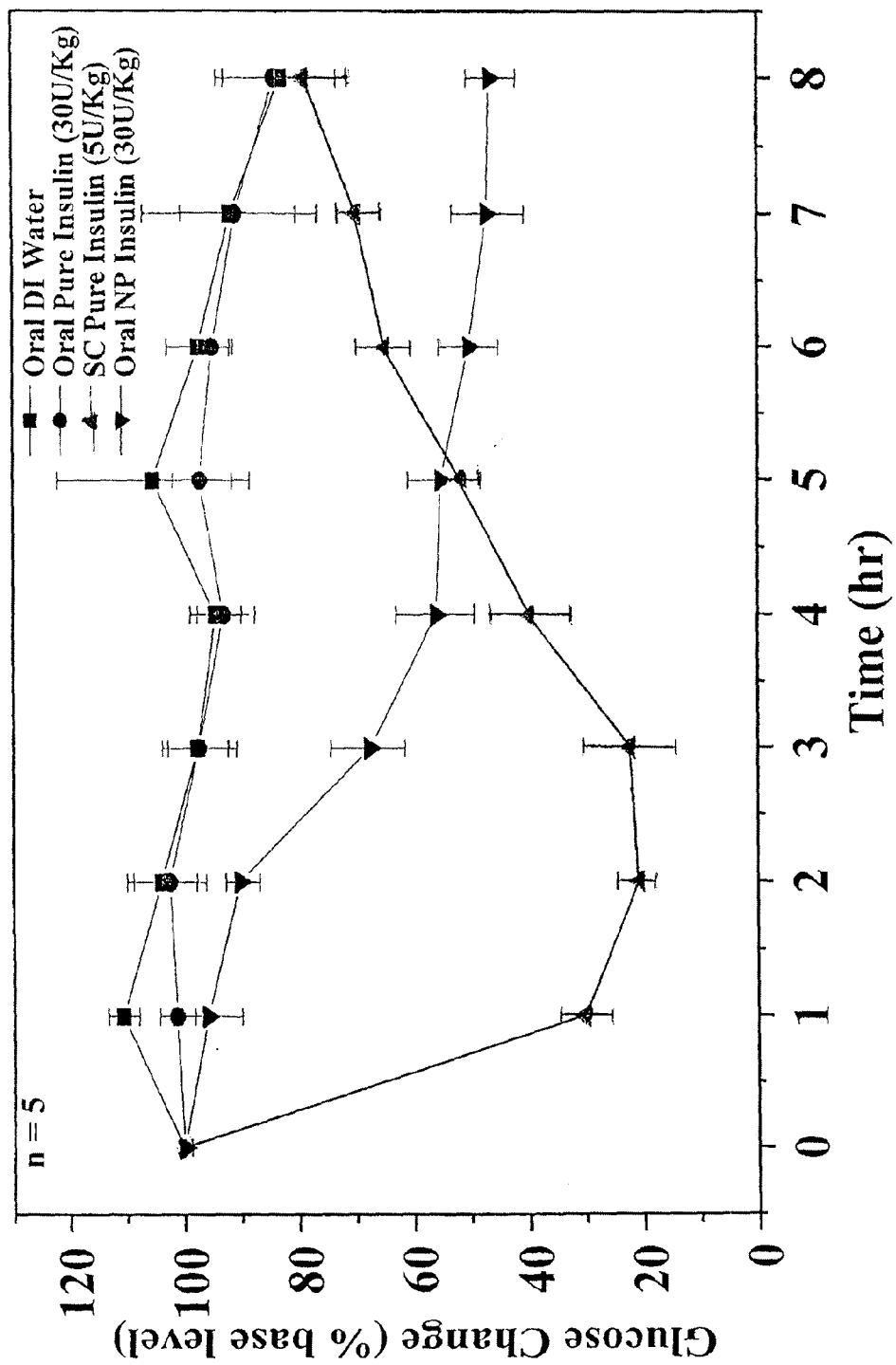
FIG. 15 shows the effect of insulin of orally administered insulin-loaded nanoparticles on hypoglycemia in diabetic rats.

FIG. 15 shows glucose change (hypoglycemic index) versus time of the in vivo animal study (n=5). The glucose change as a percentage of base lines (the base line was the glucose level in an animal subject without the effect of insulin) for both oral DI administration and oral insulin administration over a time interval of 8 hours appears relatively constant within the experimental measurement error range. It is illustrative that substantially all insulin from the oral administration route has been decomposed in rat stomach. As anticipated, the glucose decrease for the SC insulin injection route appears in rat blood in the very early time interval and starts to taper off after 3 hours in this exemplary study.

The most important observation of the study comes from the oral administration route with insulin-loaded nanoparticles. The blood glucose begins to decrease from the base line at about 2 hours after administration and sustains a lower glucose level at more than 8 hours into study. It implies that the current insulin-loaded nanoparticles may modulate the glucose level in animals in a sustained or prolonged effective mode. Some aspects of the invention provide a method of treating diabetes of an animal subject comprising orally administering insulin-containing nanoparticles with a dosage effective amount of the insulin to treat the diabetes, wherein at least a portion of the nanoparticles comprises a positively charged shell substrate and a negatively charged core substrate. In one embodiment, the dosage effective amount of the insulin to treat the diabetes comprises an insulin amount of between about 15 units to 45 units per kilogram body weight of the animal subject, preferably 20 to 40 units, and most preferably at about 25 to 35 units insulin per kilogram body weight.

Some aspects of the invention relate to a novel nanoparticle system that is composed of a low-MW CS and γ-PGA with CS dominated on the surfaces being configured to effectively open the tight junctions between Caco-2 cell monolayers. The surface of the nanoparticles is characterized with a positive surface charge. In one embodiment, the nanoparticles of the invention enables effective intestinal delivery for bioactive agent, including peptide, polypeptide, protein drugs, other large hydrophilic molecules, and the like. Such polypeptide drugs can be any natural or synthetic polypeptide that may be orally administered to a patient or an animal subject.

Exemplary drugs include, but are not limited to, insulin; growth factors, such as epidermal growth factor (EGF), insulin-like growth factor (IGF), transforming growth factor (TGF), nerve growth factor (NGF), platelet-derived growth factor (PDGF), bone morphogenic protein (BMP), fibroblast growth factor and the like; hemophilia factors, somatostatin; somatotropin; somatropin; somatrem; calcitonin; parathyroid hormone; colony stimulating factors (CSF); clotting factors; tumor necrosis factors: interferons; interleukins; gastrointestinal peptides, such as vasoactive intestinal peptide (VIP), cholecytokinin (CCK), gastrin, secretin, and the like; erythropoietins; growth hormone and GRF; vasopressins; octreotide; pancreatic enzymes; dismutases such as superoxide dismutase; thyrotropin releasing hormone (TRH); thyroid stimulating hormone; luteinizing hormone; LHRH; GHRH; tissue plasminogen activators; macrophage activator; chorionic gonadotropin; heparin; atrial natriuretic peptide; hemoglobin; retroviral vectors; relaxin; cyclosporin; oxytocin; vaccines; monoclonal antibodies; and the like; and analogs and derivatives of these compounds.

Triptorelin (acetate or pamoate), a decapeptide (pGlu-His-Trp-Ser-Tyr-D-Leu-Leu-Arg-Pro-NHEt), is a gonadotropin-releasing hormone agonist (GnRH agonist). By causing constant stimulation of the pituitary, it decreases pituitary secretion of gonadotropins luteinizing hormone (LH) and follcle stimulation hormone (FSH). Like other GnRH agonists, triptorelin may be used in the treatment of hormone-responsive cancers such as prostate cancer or breast cancer, precocious puberty, estrogen-dependent conditions (such as endometriosis or uterine fibroids), and in assisted reproduction. Triptorelin is marketed under the brand names Decapeptyl (Ipsen) and Diphereline and Gonapeptyl (Ferring Pharmaceuticals). In the United States, it is sold by Pfizer as Trelstar. Its systematic (IUPAC) name is 5-oxo-D-prolyl-L-histidyl-Ltryptophyl-L-seryl-Ltyrosyl-3-(1H-indol-2-yl)-L-alanylleucyl-L-arginyl-L-prolylglycinamide. It has a chemical formula $C_{64}H_{82}N_{18}O_{13}$ with a molecular mass 1311.5 g/mol.

Gemtuzumab ozogamicin (marketed by Wyeth as Mylotarg®) is a monoclonal antibody used to treat acute myelogenous leukemia. It is a monoclonal antibody to CD33 linked to a cytotoxic agent, calicheamicin. CD33 is expressed in most leukemic blast cells but also in normal hematopoietic cells, the intensity diminishing with maturation of stem cells. The gemtuzumab ozogamicin has been evaluated in the nanoparticle formulation of the present invention, showing typical characteristics in a spheroidal configuration with a particle size of between about 50 to 400 nm, a positive surface charge, and a narrow polydispersity index.

The bioactive agent of the present invention may also be selected from group consisting of oxytocin, vasopressin, adrenocorticotrophic hormone, prolactin, luliberin or luteinising hormone releasing hormone, growth hormone, growth hormone releasing factor, somatostatin, glucagon, interferon, gastrin, tetragastrin, pentagastrin, urogastroine, secretin, calcitonin, enkephalins, endorphins, angiotensins, renin, bradykinin, bacitracins, polymixins, colistins, tyrocidin, gramicidines, and synthetic analogues, modifications and pharmacologically active fragments thereof, monoclonal antibodies and soluble vaccines. Growth hormone (GH) is a peptide hormone that stimulates growth and cell reproduction in humans and other animals. It is a 191-amino acid, single chain polypeptide hormone that is synthesized, stored, and secreted by the somatotroph cells within the lateral wings of the anterior pituitary gland. Somatotrophin refers to the growth hormone produced natively in animals, the term somatropin refers to growth hormone produced by recombinant DNA technology,[1] and is abbreviated "rhGH" in humans.

In another embodiment, the nanoparticles of the invention increase the absorption of bioactive agents across the blood brain barrier and/or the gastrointestinal barrier. In still another embodiment, the nanoparticles with chitosan dominant at an outer layer that show positive surface charge serve as an enhancer in enhancing drug (bioactive agent) permeation of an administered bioactive agent when the bioactive agent and nanoparticles are orally administered in a two-component system, or orally administered substantially simultaneously.

Example No. 11

Epithelial Permeation and Enhancers

Chitosan and its derivatives may function as epithelial absorption enhancers. Chitosan, when protonated at an acidic pH, is able to increase the permeability of peptide drugs across mucosal epithelia. Some aspects of the invention provide co-administration of nanoparticles of the present invention and at least one permeation enhancer (in non-nanoparticle form or nanoparticle form). In one embodiment, the nanoparticles can be formulated by co-encapsulation of at least one permeation enhancer and at least one bioactive agent, with an option of adding other components. In one embodiment, the nanoparticles further comprise a permeation enhancer. The permeation enhancer may be selected from the group consisting of $Ca^{2+}$ chelators, bile salts, anionic surfactants, medium-chain fatty acids, phosphate esters, and chitosan or chitosan derivatives. In one embodiment, the nanoparticles of the present invention comprises a positively charged shell substrate and a negatively charged core substrate, for example, nanoparticles composed of γ-PGA and chitosan that is characterized with a substantially positive surface charge.

In some embodiments, the nanoparticles of the present invention, or with at least one permeation enhancer are loaded in a soft gel, pill, tablet, chewable, or capsule, or loaded in the enteric coated counterpart of the soft gel, pill, tablet, chewable, or capsule. The enhancers and the nanoparticles would arrive at the tight junction about the same time to enhance transiently opening the tight junction. In another embodiment, the at least one permeation enhancer is co-enclosed within the shell of the nanoparticles of the present invention. Therefore, some broken nanoparticles or fragments would release enhancers to assist the nanoparticles to open the tight junctions of the epithelial layers. In an alternate embodiment, the at least one enhancer is enclosed within a second nanoparticle having positive surface charges, particularly a chitosan-type nanoparticle, wherein the second nanoparticle is formulated without any bioactive agent or with a different bioactive agent from that bioactive agent in the first nanoparticle. When the drug-containing first nanoparticles of the present invention are co-administered with the above-identified second nanoparticles orally, the enhancers within the second nanoparticles are released in the gastrointestinal tract to assist the drug-containing first nanoparticles to open and pass the tight junction or facilitate enhanced drug absorption and transport.

Example No. 12

Nanoparticles Loaded with Exenatide

Exenatide is a member of the class of drugs known as incretin mimetics. Exenatide and pramlintide belong to a group of non-insulin injectables for treatment of diabetes. Exenatide has a molecular formula of $C_{184}H_{282}N_{50}O_{60}S$ with a molecular mass of about 4186.6 g/mol and an CAS no. 141732-76-5. Exenatide is suitable to be incorporated in the core portion of chitosan-shelled nanoparticles, wherein the core portion may include positively charged chitosan and negatively charged core substrate, such as γ-PGA or α-PGA, with the option of additional TPP and $MgSO_4$ in the core portion. In preparation, nanoparticles were obtained upon addition of a mixture of γ-PGA plus exenatide aqueous solution (pH 7.4, 2 ml), using a pipette during the addition stage (0.5-5 ml, PLASTIBRAND®, BrandTech Scientific Inc., Germany), into a low-MW CS aqueous solution (pH 6.0, 10 ml) at concentrations higher than 0.10% by w/v under magnetic stirring at room temperature to ensure positive surface charge. Nanoparticles were collected by ultracentrifugation at 38,000 rpm for 1 hour. Exenatide is wholly or substantially totally encapsulated within the nanoparticles. Supernatants were discarded and nanoparticles were resuspended in deionized water as the solution products. The nanoparticles thus obtained via the simple and mild ionic-gelation method described herein show typical characteristics in a spheroidal configuration with a particle size of between about 50 to 400 nm, a positive surface charge and a narrow polydispersity index. In one embodiment, it may further be encapsulated in capsules. In one embodiment, the interior surface of the capsule is treated to be lipophilic or hydrophobic. In another embodiment, the exterior surface of the capsule is enteric-coated or treated with an enteric coating polymer. In a preferred embodiment, the nanoparticles are further freeze-dried, optionally being mixed with trehalose or with hexan-1,2,3,4,5,6-hexyl in a freeze-drying process.

Glucagon-like peptide-1 (GLP-1) is derived from the transcription product of the proglucagon gene. The major source of GLP-1 in the body is the intestinal L cell that secretes GLP-1 as a gut hormone. The biologically active forms of GLP-1 are GLP-1-(7-37) and GLP-1-(7-36)NH2. GLP-1 secretion by L cells is dependent on the presence of nutrients in the lumen of the small intestine. The secretagogues (agents that cause or stimulate secretion) of this hormone include major nutrients like carbohydrate, protein and lipid. Once in the circulation, GLP-1 has a half-life of less than 2 minutes, due to rapid degradation by the enzyme dipeptidyl peptidase-4 (DPP-4). Commercial GLP-1 ELISA kits are generally available for GLP-1 assay.

Exenatide (marketed as Byetta) is the first of a new class of medications (incretin mimetics) approved for the treatment of type 2 diabetes. It is manufactured and marketed by Amylin Pharmaceuticals and Eli Lilly and Company. Exenatide is a synthetic version of exendin-4, a hormone in the saliva of the Gila monster, a lizard native to several Southwestern American states. It displays properties similar to human GLP-1. Exenatide is a 39-amino-acid peptide that mimics the GLP-1 incretin, an insulin secretagogue with glucoregulatory effects. While it may lower blood glucose levels on its own, it can also be combined with other medications such as pioglitazone, metformin, sulfonylureas, and/or insulin (not FDA approved yet) to improve glucose control. The approved use of exenatide is with sulfonylureas, metformin or thiazolinediones. The medication is injected subcutaneously twice per day using a pre-filled pen device.

Typical human responses to exenatide include improvements in the initial rapid release of endogenous insulin, suppression of pancreatic glucagon release, delayed gastric emptying, and reduced appetite—all of which function to lower blood glucose. Whereas some other classes of diabetes drugs such as sulfonylureas, thiazolinediones, and insulin are often associated with weight gain, Byetta often is associated with significant weight loss. Unlike sulfonylureas and meglitinides, exenatide only increases insulin synthesis and secretion in the presence of glucose, lessening the risk of hypoglycemia. Byetta is also being used by some physicians to treat insulin resistance.

Example No. 13

Nanoparticles Loaded with Pramlintide

Pramlintide is a synthetic amylin analogue (marketed as Symlin). Amylin is a natural, pancreatic islet peptide that is normally secreted with insulin in response to meals. It has several beneficial effects on glucose homeostasis: suppression of glucagon secretion, delaying of gastric emptying, and promotion of satiety. It is currently given before meals, in a separate subcutaneous injection but usually in conjunction with insulin. Pramlintide has a molecular formula of $C_{171}H_{269}N_{51}O_{53}S_2$ with a molecular mass of about 3951.4 g/mol and an CAS no. 151126-32-8. Pramlintide (positively charged) is currently delivered as an acetate salt. Pramlintide is suitable to be incorporated in a core portion of a chitosan-shelled nanoparticles, wherein the core portion may include positively charged chitosan and negatively charged core substrate, such as γ-PGA or α-PGA, with an option for additional TPP and $MgSO_4$ in the core portion. In other words, pramlintide may replace at least a portion of positively charged chitosan in the core by interacting with the negatively core substrate, such as PGA, heparin or the like. In preparation, nanoparticles were obtained upon the addition of a mixture of γ-PGA plus ppramlintide aqueous solution (pH 7.4, 2 ml), using a pipette during the addition step (0.5-5 ml, PLASTIBRAND®, BrandTech Scientific Inc., Germany), into a low-MW CS aqueous solution (pH 6.0, 10 ml) at concentrations higher than 0.10% by w/v under magnetic stirring at room temperature to ensure positive surface charge.

Nanoparticles were collected by ultracentrifugation at 38,000 rpm for 1 hour. Pramlintide is wholly or substantially totally encapsulated within the nanoparticles. Supernatants were discarded and nanoparticles were resuspended in deionized water as the solution products. The nanoparticles thus obtained via the simple and mild ionic-gelation method described herein show typical characteristics in a spheroidal configuration with a particle size of between about 50 to 400 nm, a positive surface charge and a narrow polydispersity index. In one embodiment, it may further be encapsulated in capsules. In one embodiment, the interior surface of the capsule is treated to be lipophilic or hydrophobic. In another embodiment, the exterior surface of the capsule is enteric-coated. In a preferred embodiment, the nanoparticles are further freeze-dried, and can be optionally mixed with trehalose or with hexan-1,2,3,4,5,6-hexyl in a freeze-drying process.

Pramlintide is an analogue of Amylin, a small peptide homone that is released into the bloodstream after a meal by the β-cells of the pancreas along with insulin. Like insulin, amylin is deficient in individuals with diabetes. By augmenting endogenous amylin, pramlintide aids in the absorption of glucose by slowing gastric emptying, promoting satiety via hypothalamic receptors (different receptors than GLP-1), and inhibiting inappropriate secretion of glucagon, a catabolic hormone that opposes the effects of insulin and amylin.

Example No. 14

Nanoparticles Loaded with Calcitonin

Calcitonin is a protein drug that therapeutically serves as calcium regulators for treating osteoporosis (J. Pharm. Pharmacol. 1994; 46:547-552). Calcitonin has a molecular formula of $C_{145}H_{240}N_{44}O_{48}S_2$ with a molecular weight of about 3431.9 and an isoelectric point of 8.7. The net charge for calcitonin at pH7.4 is positive that makes it suitable for complexing or conjugating with negatively charged core substrate, such as γ-PGA or α-PGA. In preparation, nanoparticles were obtained upon the addition of a mixture of γ-PGA and calcitonin aqueous solution (pH 7.4, 2 ml), using a pipette during the addition step (0.5-5 ml, PLASTIBRAND®, BrandTech Scientific Inc., Germany), into a low-MW CS aqueous solution (pH 6.0, 10 ml) at concentrations higher than 0.10% by w/v under magnetic stirring at room temperature to ensure positive surface charge. Nanoparticles were collected by ultracentrifugation at 38,000 rpm for 1 hour. Calcitonin is wholly or substantially totally encapsulated within the nanoparticles. Supernatants were discarded and nanoparticles were resuspended in deionized water as the solution products, further encapsulated in capsules or further treated with an enteric coating polymer. The nanoparticles thus obtained via the simple and mild ionic-gelation method described herein show typical characteristics in a spheroidal configuration with a particle size of between about 50 to 400 nm, a positive surface charge and a narrow polydispersity index.

Example No. 15

Nanoparticles Loaded with Teriparatide

Teriparatide (Forteo®) is a recombinant form of parathyroid hormone, used in the treatment of some forms of osteoporosis. It is manufactured and marketed by Eli Lilly and Company. Currently teriparatide is administered by injection once a day in the thigh or abdomen. The recommended dose is 20 µg per day. Teriparatide has the chemical formula $C181H_{291}N_{55}O_{51}S_2$ with a molecular mass of 4117.72 g/mol. Teriparatide is the portion of human Parathyroid hormone (PTH), amino acid sequence 1 through 34 of the complete molecule which contains amino acid sequence 1 to 84. Endogenous PTH is the primary regulator of calcium and phosphate metabolism in bone and kidneys. Daily injections of teriparatide stimulate new bone formation leading to increased bone mineral density.

Teriparatide is the first FDA approved agent for the treatment of osteoporosis that stimulates new bone formation. In one exemplary preparation, nanoparticles were obtained upon addition of a mixture of γ-PGA plus teriparatide aqueous solution (2 ml), using a pipette (0.5-5 ml, PLASTIBRAND®, BrandTech Scientific Inc., Germany) during the addition step, into a low-MW CS aqueous solution (pH 6.0, 10 ml) at concentrations higher than 0.10% by w/v under magnetic stirring at room temperature to ensure positive surface charge. Nanoparticles were collected by ultracentrifugation at 38,000 rpm for 1 hour. Teriparatide is wholly or substantially totally encapsulated within the nanoparticles. Supernatants were discarded and nanoparticles were resuspended in deionized water as the solution products, further encapsulated in capsules/enteric capsules or further treated with lyophilization. The nanoparticles thus obtained via the simple and mild ionic-gelation method described herein show typical characteristics in a spheroidal configuration with a particle size of between about 50 to 400 nm, a positive surface charge and a narrow polydispersity index.

Example No. 16

Nanoparticles Loaded with Vancomycin

Vancomycin is a protein drug that serves therapeutically as an antibiotic against bacterial pathogens. Vancomycin has a molecular formula of $C_{66}H_{75}N_9O_{24}$ with a molecular weight of about 1485.7 and an isoelectric point of 5.0. The net charge for vancomycin at pH7.4 is negative, which is suitable to complex or conjugate with a portion of negatively charged shell substrate, such as chitosan. In preparation, nanoparticles were obtained upon addition of a mixture of γ-PGA and vancomycin aqueous solution (pH 7.4, 2 ml), using a pipette (0.5-5 ml, PLASTIBRAND®, BrandTech Scientific Inc., Germany), into a low-MW CS aqueous solution (pH 6.0, 10 ml) with excess concentrations under magnetic stirring at room temperature, wherein CS concentration is provided sufficiently to conjugate vancomycin, to counterbalance γ-PGA, and exhibit positive surface charge for the nanoparticles. Nanoparticles were collected by ultracentrifugation at 38,000 rpm for 1 hour. Vancomycin is wholly or substantially totally encapsulated within the nanoparticles. Supernatants were discarded and nanoparticles were resuspended in deionized water as the solution products, further encapsulated in capsules or further treated with an enteric coating on capsules. The nanoparticles thus obtained via the simple and mild ionic-gelation method described herein show typical characteristics in a spheroidal configuration with a particle size of between about 50 to 400 nm, a positive surface charge and a narrow polydispersity index.

Tigecycline is an glycylcycline antibiotic developed and marketed by Wyeth under the brand name Tygacil®. It was developed in response to the growing prevalence of antibiotic resistance in bacteria such as *Staphylococcus aureus*. It has a systematic (IUPAC) name N-[(5aR,6aS,7S,9Z,10aS)-9-[amino(hydroxy)methylidene]-4,7-bis(dimethylamino)-1, 10a, 12-trihydroxy-8,10,11-trioxo-5,5a,6,6a,7,8,9,10,10a, 11-decahydrotetracen-2-yl]-2-(tert-butylamino)acetamide. The chemical formula is $C_{29}H_{39}N_5O_8$ with a molecular mass 585.65 g/mol. The drug inhibits the bacterial 30S ribosome and is bacteriostatic. Tigecycline is active against many Gram-positive bacteria, Gram-negative bacteria and anaerobes—including activity against methicillin-resistant *Staphylococcus aureus* (MRSA) and multi-drug resistant strains of *Acinetobacter baumannii*. Tigecycline is currently given by slow intravenous infusion (30 to 60 minutes). A single dose of 100 mg is given first, followed by 50 mg every twelve hours after that.

Lincomycin is a lincosamide antibiotic that comes from the actinomyces *Streptomyces lincolnensis*. It has been structurally modified by thionyl chloride to its more commonly known 7-chloro-7-deoxy derivative, clindamycin. Its systematic (IUPAC) name is (2S,4R)—N-[(1R,2R)-2-hydroxy-1-[(2R,3R,4S,5R,6R)-3,4,5-trihydroxy-6-(methylsulfanyl) oxan-2-yl]propyl]-1-methyl-4-propylpyrrolidine-2-carboxamide. Its chemical formula is $C_{18}H_{34}N_2O_6S$ with a molecular mass 406.538 g/mol.

An antibiotic is a substance or compound (also called chemotherapeutic agent) that kills or inhibits the growth of bacteria. Antibiotics belong to the group of antimicrobial compounds, i.e., those for treating infections caused by microorganisms, including viruses, fungi, and protozoa. Penicillin is a group of antibiotics derived from *Penicillium* fungi. They are Beta-lactam antibiotics used in the treatment of bacterial infections caused by susceptible, usually Gram-positive, organisms. The term Penam is used to describe the core skeleton of a member of a penicillin antibiotic. This skeleton has the molecular formula R—$C_9H_{11}N_2O_4S$, where R is a variable side chain. Ampicillin is a beta-lactam antibiotic that has been used extensively to treat bacterial infections since 1961. It is considered part of the aminopenicillin family and is roughly equivalent to amoxicillin in terms of spectrum and level of activity. It can sometimes result in non-allergic reactions that range in severity from a rash (e.g. patients with mononucleosis) to potentially lethal anaphylaxis. Ampicillin is closely related to amoxicillin, another type of penicillin, and both are used to treat urinary tract infections, otitis media, uncomplicated community-acquired pneumonia, *Haemophilus influenzae, salmonellosis* and *Listeria meningitis*. Other types include Penicillin V, Procaine benzylpenicillin, and Benzathine benzylpenicillin.

Some aspects of the invention relate to a method of treating infections caused by microorganisms in an animal subject, the method comprising administering nanoparticles composed of an antibiotic, chitosan, and a core portion of negatively charged substrate, wherein a surface of the nanoparticles is dominated by the chitosan. In one embodiment, the method of administering the nanoparticles may comprise an oral route, intravenous route, subcutaneous injection route, intramuscular route, buccal route, intranasal route, parenteral route, and the like.

Piperacillin is an extended spectrum beta-lactam antibiotic of the ureidopenicillin class. It is normally used together with a beta-lactamase inhibitor such as tazobactam, which is commercially available. The combination has activity against many Gram-positive and Gram-negative pathogens and anaerobes, including *Pseudomonas aeruginosa*. The systematic (IUPAC) name is (2S,5R,6R)-6-{[(2R)-2-[(4-ethyl-2,3-dioxo-piperazine-1-carbonypamino]-2-phenyl-acetyl] amino}-3,3-dimethyl-7-oxo-4-thia-1-azabicyclo[3.2.0] heptane-2-carboxylic acid. Its chemical formula is $C_{23}H_{26}N_5O_7S$ with a molecular mass 516,548 g/mol. Piperacillin is not absorbed orally, and must therefore be given by intravenous or intramuscular injection; piperacillin/tazobactam is administered intravenously every 6 or 8 hours; the drug may also be given by continuous infusion, but this has not been shown to be superior.

An aminoglycoside is a molecule composed of a sugar group and an amino group. Several aminoglycosides function as antibiotics that are effective against certain types of bacteria. They include amikacin, arbekacin, gentamicin, kanamycin, neomycin, netilmicin, paromomtcin, rhodostreptomycin, streptomycin, tobramycin, and apramycin.

Aminoglycosides have several potential antibiotic mechanisms, some as protein synthesis inhibitors, although their exact mechanism of action is not fully known: (1) They interfere with the proofreading process, causing increased rate of error in synthesis with premature termination; (2) Also, there is evidence of inhibition of ribosomal translocation where the peptidyl-tRNA moves from the A-site to the P-site; (3) They can also disrupt the integrity of bacterial cell membrane.

Aminoglycosides bind to the bacterial 30S ribosomal subunit; some work by binding to the 50S subunit. There is a significant relationship between the dose administered and the resultant plasma level in blood. Therapeutic drug monitoring (TDM) is necessary to obtain the correct dose. These agents exhibit a post-antibiotic effect in which there is no or very little drug level detectable in blood, but there still seems to be inhibition of bacterial re-growth. This is due to strong, irreversible binding to the ribosome, and remains intracellular long after plasma levels drop. This allows a prolonged dosage interval. Depending on their concentration, they act as bacteriostatic or bactericidal agents.

The protein synthesis inhibition of aminoglycosides does not usually produce a bactericidal effect, let alone a rapid one as is frequently observed on susceptible Gram-negative bacilli. Aminoglycosides competitively displace cell biofilm-associated $Mg^{2+}$ and $Ca^{2+}$ that link the polysaccharides of adjacent lipopolysaccharide molecules. The result is shedding of cell membrane blebs, with formation of transient holes in the cell wall and disruption of the normal permeability of the cell wall. This action alone may be sufficient to kill most susceptible Gram-negative bacteria before the aminoglycoside has a chance to reach the 30S ribosome.

Traditionally, the antibacterial properties of aminoglycosides were believed to result from inhibition of bacterial protein synthesis through irreversible binding to the 30S bacterial ribosome. This explanation, however, does not account for the potent bactericidal properties of these agents, since other antibiotics that inhibit the synthesis of proteins (such as tetracycline) are not bactericidal. Recent experimental studies show that the initial site of action is the outer bacterial membrane. The cationic antibiotic molecules create fissures in the outer cell membrane, resulting in leakage of intracellular contents and enhanced antibiotic uptake. This rapid action at the outer membrane probably accounts for most of the bactericidal activity.

Energy is needed for aminoglycoside uptake into the bacterial cell. Anaerobes have less energy available for this uptake, so aminoglycosides are less active against anaerobes. Aminoglycosides are useful primarily in infections involving aerobic, gram-negative bacteria, such as *Pseudomonas, Acinetobacter*, and *Enterobacter*. In addition, some *Mycobacteria*, including the bacteria that cause tuberculosis, are susceptible to aminoglycosides. The most frequent use of aminoglycosides is empiric therapy for serious infections such as septicemia, complicated intraabdominal infections, complicated urinary tract infections, and nosocomial respiratory tract infections. Usually, once cultures of the causal organism are grown and their susceptibilities tested, aminoglycosides are discontinued in favor of less toxic antibiotics.

Streptomycin was the first effective drug in the treatment of tuberculosis, though the role of aminoglycosides such as streptomycin and amikacin has been eclipsed (because of their toxicity and inconvenient route of administration) except for multiple drug resistant strains.

Infections caused by gram-positive bacteria can also be treated with aminoglycosides, but other types of antibiotics are more potent and less damaging to the host. In the past, the aminoglycosides have been used in conjunction with beta-lactam antibiotics in streptococcal infections for their synergistic effects, particularly in endocarditis. One of the most frequent combinations is ampicillin (a beta-lactam, or penicillin-related antibiotic) and gentamicin. Often, hospital staff refer to this combination as "amp and gent" or more recently called "pen and gent" for penicillin and gentamicin. Aminoglycosides are mostly ineffective against anaerobic bacteria, fungi and viruses.

Experimentation with aminoglycosides as a treatment of cystic fibrosis (CF) has shown some promising results. CF is caused by a mutation in the gene coding for the cystic fibrosis transmembrane conductance regulator (CFTR) protein. In approximately 10% of CF cases the mutation in this gene causes its early termination during translation, leading to the formation of is truncated and non-functional CFTR protein. It is believed that gentamicin distorts the structure of the ribosome-RNA complex, leading to a misreading of the termination cordon, causing the ribosome to "skip" over the stop sequence and to continue with the normal elongation and production of the CFTR protein. The treatment is still experimental but showed improvement in cells from CF patients with susceptible mutations.

Since they are not absorbed from the gut via conventional transcellular permeability, they are administered intravenously and intramuscularly. Some are used in topical preparations for wounds. Oral administration can be used for gut decontamination (e.g. in hepatic encephalopathy). Tobramycin may be administered in a nebulized form. Some aspects of the invention relate to a nanoparticle formulation as disclosed herein to enhance absorption via paracellular permeation route.

Temsirolimus is an intravenous drug for the treatment of renal cell carcinoma (RCC), developed by Wyeth Pharmaceuticals and approved by the FDA in late May 2007. It is a derivative of sirolimus and is sold as Torisel. Its chemical formula is $C_{56}H_{87}NO_{16}$ with a molecular mass 1030.28 g/mol. mTOR (mammalian target of rapamycin) is a kinase enzyme inside the cell that collects and interprets the numerous and varied growth and survival signals received by tumor cells. When the kinase activity of mTOR is activated, its downstream effectors, the synthesis of cell cycle proteins such as cyclin D and hypoxia-inducible factor-1a (HIF-1a) are increased. HIF-1a then stimulates VEGF. Temsirolimus is a specific inhibitor of mTOR and interferes with the synthesis of proteins that regulate proliferation, growth, and survival of tumor cells. Treatment with temsirolimus leads to cell cycle arrest in the G1 phase, and also inhibits tumor angiogenesis by reducing synthesis of VEGF. The recommended dose of temsirolimus is 25 mg IV infused over 30-60 minutes once per week.

Some aspects of the invention relate to a method of enhancing epithelial permeation of bioactive agents configured and adapted for delivering at least one bioactive agent in an animal subject comprising administering nanoparticles composed of γ-PGA and chitosan, wherein the nanoparticles are loaded with a therapeutically effective amount or dose of the at least one bioactive agent. The nanoparticle of the present invention is an effective intestinal delivery system for peptide and protein drugs and other large hydrophilic molecules. In a further embodiment, the bioactive agent is selected from the group consisting of proteins, peptides, nucleosides, nucleotides, antiviral agents, antineoplastic agents, antibiotics, antiepileptic drug, and anti-inflammatory drugs. In a further embodiment, the bioactive agent is selected from the group consisting of calcitonin, cyclosporin, insulin, oxytocin, tyrosine, enkephalin, tyrotropin releasing hormone (TRH), follicle stimulating hormone (FSH), luteinizing hormone (LH), vasopressin and vasopressin analogs, catalase, superoxide dismutase, interleukin-II (IL2), interleukin-11 (IL-11), interferon, colony stimulating factor (CSF), tumor necrosis factor (TNF) and melanocyte-stimulating hormone.

In a further embodiment, the bioactive agent is an Alzheimer antagonist. In one embodiment, the antiepileptic drug may include Neurontin (gabapentin), Lamictal (lamotrigine), Febatol (felbamate), Topamax (topiramate), Cerebyx (fosphenyloin), Dilantin (phenyloin), Depakene (valproic acid), Tegretol (carbamazepine), carbamazepine epoxide, Vimpat (lacosamide) and phenobarbitol. Fosphenyloin (Cerebyx by Parke-Davis; Prodilantin by Pfizer Holding France) is a water-soluble phenyloin prodrug used only in hospitals for the treatment of epileptic seizures through parental delivery. Fosphenyloin has systematic (IUPAC) name of (2,5-dioxo-4,4-diphenyl-imidazolidin-1-yl) methoxyphosphonic acid. It has the chemical formula of $C_{16}H_{15}N_2O_6P$ with molecular mass 362.274 g/mol.

Example No. 17

Nanoparticles Loaded with Heparin

Heparin is a negatively charged drug that serves therapeutically as an anti-coagulant. Heparin is generally administered by intravenous injection. Some aspects of the invention relate to heparin nanoparticles for oral administration or subcutaneous administration. In a further embodiment, heparin serves as at least a portion of the core substrate with chitosan as shell substrate, wherein heparin conjugates with at least one bioactive agent as disclosed herein. In preparation, nanoparticles were obtained upon addition of heparin Leo aqueous solution (2 ml), using a pipette (0.5-5 ml, PLASTIBRAND®, BrandTech Scientific Inc., Germany), into a low-MW CS aqueous solution (pH 6.0, 10 ml) with excess concentrations under magnetic stirring at room temperature. Nanoparticles were collected by ultracentrifugation at 38,000 rpm for 1 hour. Heparin is wholly or substantially totally encapsulated within the nanoparticles. The nanoparticles thus obtained via the simple and mild ionic-gelation method described herein show typical characteristics in a spheroidal configuration with a particle size of between about 50 to 400 nm, a positive surface charge and a narrow polydispersity index. Table 4 shows the conditions of solution preparation and the average nanoparticle size.

TABLE 4

| Conditions | Heparin conc. @ 2 ml | Chitosan conc. @ 10 ml | Particle size (nm) |
| --- | --- | --- | --- |
| A | 200 iu/ml | 0.09% | 298.2 ± 9.3 |
| B | 100 iu/ml | 0.09% | 229.1 ± 4.5 |
| C | 50 iu/ml | 0.09% | 168.6 ± 1.7 |
| D | 25 iu/ml | 0.09% | 140.1 ± 2.3 |

To evaluate the pH stability of the heparin-containing nanoparticles from Example no. 17, the nanoparticles from Condition D in Table 4 are subjected to various pH level for 2 hours (sample size=7). Table 5 shows the average size, size distribution (polydispersity index: PI) and zeta potential (Zeta) of the nanoparticles at the end of 2 hours under various pH environments. The data shows the nanoparticles are relatively stable. In one embodiment, the nanoparticles of the present invention may include heparin, heparin sulfate, small molecular weight heparin, and heparin derivatives.

TABLE 5

| | pH | | | | |
| --- | --- | --- | --- | --- | --- |
| | 1.5 | 2.6 | 6.6 | 7.4 | Deionized water @ 5.9 |
| Size (nm) | 150 ± 9 | 160 ± 12 | 153 ± 2 | 154 ± 4 | 147 ± 5 |
| PI | 0.54 ± 0.03 | 0.50 ± 0.04 | 0.08 ± 0.02 | 0.32 ± 0.03 | 0.37 ± 0.02 |
| Zeta (+) | 15 ± 2 | 33 ± 6 | 15 ± 0.1 | 11 ± 0.2 | 18 ± 4 |

In a further embodiment, a pharmaceutically effective amount of growth factor such as bFGF is added to heparin Leo aqueous solution before the pipetting step in Example No. 15. In our laboratory, growth factors and proteins with pharmaceutically effective amounts have been successfully conjugated with heparin to form nanoparticles of the present invention with chitosan as the shell substrate, wherein the growth factor is selected from the group consisting of Vascular Endothelial Growth Factor (VEGF), Vascular Endothelial Growth Factor 2 (VEGF2), basic Fibroblast Growth Factor (bFGF), Vascular Endothelial Growth Factor 121 (VEGF121), Vascular Endothelial Growth Factor 165 (VEGF165), Vascular Endothelial Growth Factor 189 (VEGF189), Vascular Endothelial Growth Factor 206 (VEGF206), Platelet Derived Growth Factor (PDGF), Platelet Derived Angiogenesis Factor (PDAF), Transforming Growth Factor-β (TGF-β), Transforming Growth Factor-α (TGF-α), Platelet Derived Epidermal Growth Factor (PDEGF), Platelet Derived Wound Healing Formula (PD-WHF), epidermal growth factor, insulin-like growth factor, acidic Fibroblast Growth Factor (aFGF), human growth factor, and combinations thereof; and the protein is selected from the group consisting of haemagglutinin (HBHA), Pleiotrophin, buffalo seminal plasma proteins, and combinations thereof.

In a co-pending application, U.S. patent application Ser. No. 10/916,170 filed Aug. 11, 2004, it is disclosed that a biomaterial with free amino groups of lysine, hydroxylysine, or arginine residues within biologic tissues is crosslinkable with genipin, a crosslinker (Biomaterials 1999; 20:1759-72). It is also disclosed that the crosslinkable biomaterial may be crosslinked with a crosslinking agent or with light, such as ultraviolet irradiation, wherein the crosslinkable biomaterial may be selected from the group consisting of collagen, gelatin, elastin, chitosan, NOCC (N, O, carboxylmethyl chitosan), fibrin glue, biological sealant, and the like. Further, it is disclosed that a crosslinking agent may be selected from the group consisting of genipin, its derivatives, analog (for example, aglycon geniposidic acid), stereoisomers and mixtures thereof. In one embodiment, the crosslinking agent may further be selected from the group consisting of epoxy compounds, dialdehyde starch, glutaraldehyde, formaldehyde, dimethyl suberimidate, carbodiimides, succinimidyls, diisocyanates, acyl azide, reuterin, ultraviolet irradiation, dehydrothermal treatment, tris(hydroxymethyl)phosphine, ascorbate-copper, glucose-lysine and photo-oxidizers, and the like.

In one embodiment, it is disclosed that loading a drug onto a chitosan-containing biological material crosslinked with genipin or other crosslinking agent may be used as biocompatible drug carriers for drug slow-release or sustained release. Several biocompatible plastic polymers or synthetic polymers have one or more amine group in their chemical structures, for example poly(amides) or poly(ester amides). The amine group may become reactive toward a crosslinking agent, such as glutaraldehyde, genipin or epoxy compounds of the present invention. In one embodiment, the nanoparticles comprised of crosslinkable biomaterial is crosslinked, for example up to about 50% degree or more of crosslinking, preferably about 1 to about 20% degree of crosslinking of the crosslinkable components of the biomaterial, enabling sustained biodegradation of the biomaterial and/or sustained drug release.

By modifying the chitosan structure to alter its charge characteristics, such as grafting the chitosan with EDTA, methyl, N-trimethyl, alkyl (for example, ethyl, propyl, butyl, isobutyl, etc.), polyethylene glycol (PEG), or heparin (including low molecular weight heparin, regular molecular weight heparin, and genetically modified heparin), the surface charge density (zeta potential) of the CS-γPGA nanoparticles may become more pH resistant or hydrophilic. In one embodiment, the chitosan is grafted with polyacrylic acid. In one embodiment, the chitosan employed is N-trimethyl chitosan (TMC), low MW-chitosan, EDTA-chitosan, chitosan derivatives, and/or combinations thereof. An exemplary chemical structure for EDTA-chitosan is shown below:

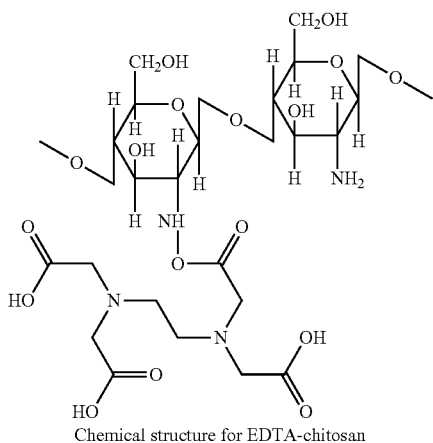
Chemical structure for EDTA-chitosan

By way of illustration, trimethyl chitosan chloride might be used in formulating the CS-γPGA nanoparticles for maintaining its spherical biostability at a pH lower than 2.5, preferably at a pH as low as 1.0. Some aspects of the invention provide a drug-loaded chitosan-containing biological material crosslinked with genipin or other crosslinking agent as a biocompatible drug carrier for enhancing biostability at a pH lower than 2.5, preferably within at a pH as low as 1.0.

It is known that the pKa values of CS (amine groups) and γ-PGA (carboxylic groups) are 6.5 and 2.9, respectively. NPs were prepared in DI water (pH 6.0). At pH 6.0, CS (TMC25) and γ-PGA were ionized. The ionized CS (TMC25) and γ-PGA could form polyelectrolyte complexes, which resulted in a matrix structure with a spherical shape. At pH 1.2-2.0, most carboxylic groups on γ-PGA were in the form of —COON. Hence, there was little electrostatic interaction between CS (TMC25) and γ-PGA; thus NPs became disintegrated (Table 6). Similarly, at pH values above 6.6, the free amine groups on CS (TMC25) were deprotonated; thus leading to the disintegration of NPs. This might limit the efficacy of drug delivery and absorption in the small intestine.

When increasing the degree of quaternization on TMC (TMC40 and TMC55), the stability of NPs in the pH range of 6.6-7.4 increased significantly. However, the swelling of TMC55/γ-PGA NPs at pH 7.4 was minimal (due to the highly quaternized TMC55), which might limit the release of loaded drugs. In contrast, TMC40/γ-PGA NPs swelled significantly with increasing the pH value. TMC40/γ-PGA NPs (collapsed NPs or fragments) still retained a positive surface charge with a zeta potential value of 17.3 mV at pH 7.4.

Thus, TMC40/γ-PGA/drug NPs have superior stability in a broader pH range compared to CS/γ-PGA/drug NPs. In one embodiment, at around body fluid pH of about 7.4, the bioactive nanoparticles of the present invention may appear to be in configuration of chitosan-shelled fragments or chitosan-containing fragments. At least a portion of the surface of the chitosan-shelled fragments or chitosan-containing fragments from the bioactive nanoparticles of the present invention shows positive zeta potential characteristics.

The results of molecular dynamic simulations showed that the molecular chains of TMC40 (in dark black) and γ-PGA (in light black) in their self-assembled complex were tightly entangled with each other at pH 6.0. The surface of the complex was dominated by TMC40 molecules. Relaxations of TMC40 and γ-PGA molecular chains at pH 2.5 resulted in a moderate swelling of the TMC40/γ-PGA complex, while its surface was still dominated by the positively charged TMC molecules, thus retaining a positive surface charge.

Similarly, relaxations of TMC40 and γ-PGA molecular chains at pH 7.4 resulted in a significant swelling of the TMC40/γ-PGA complex, while its surface was still dominated by the positively charged TMC molecules, thus retaining a positive surface charge. The swollen TMC40/γ-PGA/drug nanoparticles tend to slightly disintegrate (due to the effect of its pH instability) so to form fragments consisting of TMC40/γ-PGA/drug with surface-dominated TMC40.

The TMC40/γ-PGA/drug fragments with surface-dominated TMC40 would adhere and infiltrate into the mucus of the epithelial membrane of the blood-brain barrier, and then trigger transiently opening the tight junctions between enterocytes. Table 6 shows mean particle sizes, zeta potential values, and polydispersity indices of nanoparticles (NPs) self-assembled by TMC polymers with different degrees of quaternization and γ-PGA at distinct pH environments (n=5 batches). As shown in Table 6, TMC40/γ-PGA NPs still retained a positive surface charge with a zeta potential value of 17.3 mV at pH 7.4.

Freeze-Dried Nanoparticles

A pharmaceutical composition of nanoparticles of the present invention may comprise a first component of at least one bioactive agent, a second component of chitosan (including regular molecular weight and low molecular weight chitosan), and a third component that is negatively charged. In one embodiment, the second component dominates on a surface of the nanoparticle. In another embodiment, the chitosan is N-trimethyl chitosan.

In still another embodiment, the low molecular weight chitosan has a molecular weight less than that of a regular molecular weight chitosan. The nanoparticles may further comprise tripolyphosphate and magnesium sulfate. For example, a first solution of (2 ml 0.1% γ-PGA aqueous solution @pH 7.4+0.05% Insulin+0.1% Tripolyphosphate (TPP)+0.2% MgSO4) is added to a base solution (10 ml 0.12% chitosan aqueous solution @pH 6.0) as illustrated in Example no. 3 under magnetic stirring at room temperature. Nanoparticles were collected by ultracentrifugation at 38,000 rpm for 1 hour. The bioactive agent, the third component, tripolyphosphate and magnesium sulfate are wholly or substantially totally encapsulated within the nanoparticles. Supernatants were discarded and nanoparticles were resuspended in deionized water for freeze-drying preparation. Other operating conditions or other bioactive agent (such as protein, peptide, siRNA, growth factor, the one defined and disclosed herein, and the like) may also apply.

Several conventional coating compounds that form a protective layer on particles are used to physically coat or mix with the nanoparticles before a freeze-drying process. The coating compounds may include trehalose, mannitol, glycerol, and the like. Trehalose, also known as mycose, is an alpha-linked (disaccharide) sugar found extensively but not abundantly in nature. It can be synthesized by fungi, plants and invertebrate animals. It is associated with anhydrobiosis—the ability of plants and animals to withstand prolonged periods of desiccation. The sugar is thought to form a gel phase as cells dehydrate, which prevents disruption of internal cell organelles by effectively splinting them in position. Rehydration then allows normal cellular activity to resume without the major, generally lethal damage, which would normally follow a dehydration/rehydration cycle. Trehalose has the added advantage of being an antioxidant.

Trehaloze has a chemical formula as $C_{12}H_{22}O_{11} \cdot 2H_2O$. It is listed as CAS no. 99-20-7 and PubChem 7427. The molecular structure for trehalose is shown below.

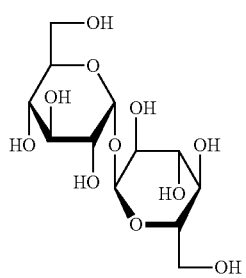

Trehalose was first isolated from the ergot of rye. Trehalose is a non-reducing sugar formed from two glucose units joined by a 1-1 alpha bond, giving it the name α-D-glucopyranosyl-(1→1)-α-D-glucopyranoside. The bonding makes trehalose very resistant to acid hydrolysis, and therefore stable in a solution at high temperatures, even under acidic conditions. The bonding also keeps non-reducing sugars in a closed-ring form, such that the aldehyde or ketone end-groups do not bind to the lysine or arginine residues of proteins (a process called glycation). Trehalose has about 45% the sweetness of sucrose. Trehalose is less soluble than sucrose, except at high temperatures (>80° C.). Trehalose forms a rhomboid crystal as the dihydrate, and has 90% of the calorific content of sucrose in that form. Anhydrous forms of trehalose readily regain moisture to form the dihydrate. Trehalose has also been used in at least one biopharmaceutical formulation, the monoclonal antibody transtuzumab, marketed as Herceptin. It has a solubility of 68.9 g/100 g $H_2O$ at 20° C.

TABLE 6

Parameters of nanoparticles (NPs) self-assembled by TMC polymers with different degrees of quaternization.

| | Mean Particle Size (nm) | Zeta Potential (mV) | Polydispersity Index |
|---|---|---|---|
| CS/γ-PGA NPs | | | |
| pH 1.2 | N/A | N/A | 1 |
| pH 2.0 | N/A | N/A | 1 |
| pH 2.5 | 113.3 ± 1.6 | 38.6 ± 0.8 | 0.14 ± 0.01 |
| pH 6.0 | 104.1 ± 1.2 | 36.2 ± 2.5 | 0.11 ± 0.02 |
| pH 6.6 | 245.6 ± 4.5 | 12.9 ± 0.4 | 0.17 ± 0.11 |
| pH 7.0 | N/A | N/A | 1 |
| pH 7.4 | N/A | N/A | 1 |
| TMC25/γ-PGA NPs | | | |
| pH 1.2 | N/A | N/A | 1 |
| pH 2.0 | N/A | N/A | 1 |
| pH 2.5 | 396.4 ± 4.7 | 32.1 ± 1.6 | 0.32 ± 0.11 |
| pH 6.0 | 101.3 ± 3.1 | 30.9 ± 2.1 | 0.13 ± 0.04 |
| pH 6.6 | N/A | N/A | 1 |
| pH 7.0 | N/A | N/A | 1 |
| pH 7.4 | N/A | N/A | 1 |
| TMC40/γ-PGA NPs | | | |
| pH 1.2 | N/A | N/A | 1 |
| pH 2.0 | N/A | N/A | 1 |
| pH 2.3 | 272.2 ± 2.3 | 38.6 ± 2.7 | 0.25 ± 0.23 |
| pH 2.5 | 252.4 ± 3.5 | 35.4 ± 1.1 | 0.21 ± 0.04 |
| pH 6.0 | 106.3 ± 2.3 | 32.3 ± 2.1 | 0.15 ± 0.14 |
| pH 6.6 | 238.3 ± 3.1 | 24.3 ± 1.4 | 0.09 ± 0.03 |
| pH 7.0 | 296.7 ± 4.7 | 20.4 ± 0.3 | 0.18 ± 0.11 |
| pH 7.4 | 498.4 ± 6.8 | 17.3 ± 0.6 | 0.38 ± 0.21 |
| TMC55/γ-PGA NPs | | | |
| pH 1.2 | N/A | N/A | 1 |
| pH 2.0 | 252.5 ± 4.1 | 35.6 ± 4.2 | 0.16 ± 0.08 |
| pH 2.5 | 221.4 ± 3.5 | 32.5 ± 3.4 | 0.15 ± 0.02 |
| pH 6.0 | 114.6 ± 2.3 | 30.6 ± 3.8 | 0.12 ± 0.03 |
| pH 6.6 | 141.2 ± 1.6 | 24.8 ± 3.4 | 0.15 ± 0.02 |
| pH 7.0 | 144.6 ± 4.8 | 20.4 ± 1.7 | 0.18 ± 0.14 |
| pH 7.4 | 141.2 ± 0.9 | 18.9 ± 4.1 | 0.11 ± 0.11 |

N/A: Precipitation of aggregates was observed.

Mannitol or hexan-1,2,3,4,5,6-hexyl ($C_6H_8(OH)_6$) is an osmotic diuretic agent and a weak renal vasodilator. Chemically, mannitol is a sugar alcohol, or a polyol; it is similar to xylitol or sorbitol. However, mannitol has a tendency to lose a hydrogen ion in aqueous solutions, which causes the solution to become acidic. For this reason, it is not uncommon to add a substance to adjust its pH, such as sodium bicarbonate. Mannitol has a chemical formula $C_6H_{14}O_6$. It is listed as CAS no. 69-65-8 and PubChem 453. The molecular-structure for mannitol is shown below.

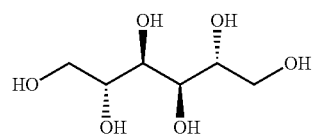

Glycerol is a chemical compound with the formula $HOCH_2CH(OH)CH_2OH$. This colorless, odorless, viscous liquid is widely used in pharmaceutical formulations. Commonly called glycerin or glycerine, it is a sugar alcohol and is fittingly sweet-tasting with low toxicity. Glycerol has three hydrophilic alcoholic hydroxyl groups that are responsible for its solubility in water and its hygroscopic nature. Glycerol has a chemical formula as $C_3H_5(OH)_3$. It is listed as CAS no. 56-81-5. The molecular structure for glycerol is shown below.

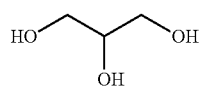

Example No. 18

Freeze-Drying Process for Nanoparticles

Each nanoparticles (at 2.5% concentration) were mixed with a solution of four types of liquid at a 1:1 volume ratio for about 30 minutes until fully dispersed. The mixed particle-liquid was then freeze-dried under a lyophilization condition, for example, at about −80° C. and <25 mmHg pressure for about 6 hours. The parameters in a selected lyophilization condition may vary slightly from the aforementioned numbers. The four types of liquid used in the experiment include: (A) DI water; (B) trehalose; (C) mannitol; and (D) glycerol, whereas the concentration of the liquid (A) to liquid (C) in the solution was set at 2.5%, 5% and 10%. After a freeze-drying process, the mixed particle-liquid was rehydrated with DI water at a 1:5 volume ratio to assess the integrity of nanoparticles in each type of liquid. The results are shown in Table 7. By comparing the particle size, polydispersity index, and zeta-potential data, only the nanoparticles from the freeze-dried particle-trehalose runs (at 2.5%, 5%, and 10% concentration level) show comparable properties to those of the pre-lyophilization nanoparticles. Under the same data analysis, the nanoparticles from the freeze-dried particle-mannitol runs (at 2.5%, and 5% concentration level) show somewhat comparable properties to those of the pre-lyophilization nanoparticles.

Figure 16:
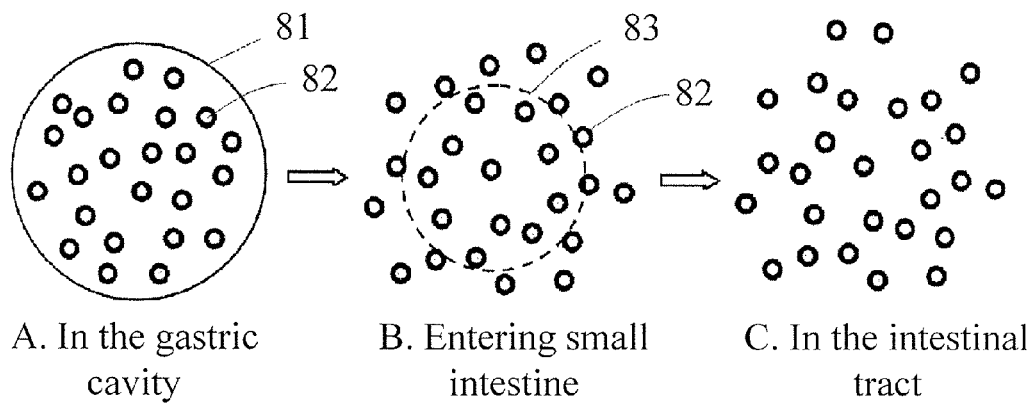
FIG. 16 A-C show a proposed mechanism of nanoparticles released from the enteric coated capsules.

FIG. 16 shows an illustrative mechanism of nanoparticles released from the enteric-coated capsules. FIG. 16(A) shows the phase where nanoparticles are in the gastric cavity, wherein the freeze-dried nanoparticles 82 are encapsulated within an initial enteric coating or coated capsule 81. FIG. 16(B) shows a schematic of the nanoparticles during the phase of entering small intestine, wherein the enteric coat and its associated capsule starts to dissolve 83 and a portion of nanoparticles 82 is released from the capsule and contacts fluid. FIG. 16(C) shows the phase of nanoparticles in the intestinal tract, wherein the nanoparticles revert to a wet state having chitosan at its surface. In an alternate embodiment, nanoparticles may be released from alginate-calcium coating. In preparation, nanoparticles are first suspended in a solution that contains calcium chloride, wherein the calcium ions are positively charged. With a pipette, alginate with negatively charged carboxyl groups is slowly added to the calcium chloride solution. Under gentle stirring, the alginate-calcium starts to conjugate, gel, and coat on the nanoparticle surface. In simulated oral administration of the alginate-calcium coated nanoparticles, nanoparticles start to separate from the coating when they enter the small intestines.

Example No. 19

Freeze-Dried Nanoparticles in Animal Evaluation

In the in vivo study, rats as prepared and conditioned according to Example no. 10 were used in this evaluation. In the animal evaluation study, diabetic rats fasted for 12 hours and were then subjected to three different conditions: (a) oral deionized water (DI) administration as negative control; (b) oral insulin-loaded lyophilized nanoparticles administration, whereas the nanoparticles have an insulin loading content of 4.4% with an insulin loading efficiency of 48.6% and are loaded in a capsule with a surface enteric coating; and (c) subcutaneous (SC) insulin injection at 5 U/kg as positive control. The blood glucose concentration from rat's tail was measured over time.

TABLE 7

Properties of nanoparticles before and after an exemplary freeze-drying process.

(Table 7A: before a freeze-drying process
NPs solution

| Conc. | 2.50% |
|---|---|
| Size (mm) | 2.66 |
| Kcps | 352.2 |
| PI | 0.291 |
| Zeta Potential | 25.3 |

(Table 7B: after a freeze-drying process)

| | A: DI Water DI water + NPs | B: Trehalose Trehalose + NPs (volume 1:1) | | | C: Mannitol Mannitol + NPs (volume 1:1) Conc. | | D: Glycerol Glycerol + NPs (volume 1:1) | | |
|---|---|---|---|---|---|---|---|---|---|
| | (volume 1:1) | 2.50% | 5.00% | 10.00% | 2.50% | 5.00% | 2.50% | 5.00% | 10.00% |
| Size (mm) | 9229.1 | 302.4 | 316.7 | 318.9 | 420.1 | 487.5 | 6449.1 | 7790.3 | 1310.5 |
| Kcps | 465.3 | 363.7 | 327.7 | 352.2 | 305.4 | 303.7 | 796.1 | 356.1 | 493.3 |
| PI | 1 | 0361 | 0.311 | 0.266 | 0.467 | 0.651 | 1 | 1 | 1 |
| Zeta Potential | | 25.6 | 24.6 | 24.7 | 24.4 | 25.3 | | | |

Figure 17:
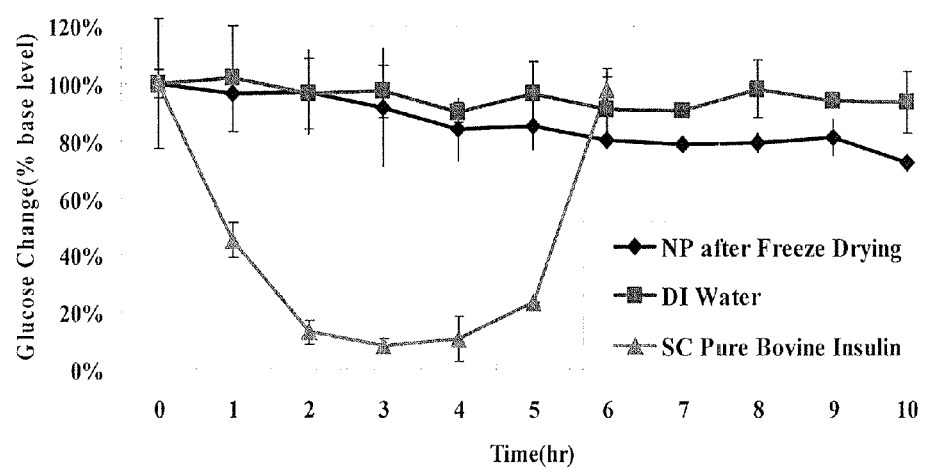
FIG. 17 shows the effect of orally administered insulin-loaded nanoparticles on 'glucose reduction %' in diabetic rats, wherein the freeze-dried nanoparticles were loaded in an enterically coated capsule upon delivery.

FIG. 17 shows glucose change (hypoglycemic index) versus time of the in vivo animal study (n=5). The glucose change as a percentage of base lines for oral DI administration (control) over a time interval of 10 hours appears relatively constant within the experimental measurement error range. As anticipated, the glucose decrease for the SC insulin injection method is evident in rat blood at a very early time interval starts to taper off after 2 hours, and ends at about 6 hours in this exemplary study. The most important observation of the study comes from the oral administration route with insulin-loaded lyophilized (namely, freeze-dried) nanoparticles. Nanoparticles of this example have an insulin LC at 4.4%, whereas nanoparticles from Example no. 10 had an insulin LC at 14.1% in FIG. 14). With the same amount of nanoparticles in both examples, the insulin-feeding ratio of Example no. 19 to Example no. 10 is about 1:3. In other words, the insulin fed to a rat in this study from nanoparticles is about ⅓ of the insulin from nanoparticles fed to rats in Example no. 10.

The blood glucose begins to decrease from the base line at about 3 hours after administration and sustains a lower glucose level for more than 10 hours into study. It implies that the current insulin-loaded nanoparticles may modulate the glucose level in animals in a sustained or prolonged effective mode. Some aspects of the invention provide a method of treating diabetes of an animal subject comprising orally administering insulin-containing nanoparticles with a dosage effective amount of the insulin to treat the diabetes, wherein at least a portion of the nanoparticles comprises a positively charged shell substrate and a negatively charged core substrate. In one embodiment, the dosage effective amount of the insulin to treat diabetes comprises an insulin amount of between about 15 units to 45 units per kilogram body weight of the animal subject, preferably 20 to 40 units, and most preferably at about 25 to 35 units insulin per kilogram body weight. In one embodiment, the lyophilized nanoparticles may be fed as-is to an animal without being loaded in an enterically coated capsule.

Example No. 20

Nanoparticles Loaded with Enhanced Insulin Loading

Figure 18:
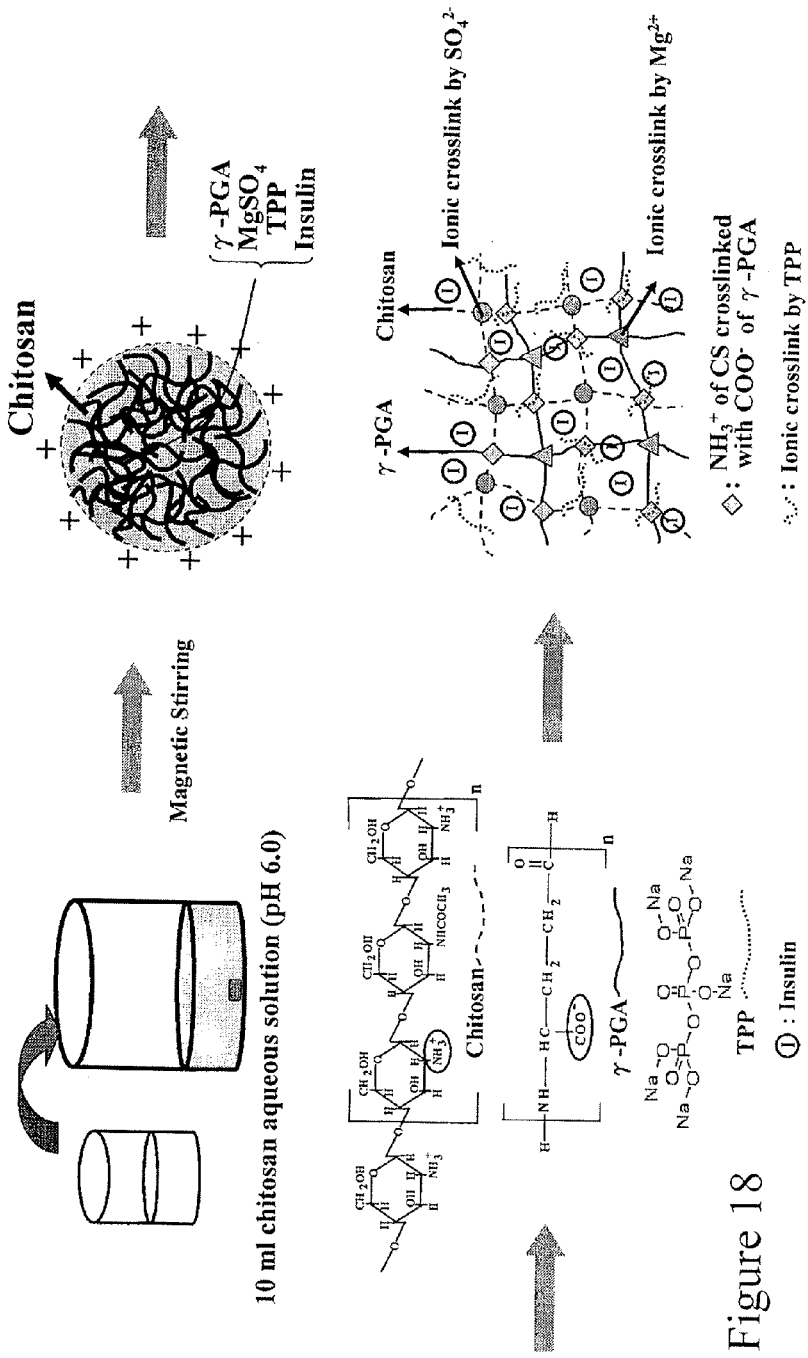
FIG. 18 shows insulin-loaded nanoparticles with a core composition consisted of γ-PGA, MgSO4, sodium tripolyphosphate (TPP), and insulin.

In a co-pending application, U.S. patent application Ser. No. 11/881,185 filed Jul. 26, 2007, entire contents of which are incorporated herein by reference, it is disclosed that a novel nanoparticle may comprise a shell substrate of chitosan and a core substrate consisting of at least one bioactive agent, MgSO$_4$, TPP, and a negatively charged substrate that is neutralized with chitosan in the core. FIG. 18 shows insulin-loaded nanoparticles with a core composition comprised of γ-PGA, MgSO$_4$, sodium tripolyphosphate (TPP), and insulin. Nanoparticles were obtained upon addition of core component, using a pipette (0.5-5 ml, PLASTIBRAND®, BrandTech Scientific Inc., Germany), into a CS aqueous solution (pH 6.0, 10 ml) at certain concentrations under magnetic stirring at room temperature. Nanoparticles were collected by ultracentrifugation at 38,000 rpm for 1 hour. Supernatants were discarded and nanoparticles were resuspended in deionized water for further studies. In one embodiment, nanoparticles are encapsulated in a gelcap, or are lyophilized before being loaded in a gelcap or in a tablet. The nanoparticles thus obtained via the simple and mild ionic-gelation method described herein show typical characteristics in a spheroidal configuration with a particle size of between about 50 to 400 nm, a positive surface charge and a narrow polydispersity index. The sodium tripolyphosphate has a chemical formula of Na$_5$P$_3$O$_{10}$ as shown below:

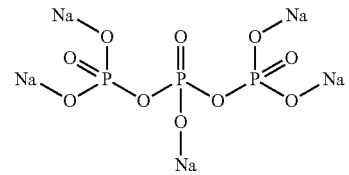

In the example, the core composition may be varied and evaluated with a preferred composition of 2 ml γ-PGA aqueous solution at pH 7.4 with insulin, MgSO$_4$ and TPP, resulting in a ratio of CS:γ-PGA:TPP:MgSO4:insulin=6.0:1.0:1.0:2.0: 0.05. Thus, the nanoparticles show characteristics as disclosed herein with a chitosan shell and a core composition consisting of γ-PGA, MgSO$_4$, TPP, and insulin and have an average loading efficiency of 72.8% insulin and an average loading content of 21.6% insulin.

In the enhanced drug loading of the present example, there provides two or more distinct ionic crosslink mechanisms. In one embodiment, the nanoparticles of the present invention may have a structure or matrix of interpenetrated ionic-crosslinks (that is, elongate ionic-crosslink chains) including a first ionic-crosslink chain of NH$_3^+$ of CS with COO$^-$ of γ-PGA, a second ionic-crosslink chain of NH$_3^+$ of CS with SO$_4^{2-}$ of MgSO$_4$, a third ionic-crosslink chain of Mg$^{2+}$ of MgSO$_4$ with COO$^-$ of γ-PGA, and/or a fourth ionic-crosslink chain of Na$_3$P$_3$O$_{10}^{2-}$ of TPP with NH$_3^+$ of CS or Mg$^{2+}$ of MgSO$_4$.

Some aspects of the invention relate to a nanoparticle composition for oral administration with an insulin loading efficiency and content at higher than 45% and 14% (preferably up to about 73% and 22%), respectively. The prepared nanoparticles (NPs) are stable at a pH range of 2.0 to 7.1. This broad range allows the chitosan-shelled nanoparticle to be temporarily stable in most of the intestine region (including duodenum, jejunum, and ileum) for enhanced membrane absorption and permeability of active ingredient (for example, insulin, exenatide or pramlintide). Some aspects of the invention provide a chitosan-shelled nanoparticle with a core composition of γ-PGA, MgSO$_4$, TPP, and at least one bioactive agent, such as insulin, exenatide, or pramlintide for treatment of diabetes. In an alternate embodiment, some aspects of the invention provide a chitosan-shelled nanoparticle with a core composition consisted of γ-PGA, MgSO$_4$, TPP, and at least one bioactive agent. In one embodiment, negatively charged γ-PGA may conveniently be substituted by another negatively charge substrate, such as heparin. In an experiment following the experimental conditions of Example no. 20 by substituting insulin with exenatide, chitosan-shelled nanoparticles with a core composition of γ-PGA, MgSO$_4$, TPP, and exenatide exhibit similar physical and mechanical properties compared to the ones with insulin.

Figure 19:
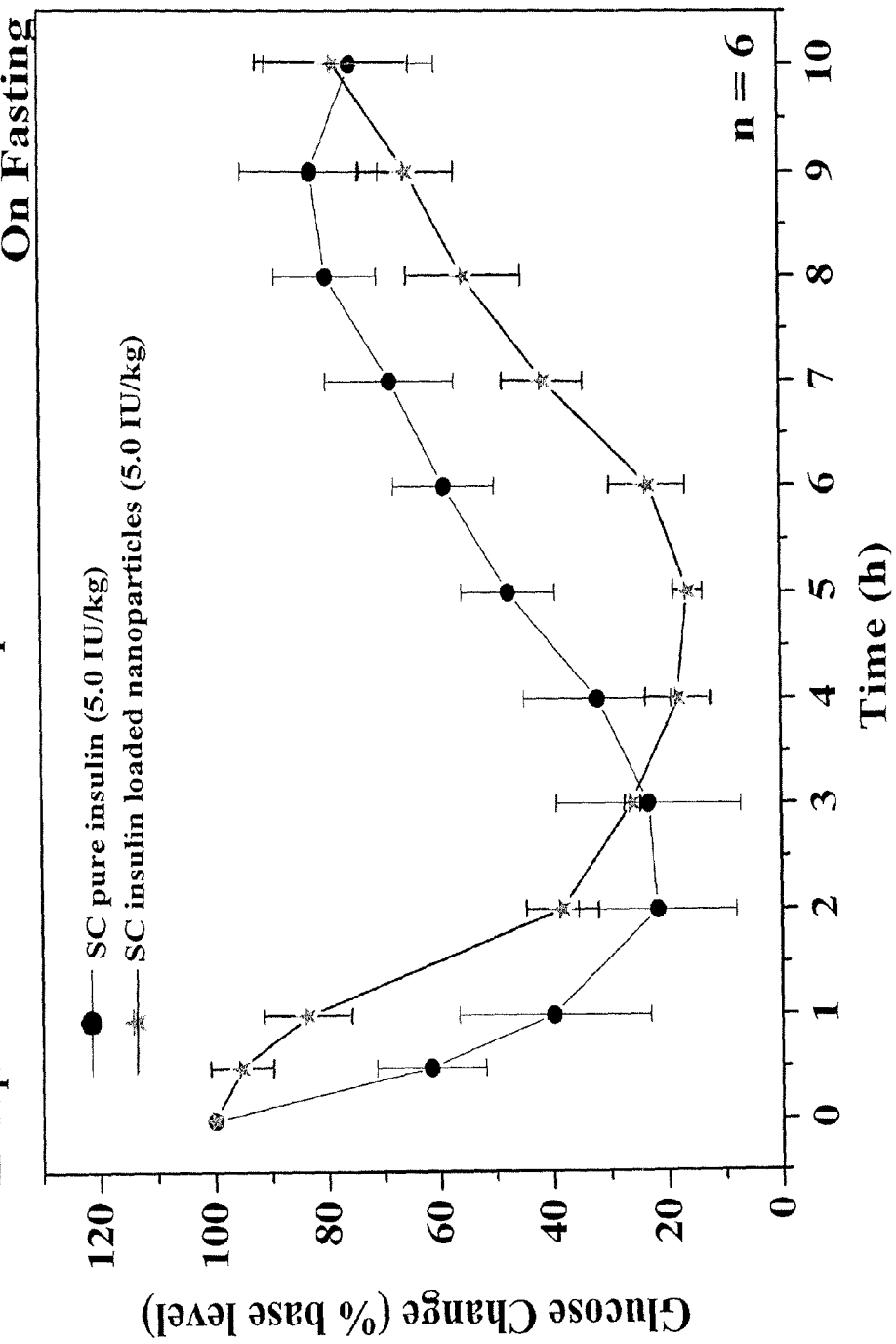
FIG. 19 shows an in vivo subcutaneous study using insulin injectables and insulin-containing nanoparticles.

FIG. 19 shows an in vivo subcutaneous study using insulin injectables and insulin-containing nanoparticles. The insulin-containing nanoparticles exhibit different pharmacodynamics and/or pharmacokinetics in a sustained releasing manner. Some aspects of the invention relate to a pharmaceutical composition of nanoparticles for subcutaneous or blood vessel administration in an animal subject, the nanoparticles comprising a shell portion that is dominated by positively charged chitosan, a core portion that contains negatively charged substrate, wherein the negatively charged substrate is at least partially neutralized with a portion of the positively charged chitosan in the core portion, and at least one bioactive agent loaded within the nanoparticles.

Some aspects of the invention relate to a method of delivering a bioactive agent to blood circulation in an animal subject, comprising: (a) providing nanoparticles according to a preferred embodiment of the pharmaceutical composition of the present invention, wherein the nanoparticles are formed via a simple and mild ionic-gelation method; (b) administering the nanoparticles orally toward the intestine of the animal subject via stomach; (c) urging the nanoparticles to be absorbed onto a surface of an epithelial membrane of the intestine via muco-adhesive chitosan-shelled nanoparticles; (d) permeating bioactive agent to pass through an epithelial barrier of the intestine; and (e) releasing the bioactive agent into the blood circulation. In one embodiment, the bioactive agent is selected from the group consisting of exenatide, pramlintide, insulin, insulin analog, and combinations thereof. In another embodiment, the bioactive agent permeates through the tight junctions of the epithelial membrane when chitosan-shelled nanooparticles break up and release the bioactive agent at vicinity of the tight junctions.

Some aspects of the invention relate to a method for inducing a redistribution of tight junctions' ZO-1 protein, leading to a translocation of the ZO-1 protein to the cytoskeleton that accompanies increased permeation in an animal subject, the method comprising administering bioactive nanoparticles into the animal subject with an effective dosage to induce the redistribution, wherein the bioactive nanoparticles comprise a shell substrate of chitosan and a core substrate that comprises poly(glutamic acid) and the bioactive agent that is selected from the group consisting of exenatide, pramlintide, insulin, insulin analog, and combinations thereof.

Nanoparticles Loaded with Tumor Necrosis Factor Inhibitors

Tumor necrosis factor (TNF) promotes an inflammatory response, which in turn causes many of the clinical problems associated with autoimmune disorders such as rheumatoid arthritis, ankylosing spondylitis, Crohn's disease psoriasis, and refractory asthma. These disorders are sometimes treated by using a TNF inhibitor. This inhibition can be achieved with a monoclonal antibody such as infliximab (Remicade) or adalimumab (Humira), or with a circulating receptor fusion protein such as etanercept (Enbrel). Another example is pentoxifylline.

This potential applicability of anti-TNF therapies in the treatment of rheumatoid arthritis (RA) is based on the recognition of the role of TNF-alpha is the "master regulator" of the inflammatory response in many organ systems. TNF and the effects of TNF are also inhibited by a number of natural compounds, including curcumin (a compound present in tumeric) and catechins (in green tea). Tumor necrosis factor-alpha (TNFα) is a cytokine produced by monocytes and macrophages, two types of white blood cells. It mediates the immune response by increasing the transport of white blood cells to sites of inflammation, and through additional molecular mechanisms that initiate and amplify inflammation.

Adalimumab (brand name HUMIRA) is a TNT inhibitor, after infliximab and etanercept, to be approved in the United States. Like infliximab and etanercept, adalimumab binds to TNFa, preventing it from activating TNF receptors. Adalimumab is constructed from a fully human momoclonal antibody, while infliximab is a mouse-human chimeric antibody, and etanercept is a TNF receptor-IgG fusion protein. TNFα inactivation has proven to be important in downregulating the inflammatory reactions associated with autoimmune diseases. As of 2008, adalimumab has been approved by the FDA for the treatment of rheumatoid arthritis, psoriatic arthritis, anky losing spondylitis, Crohn's disease, moderate to severe chronic psoriasis, and juvenile idiopathic arthritis.

Adalimumab has a chemical formula of $C_{6428}H_{9912}N_{694}O_{1987}S46$ and a molecular mass of 144190.3 g/mol. Humira (brand name is an abbreviation of "Human Monoclonal Antibody in Rheumatoid Arthritis") is marketed as a subcutaneously injected treatment, typically by the patient at home. It cannot be administered orally, because the digestive system would destroy the drug in its current state, unless the drug is encapsulated in nanoparticles of the present invention.

Etanercept (Enbrel) is a recombinant-DNA drug made by combining two proteins (a fusion protein). It links human soluble TNF receptor to the Fc component of human immunoglobulin G1 (IgG1) and acts as a TNF inhibitor. Etanercept has a chemical formula of $C_{2224}H_{3475}N_{621}O_{698}S36$ and a molecular mass of 51234.9 g/mol. Etanercept binds to TNFα and decreases its role in disorders involving excess inflammation in humans and other animals, including autoimmune diseases such as ankylosing spondylitis, juvenile rheumatoid arthritis, psoriasis, psoriatic arthritis, rheumatois arthritis, and, potentially a variety of other disorders mediated by excess TNFα.

Infliximab (brand name Remicade) is a drug used to treat autoimmune disorders. Infliximab is known as a "chimeric monoclonal antibody" (the term "chimeric" refers to the use of both mouse (murine) and human components of the drug (i.e. murine binding $F_{ab}$ domains and human constant $F_c$ domains). The drug blocks the action of the pleiotropic proinflammatory TNFα (tumor necrosis factor alpha) by binding to it and preventing it from signaling the receptors for TNFα on the surface of cells. TNFα is one of the key cytokines that triggers and sustains the inflammation response.

Remicade is administered by intravenous infusion, typically at 6-8 week intervals, and at a clinic or hospital. It cannot be administered orally, because the digestive system would destroy the drug unless it is encapsulated in nanoparticles of the present invention. Infliximab neutralizes the biological activity of TNFa by binding with high affinity to the soluble (free floating in the blood) and transmembrane (located on the outer membranes of T cells and similar immune cells) forms of TNFα and inhibits or prevents the effective binding of TNFα with its receptors.

Remicade and Humira (another TNF antagonist) are in the subclass of "anti-TNF antibodies" (they are in the form of naturally occurring antibodies), and are capable of neutralizing all forms (extracellular, transmembrabe, and receptor-bound) of TNF alpha. Enbrel, a third TNF antagonist, is in a different subclass (receptor-construct fusion protein), and, because of its modified form, cannot neutralize receptor-bound TNFα. Additionally, the anti-TNF antibodies Humira and Remicade have the capability of Lysing cells involved in the inflammatory process, whereas the receptor fusion protein apparently lacks this capability. Although the clinical significance of these differences has not been absolutely proven, they may account for the discrepancies of these drugs in both efficacy and side effects.

Infliximab has high specificity for TNFα, and does not neutralize TNF beta (INFβ, also called lymphotoxin a), a related but less inflammatory cytokine that utilizes the same receptors as TNFα. Biological activities that are attributed to TNFα include: induction of proinglammatory cytokines such as interleukin (IL-1 and IL-6), enhancement of leukocyte movement or migration from the blood vessels into the tissues by increasing the permeability of endothelial layer of blood vessels; and increasing the release of adhesion molecules.

Infliximab prevents disease in transgenic mice (a special type of mice that are biologically engineered to produce a human form of TNFα and are used to test these drugs for results that might be expected in humans). These experimental mice develop arthritis as a result of their production of human TNFα, and when administered after disease onset, infliximab allows eroded joints to heal.

Infliximab has a chemical formula $C_{6428}H_{9912}N_{1694}O_{1987}S46$ and a molecular mass of 144190.3 g/mol. REMICADE (infliximab) is an advanced treatment that has been shown to have substantial benefits in patients with a number of inflammatory disorders involving the immune system. REMICADE targets specific proteins in the body's immune system to help control the development of inflammation, significantly reducing painful symptoms in diseases such as plaque psoriasis, rheumatoid arthritis, psoriatic arthritis, adult Crohn's disease, pediatric Crohn's disease, ulcerative colitis, and ankylosing spondylitis.

REMICADE is a type of protein that recognizes, attaches to, and blocks the action of a substance in the body called tumor necrosis factor (TNF). TNF is made by certain blood cells in the body. REMICADE will not cure plaque psoriasis, rheumatoid arthritis, psoriatic arthritis, adult Crohn's disease, pediatric Crohn's disease, ulcerative colitis, and ankylosing spondylitis, but blocking TNF may reduce the inflammation caused in the body.

Some aspects of the invention relate to a method of reducing inflammatory response caused by tumor necrosis factor in an animal subject, the method comprising orally administering nanoparticles composed of a TNF inhibitor, chitosan, and a core substrate of poly(glutamic acid) or heparin. In one embodiment, the inhibitor can be a momoclonal antibody such as infliximab (Remicade) or adalimumab (Humira), or a circulating receptor fusion protein such as etanercept (Enbrel).

In one embodiment, a TNF inhibitor nanoparticle formulation consisting of at least one inhibitor selected from the group consisting of infliximab, adalimumab and etanercept, chitosan, and one core negatively charged substrate of poly (glutamic acid) or heparin.

Nanoparticles Loaded with Bacteriophage

A bacteriophage is any one of a number of viruses that infect bacteria. The term is commonly used in its shortened form, phage. Typically, bacteriophages consist of an outer protein hull enclosing genetic material. The genetic material can be ssRNA, dsRNA, ssDNA, or dsDNA ('ss-' or 'ds-' prefix denotes single strand or double strand) between 5 and 500 kilo nucleotides long with either circular or linear arrangement. Bacteriophages are much smaller than the bacteria they destroy—usually between 20 and 200 nm in size.

Phages are estimated to be the most widely distributed and diverse entities in the biosphere. Phages are ubiquitous and can be found in all reservoirs populated by bacterial hosts, such as soil or the intestines of animals. One of the densest natural sources for phages and other viruses is sea water, where up to $9 \times 10^8$ virions per milliliter have been found in microbial mats at the surface, and up to 70% of marine bacteria may be infected by phages. They have been used for over 60 years as an alternative to antibiotics in the former Soviet Union and Eastern Europe. They are seen as a possible therapy against multi drug resistant strains of many bacteria.

To enter a host cell, bacteriophages attach to specific receptors on the surface of bacteria, including lipopolysaccharides, teichoic acids, proteins, or even flagella. This specificity means that a bacteriophage can only infect certain bacteria bearing receptors that they can bind to, which in turn determines the phage's host range. As phage virions do not move independently, they must rely on random encounters with the right receptors when in a solution (blood, lymphatic circulation, irrigation, soil water etc.).

Complex bacteriophages use a syringe-like motion to inject their genetic material into the cell. After making contact with the appropriate receptor, the tail fibers bring the base plate closer to the surface of the cell. Once attached completely, the tail contracts, possibly with the help of ATP present in the tail, injecting genetic material through the bacterial membrane.

Within minutes, bacterial ribosomes start translating viral mRNA into protein. For RNA-based phages, RNA replicase is synthesized early in the process. Proteins modify the bacterial RNA polymerase so that it preferentially transcribes viral mRNA. The host's normal synthesis of proteins and nucleic acids is disrupted, and it is forced to manufacture viral products instead. These products go on to become part of new virions within the cell, helper proteins which help assemble the new virions, or proteins involved in cell lysis.

Phages may be released via cell lysis, by extrusion, or, in a few cases, by budding. Lysis, by tailed phages, is achieved by an enzyme called endolysin which attacks and breaks down the cell wall peptidoglycan. An altogether different phage type, the filamentous phages, causes the host cell to continually secrete new virus particles. Released virions are described as free and unless defective are capable of infecting a new bacterium. Budding is associated with certain *Mycoplasma* phages. In contrast to virion release, phages displaying a lysogenic cycle do not kill the host but rather become long-term residents as prophage.

In August, 2006 the United State Food and Drug Administration (FDA) approved using bacteriophages on cheese to kill the *Listeria monocytogenes* bacteria, giving them GRAS status (Generally Recognized As Safe). In July 2007, the same bacteriophages were approved for use on all food products.

Some aspects of the invention relate to a method of mitigating bacteria in an animal subject, the method comprising orally administering nanoparticles composed of at least one bacteriophage, chitosan, and a core substrate of poly (glutamic acid) or heparin. One aspect of the invention relates to a bactericide nanoparticle formulation comprising at least one bacteriophage, chitosan, and a core substrate of poly (glutamic acid) or heparin. In one embodiment, a bactericide nanoparticle formulation consisting of at least one bacteriophage, chitosan, and one core negatively charged substrate of poly(glutamic acid) or heparin. In a further embodiment, the nanoparticles are encapsulated in capsules, wherein the capsules may be treated with an enteric coating polymer. In one embodiment, the capsules further comprise a permeation enhancer, wherein the permeation enhancer is selected from the group consisting of $Ca^{2+}$ chelators, bile salts, anionic surfactants, medium-chain fatty acids, phosphate esters, chitosan, and chitosan derivatives. In another embodiment, the capsule may contain solubilizer such as GRAS or other pharmacopoeial excipients.

Example No. 21

Nanoparticles Loaded with Pemetrexed

Pemetrexed (brand name Alimta®) is a chemotherapy drug manufactured and marketed by Eli Lilly and Company. Its indications are the treatment of pleural mesothekuoma as well as non-small cell lung cancer. Pemetrexed has a systematic (IUPAC) name 2-[4-[2-(4-amino-2-oxo-3,5,7-triazabicyclo[4.3.0]nona-3,8,10-trien-9-yl)ethyl]benzoyl]aminopentanedioic acid, a chemical formula $C_{20}H_{21}N_5O_6$ and a molecular mass of 427.411 g/mol. Pemetrexed is chemically similar to folic acid and is in the class of chemotherapy drugs called folate antimetabolites. It works by inhibiting three enzymes used in purine and pyrimidine synthesis-thymidylate synthase (TS), dihydrofolate reductase (DHFR), and glycinamide ribonucleotide formyltransferase (GARFT). By inhibiting the formation of precursor purine and pyrimidine nucleotides, pemetrexed prevents the formation of DNA and RNA, which are required for the growth and survival of both normal cells and cancer cells. In February 2004, the Food and Drug Administration approved pemetrexed for treatment of malignant pleural mesothelioma, a type of tumor of the lining of the lung, in combination with cisplatin. In September 2008, the FDA granted approval as a first-line treatment, in combination with cisplatin, against of locally-advanced and metastatic non-small cell lung cancer, or NSCLC, in patients with non-squamous histology. Trials are currently testing it against esophagus and other cancers.

In one exemplary preparation, nanoparticles were obtained upon addition of a mixture of γ-PGA plus pemetrexed aqueous solution (2 ml), using a pipette (0.5-5 ml, PLASTIBRAND®, BrandTech Scientific Inc., Germany), into a low-MW CS aqueous solution (pH 6.0, 10 ml) at concentrations higher than 0.10% by w/v under magnetic stirring at room temperature to ensure positive surface charge. Nanoparticles were collected by ultracentrifugation at 38,000 rpm for 1 hour. Pemetrexed is wholly or substantially totally encapsulated within the nanoparticles. Supernatants were discarded and nanoparticles were resuspended in deionized water as the solution products, further encapsulated in capsules/enteric capsules or further treated with lyophilization freeze-dried process. The nanoparticles thus obtained via the simple and mild ionic-gelation method described herein show typical characteristics in a spheroidal configuration with a particle size of between about 50 to 400 nm, a positive surface charge and a narrow polydispersity index.

Epirubicin is an anthracycline drug used for chemotherapy. It is marketed by Pfizer under the trade name Ellence in the U.S. and Pharmorubicin or Epirubicin elsewhere. Similarly to other anthracyclines, epirubicin acts by intercalating DNA strands. Intercalation results in complex formation that inhibits DNA and RNA synthesis. It also triggers DNA cleavage by topoisomerase II, resulting in mechanisms that lead to cell death. Binding to cell membranes and plasma proteins may be involved in the compound's cytotoxic effects. Epirubicin also generates free radicals that cause cell and DNA damage. Epirubicin is favored over doxorubicin, the most popular anthracycline, in some chemotherapy regimens as it appears to cause fewer side-effects. Epirubicin has a different spatial orientation of the hydroxyl group at the 4' carbon of the sugar, which may account for its faster elimination and reduced toxicity. Epirubicin is primarily used against breast and ovarian cancer, gastric cancer, lung cancer, and lymphomas. Its systematic (IUPAC) name is 10-(4-amino-5-hydroxy-6-methyl-oxan-2-yl)oxy-6,8,11-trihydroxy-8-(2-hydroxyacetyl)-1-methoxy-9,10-dihydro-7H-tetracene-5,12-dione. The chemical formula is $C_{27}H_{29}NO_{11}$ with a molecular mass 543.519 g/mol.

Irinotecan is a chemotherapy agent that is a topoisomerase 1 inhibitor. Chemically, it is a semisynthetic analogue of the natural alkaloid camptothecin. Its main use is in colon cancer, particularly in combination with other chemotherapy agents. Irinotecan was first introduced in Japan by the Pharmaceutical arm of Yakult Honsha as Campto. In 1994, it received accelerated FDA approval in the United States, where it is now marketed by Pfizer as Camptosar. It is also known as CPT-11. Its systematic (IUPAC) name is (S)-4,11-diethyl-3,4,12,14-tetrahydro-4-hydroxy-3,14-dioxolH-pyrano[3',4':6,7]-indolizino[1,2-b]quinolin-9-yl-[1,4'bipiperidine]-1'-carboxylate. It has a chemical formula $C_{33}H_{38}N_4O_6$ with a molecular mass 677.185 g/mol (hydrochloride). Irinotecan is activated by hydrolysis to SN-38, an inhibitor of topoisomerase I. This is then inactivated by glucuronidation by uridine diphosphate glucoronosyltransferase 1A1 (UGT1A1). The inhibition of topoisomerase I by the active metabolite SN-38 eventually leads to inhibition of both DNA replication and transcription.

Example No. 22

Nanoparticles Loaded with Gemcitabine

Gemcitabine is a nucleoside analog used as chemotherapy. It is marketed as Gemzar® by Eli Lilly and Company. Gemcitabine has a systematic (IUPAC) name as 4-amino-1-[3,3-difluoro-4-hydroxy-5-(hydroxymethyl)tetrahydrofuran-2-yl]-1H-pyrimidin-2-one. Gemcitabine has a chemical formula $C_9H_{11}F_2N_3O_4$ and a molecular mass of 263.198 g/mol. Gemcitabine is used in various carcinomas: non-small cell lung cancer, pancreatic cancer, bladder cancer and breast cancer. It is being investigated for use in oesophageal cancer, and is used experimentally in lymphomas and various other tumor types. Gemcitabine represents an advance in pancreatic cancer care. It is also not as debilitating as other forms of chemotherapy. A study reported in the Journal of the American Medical Association suggested that gemcitabine shows benefit in patients with pancreatic cancer who were considered to have successful tumor resections. GemCarbo chemotherapy (consisting of gemcitabine, as known as Gemzar and Carboplatin, which are both colourless fluids) is used to treat several different types of cancer, but most commonly lung cancer.

In one exemplary preparation, nanoparticles were obtained upon addition of a mixture of γ-PGA and gemcitabine aqueous solution (2 ml), using a pipette (0.5-5 ml, PLASTIBRAND®, BrandTech Scientific Inc., Germany), into a low-MW CS aqueous solution (pH 6.0, ml) at concentrations higher than 0.10% by w/v under magnetic stirring at room temperature to ensure positive surface charge. Nanoparticles were collected by ultracentrifugation at 38,000 rpm for 1 hour. Gemcitabine is wholly or substantially totally encapsulated within the nanoparticles. Supernatants were discarded and nanoparticles were resuspended in deionized water as the solution products, further encapsulated in capsules/enteric capsules or treated with lyophilization freeze-dried process. The nanoparticles thus obtained via the simple and mild ionic-gelation method described herein show typical characteristics in a spheroidal configuration with a particle size of between about 50 to 400 nm, a positive surface charge, and a narrow polydispersity index.

Example No. 23

Nanoparticles Loaded with Drotrecogin Alfa (Activated)

Drotrecogin alfa (activated) (Xigris®, marketed by Eli Lilly and Company) is a recombinant form of human activated protein C that has anti-thrombotic, anti-inflammatory, and profibrinolytic properties. Drotrecogin alpha (activated) belongs to the class of serine proteases. It is used mainly in intensive care medicine as a treatment for severe sepsis. Drotrecogin alpha (activated) has a systematic (IUPAC) name as Activated human protein C; it has a chemical formula $C_{1786}H_{2779}N_{509}O_{519}S_{29}$ and a molecular mass of 55000 g/mol. The specific mechanism by which drotrecogin exerts its effect on survival in patients with severe sepsis is not completely understood. In vitro data suggest that activated protein C exerts an antithrombotic effect by inhibiting factors Va and VIIIa, and that it has indirect profibrinolytic activity by inhibiting plasminogen activator inhibitor-1 (PAI-1). In vitro data also suggest that activated protein C may exert an anti-inflammatory effect by inhibiting tumor nectosis factor production, by blocking leukocyte adhesion to selectins, and by limiting the thrombin-induced inflammatory responses within the microvascular endothelium. If the i.v. dosage guidelines are followed, the drug reaches peak plasma levels after two hours and is completely cleared from plasma two hours after the termination of the infusion period. Endogenous plasma protease inhibitors deactivate drotrecogin. Therefore, no dosage adjustment is needed in elderly patients, or in patients with renal or hepatic dysfunction. Drotrecogin is indicated for the reduction of mortality in adult patients with severe sepsis (sepsis associated with acute organ dysfunction) who have a high risk of death.

In one exemplary preparation, nanoparticles were obtained upon addition of a mixture of γ-PGA and drotrecogin alpha (activated) aqueous solution (2 ml), using a pipette (0.5-5 ml, PLASTIBRAND®, BrandTech Scientific Inc., Germany), into a low-MW CS aqueous solution (pH 6.0, ml) at concentrations higher than 0.10% by w/v under magnetic stirring at room temperature to ensure positive surface charge. Nanoparticles were collected by ultracentrifugation at 38,000 rpm for 1 hour. Drotrecogin alpha (activated) is wholly or substantially totally encapsulated within the nanoparticles. Supernatants were discarded and nanoparticles were resuspended in deionized water as the solution products. Then they were either encapsulated in capsules/enteric capsules or treated with lyophilization freeze-dried process. The nanoparticles thus obtained via the simple and mild ionic-gelation method described herein show typical characteristics in a spheroidal configuration with a particle size of between about 50 to 400 nm, a positive surface charge and a narrow polydispersity index.

Factor IX (or Christmas factor) is one of the serine proteases of the coagulation system; it belongs to peptidase family S1. Deficiency of this protein causes hemophilia B. Factor IX is inactive unless activated by factor XIa (of the contact pathway) or factor VIIa (of the tissue factor pathway). When activated into factor IXa, it acts by hydrolysing one arginine-isoleucine bond in factor X to form factor Xa. It requires calcium, membrane phospholipids, and factor VIII as cofactors to do so. Factor IX complex is currently via injectable routes. Its generic name is Factor IX, human recombinant-injection. In use, Factor IX is a part of blood needed for clotting which stops bleeding. Persons with low Factor levels are at risk for bleeding. This medication is used to prevent or control bleeding episodes in persons with low Factor levels (hemophilia, Christmas disease). It is also used to reverse the effects of warfarin blood thinner. Factor IX has been incorporated in the nanoparticle formulation via the simple and mild ionic-gelation method described herein, the nanoparticles thus obtained show typical characteristics in a spheroidal configuration with a particle size of between about 50 to 400 nm, a positive surface charge and a narrow polydispersity index.

Example No. 24

Nanoparticles Loaded with Humatrope

Humatrope® (somatotropin or somatropin) is a polypeptide hormone of rDNA origin. Manufactured by Eli Lilly and Company, it is used to stimulate linear growth in pediatric patients who lack adequate normal human growth homone. It has 191 amino acid residues and a molecular weight of 22,125 daltons. Its amino acid sequence is identical to that of human growth hormone of pituitary origin (anterior lobe). Humatrope is synthesized in a strain of *E. coli* modified by the addition of a gene for human growth hormone. Other Human growth homone produced from rDNAs include; Omnitrope (Sandoz), Nutropin, Norditropin, Genotropin® (Pfizer.

In one exemplary preparation, nanoparticles were obtained upon addition of a mixture of γ-PGA and Humatrope aqueous solution (2 ml), using a pipette (0.5-5 ml, PLASTIBRAND®, BrandTech Scientific Inc., Germany), into a low-MW CS aqueous solution (pH 6.0, 10 ml) at concentrations higher than 0.10% by w/v under magnetic stirring at room temperature to ensure positive surface charge. Nanoparticles were collected by ultracentrifugation at 38,000 rpm for 1 hour. Humatrope is wholly or substantially totally encapsulated within the nanoparticles. Supernatants were discarded and nanoparticles were resuspended in deionized water as the solution products, further encapsulated in capsules/enteric capsules or treated with lyophilization freeze-dried process. The nanoparticles thus obtained via the simple and mild ionic-gelation method described herein show typical characteristics in a spheroidal configuration with a particle size of between about 50 to 400 nm, a positive surface charge, and a narrow polydispersity index.

The major isoform of the human growth hormone (GH) is a protein of 191 amion acids and a molecular weight of 22124 daltons. The structure includes four helices necessary for functional interaction with the GH receptor. GH is structurally and apparently evolutionarily homologous to prolactin and chorionic somatomammotropin. Despite marked structural similarities between growth hormone from different species, only human and primate growth hormones have significant effects in humans. Effects of growth hormone on the tissues of the body can generally be described as anabolic (building up). Like most other protein hormones, GH acts by interacting with a specific receptor on the surface of cells. In one aspect, GH stimulating the increase in height in childhood is the most widely known effect of GH, and appears to be caused by at least two mechanisms. In another aspect, because polypeptide hormones are not fat soluble, they cannot penetrate sarcolemma. Thus, GH exerts some of its effects by binding to receptors on target cells, where it activates a secondary messenger. Through this mechanism, GH directly stimulates division and multiplication of chondrocytes of cartilage. These are the primary cells in the growing ends (epiphyses) of children's long bones.

GH also stimulates production of insulin-like growth factor 1 (IGF-1, formerly known as somatomedin C), a hormone homologous to proinsulin. The liver is a major target organ of GH for this process, and is the principal site of IGF-1 production. IGF-1 has growth-stimulating effects on a wide variety of tissues. Additional IGF-1 is generated within target tissues, making it apparently both an endocrine and an autocrine/paracrine hormone. IGF-1 also has stimulatory effects on osteoblast and chondrocyte activity to promote bone growth. In addition to increasing height in children and adolescents, growth hormone has many other effects on the body, such as: increasing calcium retention, and strengthening and increasing the mineralization of bone; increasing muscle mass through sarcomere hyperplasia; promoting lipolysis; increasing protein synthesis; stimulating the growth of all internal organs excluding the brain; playing a role in fuel homeostasis; reducing liver uptake of glucose; promoting gluconeogenesis in the liver; contributing to the maintenance and function of pancreatic islets; and stimulating the immune system.

Pegylation and Pegylated Bioactive Agents

Pegylation is the process of covalent attachment of polyethylene glycol polymer chains to another molecule, normally a drug or therapeutic protein or bioactive agent (i.e., pegylated bioactive agent) or chitosan (i.e., PEG-CS). Pegylation is routinely achieved by incubation of a reactive derivative of PEG with the target macromolecule. The covalent attachment of PEG to a drug or therapeutic protein can "mask" the agent from the host's immune system (reduced immunogenicity and antigenicity), increase the hydrodynamic size (size in solution) of the agent which prolongs its circulatory time by reducing renal clearance. Pegylation can also provide water solubility to hydrophobic drugs and proteins, molecules most typically peptides, proteins, and antibody fragments that can help to meet the challenges of improving the safety and efficiency of many therapeutics. It produces alterations in the physiochemical properties including changes in conformation, electrostatic binding, hydrophobicity etc. These physical and chemical changes increase systemic retention of the therapeutic agent. Also, it can influence the binding affinity of the therapeutic moiety to the cell receptors and can alter the absorption and distribution patterns.

Pegylation, by increasing the molecular weight of a molecule, can impart several significant pharmacological advantages over the unmodified form, such as: improved molecule (drug) solubility, reduced dosage frequency, without diminished efficacy with potentially reduced toxicity, extended circulating life, increased molecule (drug) stability, and enhanced protection from proteolytic degradation. Pegylated drugs have the following commercial advantages such as opportunities for new delivery formats and dosing regimens and extended patent life of previously approved drugs.

The first step of the Pegylation is the suitable functionalization of the PEG polymer at one or both terminals. PEGs that are activated at each terminus with the same reactive moiety are known as "homobifunctional", whereas if the functional groups present are different, then the PEG derivative is referred as "heterobifunctional" or "heterofunctional." The chemically active or activated derivatives of the PEG polymer are prepared to attach the PEG to the desired molecule. The overall Pegylation processes used to date for protein conjugation can be broadly classified into two types, namely a solution phase batch process and an on-column fed-batch process. The simple and commonly adopted batch process involves the mixing of reagents together in a suitable buffer solution, preferably at a temperature between 4 and 6° C., followed by the separation and purification of the desired product using a suitable technique based on its physicochemical properties, including size exclusion chromatography (SEC), ion exchange chromatography (IEX), hydrophobic interaction chromatography (HIC) and membranes or aqueous two phase systems.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, and tyrosine. The N-terminal amino group and the C-terminal carboxylic acid can also be used as a site-specific site by conjugation with aldehyde functional polymers.

The techniques used to form first generation PEG derivatives are generally reacting the PEG polymer with a group that is reactive with hydroxyl groups, typically anhydrides, acid chlorides, chloroformates and carbonates. In the second generation pegylation chemistry more efficient functional groups such as aldehyde, esters, amides, etc made available for conjugation. As applications of pegylation have become more and more advanced and sophisticated, there has been an increase in need for heterobifunctional PEGs for conjugation. These heterobifunctional PEGs are very useful in linking two entities, where a hydrophilic, flexible and biocompatible spacer is needed. Preferred end groups for heterobifunctional PEGs are maleimide, vinyl sulfones, pyridyl disulfide, amine, carboxylic acids and NHS esters. Third generation pegylation agents, where the shape of the polymer has been branched, Y shaped or comb shaped are available which show reduced viscosity and lack of organ accumulation.

Some aspects of the invention relate to a pharmaceutical composition of nanoparticles, the nanoparticles consisting of a shell portion that is dominated by positively charged chitosan, a core portion that consists of the positively charged chitosan, one negatively charged substrate, at least one pegylated bioactive agent loaded within the nanoparticles, and optionally a zero-charge compound. In one embodiment, the pegylated bioactive agent is an anti-diabetic drug that is covalently attached polyethylene glycol polymer chains. In another embodiment, the pegylated anti-diabetic drug is selected from the group consisting of insulin, an insulin analog, GLP-1, a GLP-1 analog, an insulin sensitizer, an insulin secretagogue, an inhibitor of dipeptidyl peptidase 4, metformin, alpha-glucosidase inhibitors, amylin analog, sodium-glucose co-transporter type 2 (SGLT2) inhibitors, benfluorex, tolrestat, and combinations thereof.

Example No. 25

Nanoparticles Loaded with Anti-Hemophilic Factors

Hemophilia is a group of hereditary genetic disorders that impair the body's ability to control blood clotting or coagulation. The effects of this sex-linked, X chromosome disorder are manifested almost entirely in males, although the gene for the disorder is inherited from the mother. Females have two X chromosomes while males have only one, lacking a 'back up' copy for the defective gene. Females are therefore almost exclusively carriers of the disorder, and may have inherited it from either their mother or father. These genetic deficiencies may lower blood plasma clotting factor levels of coagulation factors needed for a normal clotting process. When a blood vessel is injured, a temporary scab does form, but the missing coagulation factors prevent fibrin formation which is necessary to maintain the blood clot. Thus, a hemophiliac does not bleed more intensely than a normal person, but for a much longer amount of time. In severe hemophiliacs, even a minor injury could result in blood loss lasting days, weeks, or may never heal completely. The critical risk here is with normally small injuries, which, due to missing factor VIII, take extended periods of time to heal. In areas such as the brain or inside joints, this can be fatal or permanently debilitating.

In one exemplary preparation, nanoparticles were obtained upon addition of a mixture of γ-PGA and SonoSeven (a recombinant human coagulation Factor VIIa; rFVIIa) aqueous solution (2 ml), using a pipette (0.5-5 ml, PLASTIBRAND®, BrandTech Scientific Inc., Germany), into a low-MW CS aqueous solution (pH 6.0, 10 ml) at concentrations higher than 0.10% by w/v under magnetic stirring at room temperature to ensure positive surface charge. Nanoparticles were collected by ultracentrifugation at 38,000 rpm for 1 hour. rFVIIa is wholly or substantially totally encapsulated within the nanoparticles. Supernatants were discarded and nanoparticles were resuspended in deionized water as the solution products. Then they were either encapsulated in capsules/enteric capsules or treated with lyophilization freeze-dried process. The nanoparticles thus obtained via the simple and mild ionic-gelation method described herein show typical characteristics in a spheroidal configuration with a particle size of between about 50 to 400 nm, a positive surface charge, and a narrow polydispersity index.

Hemophilia A is an X-linked genetic disorder involving a lack of functional clotting Factor VIII and represents 90% of hemophilia cases. Hemophilia B is an X-linked genetic disorder involving a lack of functional clotting Factor IX. It is less severe but more uncommon than Hemophilia A. Hemophilia C is an autosomal recessive genetic disorder involving a lack of functional clotting Factor Xl. Though there is no cure for hemophilia, it can be conventionally controlled with regular infusions of the deficient clotting factor, i.e. factor VIII in hemophilia A or factor IX in hemophilia B. Factor replacement can be either isolated from human blood serum, recombinant, or a combination of the two. Some hemophiliacs develop antibodies (inhibitors) against the replacement factors given to them, so the amount of the factor has to be increased or non-human replacement products must be given, such as porcine factor VIII. Inhibitors are a complication of hemophilia. People with severe Hemophilia A or B is usually treated by replacing the missing Factor VIII or Factor IX through infusion. For some people, however, this treatment does not work. Their bodies react as though the treatment is an invader and their immune system develops antibodies (inhibitors) which attack and neutralize the Factor VIII or IX. The neutralized factor is not able to stop the bleeding.

In one aspect, Xyntha™ (Wyeth) anti-hemophilic factor (recombinant), plasma/serum-free is indicated for the control and prevention of bleeding episodes in an animal subject with hemophilia A (congenital factor VIII deficiency or classic hemophilia) and for surgical prophylaxis in an animal subject with hemophilia A. Patients can control bleeding episodes with normal plasma, concentrates of factor VII, or genetically produced (recombinant) factor VII. People need frequent treatment during bleeding episodes because factor VII does not last long. Women can control menstrual bleeding with oral contraceptives.

An activated concentrate of factor VII called NovoSeven can also be used. In one aspect, NovoSeven® (Novo Nordisk) is a recombinant human coagulation Factor VIIa (rFVIIa), intended for promoting hemostasis by activating the extrinsic pathway of the coagulation cascade. NovoSeven is a vitamin k-dependent glycoprotein consisting of 406 amino acid residues (MW 50 k Dalton). NovoSeven is structurally similar to human plasma-derived Factor VIIa. NovoSeven is supplied as a sterile, white lyophilized powder of rFVIIa in single-use vials. Some other brand names for the generic anti-hemophilic factor, recombinant-injection may include: Bioclate (Aventis Behring), Helixate (CSL Behring), Kogenate (Bayer Healthcare), Recombinate (Baxter Healthcare) Advate (Baxter Healthcare), Alphanate (Grifols SA), Hemofil-M (Baxter Healthcare), Humate-P (CLS Behrng), Koate (Talecris Biotherapeutics), Monarc-M (Baxter Healthcare), Monoclate-P (CSL Behring), Refacto (Wyeth), and others.

Idarubicin or 4-demethoxydaunorubicin is an anthracycline antileukemic drug that is currently combined with sytosine arabinoside as a first line treatment of acute myeloid leukemai. It belongs to the family of drugs called antitumor antibiotics. It is distributed under the trade names Zavedos (UK) and Idamycin (USA).

Some aspects of the invention relate to a method of promoting hemostasis caused by hemophilia in an animal subject, the method comprising orally administering nanoparticles composed of anti-hemophilic factor, chitosan, and a core substrate of poly(glutamic acid) or heparin, wherein a surface of the nanoparticles is dominated by chitosan. In one embodiment, the oral nanoparticles comprise chitosan or chitosan derivatives as a permeation enhancer. In another embodiment, the nanoparticles further comprise a permeation enhancer.

Some aspects of the invention relate to a pharmaceutical composition for treating a subject comprising two or more bioactive nanoparticles, thus treating the subject by co-administering the bioactive nanoparticles to the subject, wherein a first bioactive nanoparticle comprises a shell portion that is dominated by positively charged chitosan, a core portion that contains negatively charged substrate, wherein the negatively charged substrate is at least partially neutralized with a portion of the positively charged chitosan, and at least a first bioactive agent, and wherein a second bioactive nanoparticle comprises a shell portion that is dominated by positively charged chitosan, a core portion that contains negatively charged substrate, wherein the negatively charged substrate is at least partially neutralized with a portion of the positively charged chitosan, and at least a second bioactive agent.

In one embodiment, the first and second nanoparticles are loaded in same capsules. In another embodiment, the first nanoparticle is loaded in a first capsule and the second nanoparticle is loaded in a second capsule. In one embodiment, the capsules are treated with enteric coating. In a further embodiment, the capsules further comprise at least a solubilizer or pharmacopoeial excipients. In another embodiment, the capsules further comprise a permeation enhancer, wherein the permeation enhancer is selected from the group consisting of $Ca^{2+}$ chelators, bile salts, anionic surfactants, medium-chain fatty acids, phosphate esters, chitosan, and chitosan derivatives. In one embodiment, the first and second nanoparticles are loaded in tablets or pills.

In one embodiment, the first bioactive agent of the pharmaceutical composition comprises non-insulin anti-diabetic drug, wherein the non-insulin anti-diabetic drug is selected from the group consisting of insulin sensitizers, insulin secretagogues, GLP-1 analogs, and DPP-4 inhibitors, alpha-glucosidase inhibitors, amylin analog, sodium-glucose co-transporter type 2 (SGLT2) inhibitors, benfluorex, and tolrestat. In another embodiment, the second bioactive agent of the pharmaceutical composition comprises insulin or insulin analogs.

Example No. 26

Nanoparticles Loaded with DTPA

Some aspects of the invention relate to a pharmaceutical composition of nanoparticle comprising chitosan, PGA-complexone conjugate and a bioactive agent. In one embodiment, the PGA-complexone conjugate may broadly include a conjugate with PGA derivatives such as γ-PGA, α-PGA, derivatives of PGA or salts of PGA, whereas the complexone may cover DTPA (diethylene triamine pentaacetic acid), EDTA (ethylene diamine tetra acetate), IDA (iminodiacetic acid), NTA (nitrilotriacetic acid), EGTA (ethylene glycol tetraacetic acid), BAPTA (1,2-bis(o-aminophenoxy)ethane-N,N,N',N'-tetraacetic acid), DOTA (1,4,7,10-tetraazacyclododecane-N,N',N,N'-tetraacetic acid), NOTA (2,2',2"-(1,4,7-triazonane-1,4,7-triyl)triacetic acid), and the like. A polyamino carboxylic acid (complexone) is a compound containing one or more nitrogen atoms connected through carbon atoms to one or more carboxyl groups.

Diethylene triamine pentaacetic acid (DTPA) is a polyamino carboxylic acid consisting of a diethylenetriamine backbone modified with five carboxymethyl groups. The molecule can be viewed as an expanded version of EDTA. DTPA is used as its conjugate base, often undefined, which has a high affinity for metal cations. In example, upon complexation to lanthanide and actinide ions, DTPA exists as the pentaanionic form, i.e. all five carboxylic acid groups are deprotonated. DTPA has a molecular formula of $C_{14}H_{23}N_3O_{10}$ with molar mass 393.358 g/mole. The chemical formula for DTPA and EGTA are shown below as:

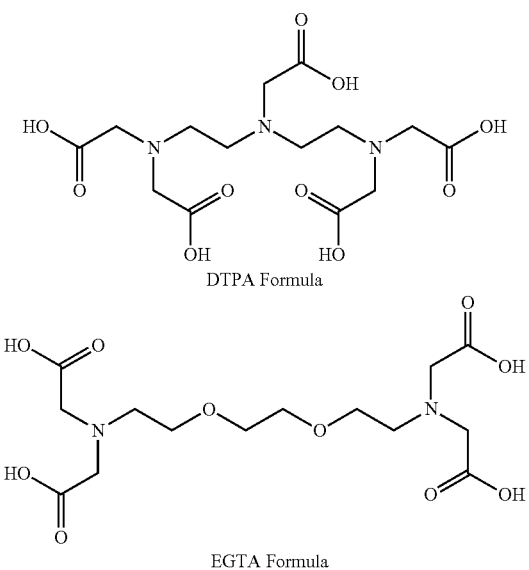

DTPA Formula

EGTA Formula

Currently, DTPA is approved by the U.S. Food and Drug Administration (FDA) for chelation of three radioactive materials: plutonium, americium, and curium. DTPA is the parent acid of an octadentate ligand, diethylene triamine pentaacetate. In some situations, all five acetate arms are not attached to the metal ion. In one aspect of the present invention, DTPA has been conjugated to γ-PGA through hexanediamine ((γ-PGA)-DTPA) as illustrated below:

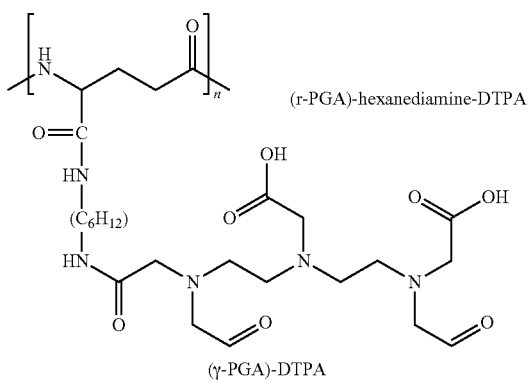

(γ-PGA)-DTPA

In one aspect of the invention, (γ-PGA)-DTPA is one species of the PGA-complexone conjugates used in the current pharmaceutical composition of nanoparticles. The overall degree of substitution of DTPA in (γ-PGA)-DTPA conjugate is generally in the range of about 1-70%, preferably in the range of about 5-40%, and most preferably in the range of about 10-30%. DTPA does not build up in the body or cause long-term health effects.

Nanoparticles comprising chitosan, PGA-complexone conjugates and at least one bioactive agent using the simple and mild ionic-gelation process described herein has demonstrated the desired paracellular transport efficacy with TEER measurements in the Caco-2 cell cultures model as described in Example No. 4.

Example No. 27

Enzyme Inhibition Study with (γ-PGA)-DTPA Conjugate

Figure 20:
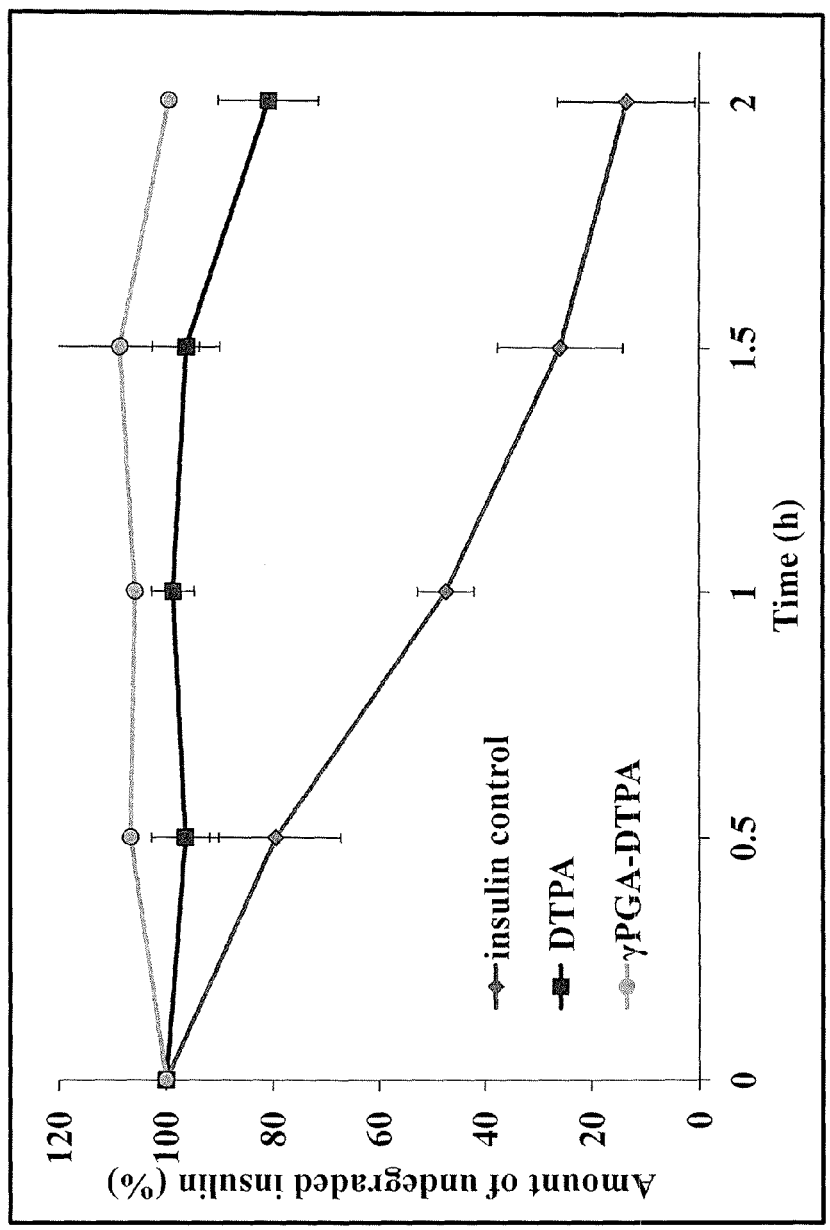
FIG. 20 shows experimental data on enzyme inhibition study with (γ-PGA)-DTPA conjugate.

Brush border membrane bounded enzymes were used to simulate a contacting membrane at the bottom of a donor compartment, wherein the insulin-loaded medium (Krebs-Ringer buffer) in the donor compartment was used as the starting material at time zero. Three elements were used in this enzyme inhibition study to assess the enzymatic degradation of insulin versus time by brush border membrane bounded enzymes. They were (a) insulin 1 mg/ml as control; (b) DTPA 5 mg/ml; and (c) (γ-PGA)-DTPA 5 mg/ml. As shown in FIG. 20, both DTPA and (γ-PGA)-DTPA substantially protect or maintain the insulin activity or viable content over the experimental duration up to 2 hours. Some aspects of the present invention provide a pharmaceutical composition of nanoparticles, the nanoparticles comprising a shell portion that is dominated by positively charged chitosan, a core portion that comprises complexone and one negatively charged substrate, wherein the substrate is PGA, wherein the negatively charged substrate is at least partially neutralized with a portion of the positively charged chitosan in the core portion, and at least one bioactive agent loaded within the nanoparticles. In one embodiment, the PGA is conjugated with the complexone to form PGA-complexion conjugates within the nanoparticles.

Some aspects of the invention provide a method of enhancing enzymatic resistance of a bioactive agent in oral administration by encapsulating the bioactive agent in nanoparticles, wherein the nanoparticles have a pharmaceutical formulation and/or composition as described in this disclosure and in claims. In one embodiment, the nanoparticles are further loaded with pharmaceutically acceptable carrier, diluent, or excipient in tablets, pills, capsules, and the like.

Example No. 28

Intestinal Applications of CS-NPs in Inflammatory Bowel Diseases

In medicine, inflammatory bowel disease (IBD) is a group of inflammatory conditions of the colon and small intestine. The major types of IBD are Crohn's disease (autoimmune origin), and ulcerative colitis. Accounting for far fewer cases are other forms of IBD, which are not always classified as typical IBD: collagenous colitis, lymphocytic colitis, ischemic colitis, diversion colitis, Behcet's disease and indeterminate colitis. This targeted delivery to inflamed tissue in IBDs is based on the principle of pH-responsive chitosan/γ-PGA NPS wherein the γ-PGA may be a conjugate version such as (γ-PGA)-DTPA, (γ-PGA)-EGTA, (γ-PGA)-EDTA or the like with a complexion species. The current drug-loaded CS-NPs are also applicable for treatment of irritable bowel syndrome (IBS).

Optimal treatment of inflammatory bowel disease depends on what form it consists of. For example, mesalazine is more useful in ulcerative colitis than in Crohn's disease. Generally, depending on the level of severity, IBD may require immunosuppression to control the symptom, such as prednisone, TNF inhibition, azathioprine (Imuran), methotrexate or 6-mercaptopurine. More commonly, treatment of IBD requires a form of mesalazine. Often, steroids are used to control disease flares and were once acceptable as a maintenance drug. In use for several years in Crohn's disease patients and recently in patients with ulcerative colitis, biologicals have been used such as TNF inhibitors. Severe cases may require surgery, such as bowel resection, strictureplasty or a temporary or permanent colostomy or ileostomy. Alternative medicine treatments for bowel disease exist in various forms, however such methods concentrate on controlling underlying pathology in order to avoid prolonged steroidal exposure or surgical excisement.

Usually the treatment is started by administering drugs with high anti-inflammatory effects, such as prednisone. Once the inflammation is successfully controlled, the patient is usually switched to a lighter drug to keep the disease in remission, such as Asacol, a mesalamine. If unsuccessful, a combination of the aforementioned immunosuppression drugs with a mesalamine (which may also have an anti-inflammatory effect) may or may not be administered, depending on the patient. *Histoplasma* produces toxins that cause intestinal disease called histoplasmosis that is a "serious consideration" in an immunocompromised patient with signs and symptoms of IBD. Antifungal drugs such as nystatin (a broad spectrum gut antifungal) and either itraconazole (Sporanox) or fluconazole (Diflucan) have been suggested as a treatment for IBD disorders such as Crohn's disease and ulcerative colitis that all share the same symptoms such as diarrhea, weight loss, fever, and abdominal pain.

New evidence suggests that patients with IBD may have an elevated risk of endothelial dysfunction and coronary artery disease. The extra-intestinal complication of Crohn's disease and ulcerative colitis may include iritis, uveitis, primary sclerosing cholangitis, ankylosing spondylitis, pyoderma gangrenosum, ethryema nodosum, and others.

More specifically, the pH in inflamed tissue is about pH 5.5 or less. (NPs have higher zeta potential at this pH) whereas Crohn's disease is generally located in ileum or colon where normal pH is 7.0-8.0. Chitosan-shelled NPs can adhere more strongly to the inflamed tissue as compared to the normal tissue because its pH sensitivity. More targets in inflamed tissue can be approached by chitosan-shelled NPs for better specificity of delivery system. Some aspects of the invention relate to method of treating an inflammatory bowel disease of an animal subject, the method comprising administering bioactive nanoparticles to the animal subject orally, wherein the bioactive nanoparticles consist of at least one anti-inflammatory agent, positively charged chitosan, optionally a zero-charge substance or bioactive agent, and a negatively charged substrate, wherein a surface of the nanoparticles is dominated by the positively charged chitosan.

Example No. 29

Imaging of IBDs Using CS-NPs as MRI Contrast Agent

Currently diagnosis of inflammatory bowel diseases (IBDs) is performed by endoscopy, which is inconvenient. DTPA-Gd is a commercial MRI contrast agent (for example, MAGNEVIST by Bayer Healthcare, Wayne, N.J.). Gadolinium is paramagnetic at room temperature. The γPGA-DTPA conjugate can be used to chelate Gd (gadolinium) to form Gd-based γPGA-DTPA conjugate. The Gd-loaded CS/γPGA-DTPA NPs (preferably CS/γPGA-DTPA-Gd NPs can specifically adhere to inflamed tissue due to the pH sensitivity of chitosan-shelled NPs which can be imaged using an MRI system. US FDA approved Gd chelated contrast agents include: Omniscan (manufactured by GE Healthcare), Multihance (manufactured by Bracco), Magnevist (manufactured by Bayer Healthcare), ProHance (manufactured by Bracco), Vasovist, Eovist, OptiMark (manufactured by Mallinckrodt), etc.

Some aspects of the invention relate to a pharmaceutical composition of nanoparticles with enhanced imaging contrast quality (property) during an imaging procedure, the nanoparticles consisting of positively charged chitosan, optionally a zero-charge substance or bioactive agent, and a negatively charged substrate having gadolinium (Gd) chelated to the negatively charged substrate, wherein a surface of the nanoparticles is dominated by the positively charged chitosan. In one embodiment, the negatively charged substrate is a PGA-complexone conjugate. Some aspects of the invention relate to a method of using the nanoparticles with enhanced imaging contrast property of the present invention for imaging inflammatory bowel diseases. In another embodiment, the imaging procedure is an MRI, X-ray, positron emission tomography (PET) procedure or magnetic resonance angioplasty. In one embodiment, the gadolinium chelated to the negatively charged substrate may be a gadolinium complex or a gadolinium compound; for example, gadoversetamide and terbium-doped gadolinium oxysulfide.

Some aspects of the invention relate to a pharmaceutical composition of nanoparticles, the nanoparticles consisting of positively charged chitosan, optionally a zero-charge substance or bioactive agent, and a negatively charged substrate having gadolinium (Gd) chelated to the negatively charged substrate, wherein a surface of the nanoparticles is dominated by the positively charged chitosan. In one embodiment negatively charged substrate is a PGA-complexone conjugate, γ-PGA, α-PGA, derivatives of PGA, salts of PGA, or combinations thereof. The nanoparticles are used in enhancing imaging contrast quality or property during an imaging procedure.

Example No. 30

Systemic Applications of Multifunctional NPs for Imaging Cancer Tissues

TMC or PEG-CS may be used as a component to improve pH stability of CS-NPs at around physiological pH (pH 7.4). NPs or a pharmaceutical composition of NPs prepared using TMC/γPGA-DTPA-Gd can be used as MRI contrast agent. The free —$NH_3$ groups on TMC (N-trimethyl chitosan) can be used to attach specific ligands for targeting the cancer tissue. In biochemistry and pharmacology, a ligand is a substance that forms a complex with a biomolecule to serve a biological purpose. In a narrower sense, it is a signal-triggering molecule, binding to a site on a target protein ("docking"). The binding occurs by intermolecular forces, such as ionic bonds, hydrogen bonds and van der Waals forces. The docking (association) is usually reversible (dissociation). Ligand binding to a receptor alters the chemical conformation, which is the three dimensional shape of the receptor protein. The conformational state of a receptor protein determines the functional state of a receptor.

Ligands include substrates, inhibitors, activators, and neurotransmitters. The tendency or strength of binding is called affinity. Binding affinity data alone does not determine the overall potency of a drug. Potency is a result of the complex interplay of both the binding affinity and the ligand efficacy. Ligand efficacy refers to the ability of the ligand to produce a biological response upon binding to the target receptor and the quantitative magnitude of this response. This response may be as an agonist, antagonist, or inverse agonist, depending on the physiological response produced. A ligand that can bind to a receptor, alter the function of the receptor and trigger a physiological response is called an agonist for that receptor. Ligands that bind to a receptor but fail to activate the physiological response are receptor "antagonists".

For example, "galactosamine" ligand can be attached to a free —$NH_3$ group of TMC chitosan portion of a nanoparticle, whereas the galactosamine is a liver cancer targeting moiety that may bind to a target receptor on the liver cancer. The nanoparticles are administered to an animal subject via an oral or parenteral route. The parenteral route administration is hereby defined as medicine taken into the body or administered in a manner other than through the digestive tract. The parenteral route includes intravenous, intramuscular, intrapercutaneous, subcutaneous, through mucus membrane, and the like.

Some aspects of the invention relate to a pharmaceutical composition of nanoparticles, the nanoparticles consisting of positively charged chitosan having free —$NH_3$ groups to attach specific ligands for binding to a target receptor on cancer tissue, optionally a zero-charge substance or bioactive agent and a negatively charged substrate having gadolinium (Gd) chelated to the negatively charged substrate, wherein a surface of the nanoparticles is dominated by the positively charged chitosan.

In one embodiment, the negatively charged substrate is a PGA-complexone conjugate. In one embodiment, the nanoparticles have dual functions: for binding toward cancer/tumor tissue and for imaging purposes. Optionally, the nanoparticles could load a bioactive agent (for example, an anticancer drug) for cancer treatment.

Example No. 31

Nanoparticles and Inflammatory Bowel Diseases

Some patients with inflammatory bowel disease may be at increased risk for skin cancer due to their use of immunosuppressant drugs to treat the intestinal disorder, according to the results of two new studies. Glucagon-like peptide-2 (GLP-2) is a 33 amino-acid peptide in humans. GLP-2 is created by specific post-translational proteolytic cleavage of proglucagon in a process that also liberates the related glucagon-like peptide-1(GLP-1). GLP-2 is produced by the intestinal endocrine L cell and by various neurons in the central nervous system. Intestinal GLP-2 is co-secreted along with GLP-1 upon nutrient ingestion. When externally administered, GLP-2 produces a number of effects in humans and rodents, including intestinal growth, enhancement of intestinal function, reduction in bone breakdown and neuroprotection. GLP-2 may act in an endocrine fashion to link intestinal growth and metabolism with nutrient intake. GLP-2 and related analogs may be treatments for short bowel syndrome, Crohn's disease, osteoporosis and as adjuvant therapy during cancer chemotherapy.

Short Bowel Syndrome

Short bowel syndrome (SBS, also short gut syndrome or simply short gut) is a malabsorption disorder caused by the surgical removal of the small intestine, or rarely due to the complete dysfunction of a large segment of bowel. Symptoms of short bowel syndrome are usually addressed by prescription medicine. These include: (a) Anti-diarrheal medicine (e.g. loperamide, codeine); (b) Vitamin, mineral supplements and L-Glutamine powder mixed with water; (c) $H_2$ blocker (i.e., $H_2$ receptor antagonists, for example, cimetidine, ranitidine, famotidine, nizatidine) and protein pump inhibitors to reduce stomach acid; (d) Lactase supplement (to improve the bloating and diarrhea associated with lactose intolerance); (e) Surgery, including intestinal lengthening, tapering, and small bowel transplant; (f) Parenteral nutrition (PN or TPN for total parenteral nutrition—nutrition administered via intravenous line); and (g) Nutrition administered via gastrostomy tube.

There reports a therapy that reduces the frequency and volume of TPN, comprising: NutreStore™ (L-glutamine for oral solution) and Zorbtive (somatropin (rDNA origin) for injection) together with a specialized oral diet (Ann Surg. 2005; 242; 655-661). Some aspects of the invention relate to a composition of nanoparticles for treatment of bowel syndrome of an animal subject, the bioactive nanoparticles consisting of at least one antagonist for treating the bowel syndrome, positively charged chitosan, optionally a zero-charge substance and a negatively charged substrate of polyglutamic acid (PGA), wherein the negatively charged substrate is neutralized with a portion of the positively charged chitosan in a core portion of the nanoparticles. In one embodiment, the bowel syndrome may include short bowel syndrome, inflammatory bowel syndrome or irritable bowel syndrome.

In one embodiment, the antagonist for treating bowel syndrome (or short bowel syndrome) is selected from the group consisting of GLP-2, GLP-2 analogs, anti-diarrheal medicine (for example, codeine, loperamide, flavonoid, attapulgite, motofen, and the like), $H_2$ blocker (for example, cimetidine, ranitidine, famotidine, nizatidine, and the like), protein pump inhibitors, and the like.

Crohn's Diseases and Drugs

Crohn's disease, also known as regional enteritis, is a type of inflammatory bowel disease that may affect any part of the gastrointestinal tract from mouth to anus, causing a wide variety of symptoms. It primarily causes abdominal pain, diarrhea (which may be bloody if inflammation is at its worst), vomiting (can be continuous), or weight loss. Crohn's disease is caused by interactions between environmental, immunological and bacterial factors in genetically susceptible individuals.

Crohn's disease has traditionally been described as an autoimmune disease, but recent investigators have described it as a disease of immune deficiency. Crohn's disease is one type of inflammatory bowel disease (IBD). It typically manifests in the gastrointestinal tract and can be categorized by the specific tract region affected. A disease of both the ileum (the last part of the small intestine which connects to the large intestine), and the large intestine. Ileocolic Crohn's accounts for fifty percent of cases. In addition to systemic and gastrointestinal involvement, Crohn's disease can affect many other organ systems. Crohn's disease can cause significant complications, including bowel obstruction, abscesses, free perforation and hemorrhage. A colonoscopy is the best test for making the diagnosis of Crohn's disease, as it allows direct visualization of the colon and the terminal ileum, identifying the pattern of disease involvement. On occasion, the colonoscope can travel past the terminal ileum, but it varies from patient to patient. Acute treatment uses medications to treat any infection (normally antibiotics) and to reduce inflammation (normally aminosalicylate anti-inflammatory drugs and corticosteroids). Medications used to treat the symptoms of Crohn's disease include 5-aminosalicylic acid (5-ASA) formulations, prednisone, immunomodulators such as azathioprine, methotrexate, mercaptopurine, infliximab, adalimumab, certolizumab and natalizumab.

Numerous preclinical studies demonstrate that activation of the CB1 and CB2 cannabinoid receptors exert biological functions on the gastrointestinal tract. Activation of CB1 and CB2 receptors in animals has shown a strong anti-inflammatory effect. Cannabinoids and/or modulation of the endocannabinoid system is a novel therapeutic means for the treatment of numerous GI disorders, including inflammatory bowel diseases like Crohn's disease. Major drugs for treating Crohn's diseases include: (a) Methotrexate, which is a folate anti-metabolite drug that is also used for chemotherapy. It is useful in maintenance of remission for those no longer taking corticosteroids. (b) Metronidazole and ciprofloxacin, which are antibiotics used to treat Crohn's that have colonic or perianal involvement. They are also used for treatment of complications, including abscesses and other infections accompanying Crohn's disease. (c) Thalidomide has shown response in reversing endoscopic evidence of disease. (d) *Cannabis*-derived drugs may be used to treat Crohn's disease with their anti-inflammatory properties. *Cannabis*-derived drugs may also help to heal the gut lining.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A composition of bioactive nanoparticles for treatment of bowel syndrome of an animal subject, the bioactive nanoparticles consisting of at least one antagonist for treating said bowel syndrome, positively charged chitosan, optionally a zero-charge substance and a negatively charged substrate of polyglutamic acid (PGA), wherein said negatively charged substrate is neutralized with a portion of said positively charged chitosan in a core portion of said nanoparticles.

2. The composition of claim 1, wherein said antagonist is GLP-2 or GLP-2 analogs.

3. The composition of claim 1, wherein said bowel syndrome is short bowel syndrome, inflammatory bowel syndrome, or irritable bowel syndrome.

4. The composition of claim 3, wherein said antagonist is anti-diarrheal medicine for treatment of short bowel syndrome.

5. The composition of claim 3, wherein said antagonist is an $H_2$ blocker or protein pump inhibitor for treatment of short bowel syndrome.

6. The composition of claim 1, wherein said chitosan is N-trimethyl chitosan, EDTA-chitosan, low molecular weight chitosan, PEG-chitosan, mono-N-carboxymethyl chitosan, chitosan derivatives, or combinations thereof.

7. The composition of claim 1, wherein said nanoparticles are formulated into a tablet or pill configuration.

8. The composition of claim 7, wherein said tablet or pill is treated with an enteric coating polymer.

9. The composition of claim 1, wherein said nanoparticles are encapsulated in a capsule.

10. The composition of claim 9, wherein said capsule further comprises a pharmaceutically acceptable carrier, diluent, excipient, solubilizer, bubbling agent, or emulsifier.

11. The composition of claim 9, wherein said capsule is treated with an enteric coating polymer.

12. The composition of claim 9, wherein said capsule further comprises at least one permeation enhancer.

13. The composition of claim 12, wherein said permeation enhancer is selected from the group consisting of $Ca^{2+}$ chelators, bile salts, surfactants, medium-chain fatty acids, phosphate esters, chitosan, and chitosan derivatives.

14. The composition of claim 1, wherein said nanoparticles are freeze-dried, thereby said nanoparticles being in a powder form.

15. The composition of claim 1, wherein said nanoparticles are mixed with trehalose and then freeze-dried, thereby said nanoparticles being in a powder form.

16. The composition of claim 1, wherein said nanoparticles are treated with an enteric coating polymer.

17. The composition of claim 1, wherein said PGA that is selected from the group consisting of a PGA-complexone conjugate, γ-PGA, α-PGA, derivatives of PGA, salts of PGA, and combinations thereof.

18. The composition of claim 17, wherein the PGA-complexone conjugate has chelated gadolinium.

19. The composition of claim 1, wherein said zero-charge substance is a permeation enhancer.

20. The composition of claim 1, wherein said antagonist is selected from the group consisting of cimetidine, ranitidine, famotidine, nizatidine, codeine, loperamide, flavonoid, attapulgite, and motofen.

* * * * *